(12) United States Patent
Lebedeva et al.

(10) Patent No.: US 8,445,271 B2
(45) Date of Patent: May 21, 2013

(54) PROCESSES AND KITS FOR DETERMINING MULTI-DRUG RESISTANCE OF CELLS

(75) Inventors: Irina Lebedeva, Bronx, NY (US); Praveen Pande, Holbrook, NY (US); Wayne Forrest Patton, Dix Hills, NY (US)

(73) Assignee: Enzo Life Sciences, Inc., Farmingdale, NY (US)

( * ) Notice: Subject to any disclaimer, the term of this patent is extended or adjusted under 35 U.S.C. 154(b) by 240 days.

(21) Appl. No.: 12/799,853

(22) Filed: May 3, 2010

(65) Prior Publication Data

US 2011/0269168 A1    Nov. 3, 2011

(51) Int. Cl.
*C12N 15/00* (2006.01)

(52) U.S. Cl.
USPC ............................ 435/325; 435/334; 435/383

(58) Field of Classification Search
USPC ......................................... 435/325, 334, 383
See application file for complete search history.

(56) References Cited

PUBLICATIONS

Bauer et al. "Compound profiling for P-glycoprotein at the blood-brain barrier using a microplate screening system", Pharmaceutical Research, 2003, 20(8):1170-1176.*
Evers et al. "Inhibitory effect of the reversal agents V-104, GF120918 and Pluronic L61 on MDR1 Pgp-, MRP1- and MRP2-mediated transport", Cancer Research Campaign, 2000, 83(3):366-374.*
Calcein AM, from Handbook of biological dyes and stains. 2010, total 3 pages.*
Chemicon "Multidrug resistance direct dye efflux assay", 2003, 16 pages.*
Wemhoner et al. "A fluorescent microplate assay for exocytosis in alveolar type II cells", J of Biomolecular Screening, 2006:286-295.*
Bernhard et al. "Enhanced MTT-reducing activity under growth inhibition by resveratrol in CEM-C7H2 lymphocytic leukemia cells", Cancer Letters, 2003, 195:193-199.*
Cantz et al., MRP2, a human conjugate export pump, is present and transports fluo 3 into apical vacuoles of Hep G2 cells, Am J Physiol Gastrointest Liver Physiol 2000, G522-G531, 278.
Collington et al., Polaraized efflux of 2', 7'-bis(2-carboxyethyl)-5(6)-carboxyfluorescein from cultured epithelial cell monolayers, Biochemical Pharmacology 1992, 417-424, 44.
Demarco et al., Efflux-Related Resistance to Norfloxacin, Dyes, and Biocides in Bloodstream Isolates of *Staphylococcus aureus*, Antimicrobial Agents and Chemotherapy, 2007, 3235-3239, 51.
Doyle and Ross, Multidrug resistance mediated by the breast cancer resistance protein BCRP (ABCG2), Oncogene 2003, 7340-7358, 22.
Gottesman et al., Multidrug resistance in cancer: role of ATP-dependent transporters, Nat Rev Cancer 2002, 48-58, 2.
Gupta, Radhey S., Intrinsic multidrug resistance phenotype of chinese hamster (rodent) cells in comparison to human cells, Biochem Biophys Res Comm 1988, 598-605, 153.

Haimeur et al., The MRP-Related and BCRP/ABCG2 Multidrug Resistance Proteins: Biology, Substrate Specificity and Regulation, Current Drug Metabolism, 2004, 21-53, 5.
Hediger et al., The ABCs of solute carriers: physiological, pathological and therapeutic implications of human membrane transport proteins, Pflugers Arch—Eur J Physiol 2004, 465-468, 447.
Hollo et al., Calcein accumulation as a fluorometric functional assay of the multidrug transporter, Biochimica et Biophysica Acta 1994, 384-388, 1191.
Homolya et al., A new method for quantitative assessment of P-glycoprotein-related multidrug resistance in tumour cells, British Journal of Cancer 1996, 849-855, 73.
Horio et al., Transepithelial Transport of Drugs by Multidrug Transporter in Cultured Madin-Darby Canine Kidney Cell Epithelia, J Biol Chem 1989, 14880-14884, 264.
Horio et al., ATP-dependent transport of vinblastine in vesicles from human multidrug-resistant cells, Proc. Natl. Acad. Sci. USA 1988, 3580-3584, 85.
Hunter et al., Epithelial secretion of vinblastine by human intestinal adenocarcinoma cell (HCT-8 and T84) layers expressing P-glycoprotein, Br. J. Cancer 1991, 437-444, 64.
Koshiba et al., Human ABC transporters ABCG2 (BCRP) and ABCG4, Xenobiotica, 2008; 863-888, 38.
Kusuhara and Sugiyama, Active Efflux across the Blood-Brain Barrier: Role of the Solute Carrier Family, NeuroRx, 2005, 73-85, 2.
Leonard et al., The role of abc transporters in clinical practice, The Oncologist, 2003, 411-424, 8.
Liminga et al., Microfluorometric evaluation of calcein acetoxymethyl ester as a probe for P-glycoprotein-mediated resistance: effects of cyclosporin A and its nonimmunosuppressive analogue SDZ PSC 833, Exp Cell Res 1994, 291-296, 212.
Ling et al., Multidrug-Resistance Phenotype in Chinese Hamster Ovary Cells, Cancer Treat Rep 1983, 869-874, 67.
Litman et al., From MDR to MXR: new understanding of multidrug resistance systems, their properties and clinical significance, Cell. Mol. Life Sci. 2001, 931-959, 58.
Litman et al., The multidrug-resistant phenotype associated with overexpression of the new ABC half-transporter, MXR (ABCG2), Journal of Cell Science 2000, 2011-2021,113.
Marzolini et al., Pharmacogenomics of the OATP and OAT families, Pharmacogenomics, 2004, 273-282, 5.
McCollum et al., P-Glycoprotein—Mediated Resistance to Hsp9O-Directed Therapy is Eclipsed by the Heat Shock Response, Cancer Res 2008, 7419-7427, 68.
Miyazaki et al., The multispecific organic anion transporter family: properties and pharmacological significance, Trends in Pharmacological Sciences, 2004, 654-662, 25.
Mosmann, Tim, Rapid Colorimetric Assay for Cellular Growth and Survival: Application to Proliferation and Cytotoxicity Assays, Journal of Immunological Methods, 1983, 55-63, 65.

(Continued)

*Primary Examiner* — Bin Shen
(74) *Attorney, Agent, or Firm* — Elie Gendloff, Esq.

(57) ABSTRACT

This invention relates to multi-drug resistance (MDR) in cells, and the use of certain xanthene compounds for determining drug resistance in cells and the effect of test compounds on cell membrane transport by the membrane transporters MDR1, MRP and BCRP. Processes and kits for making these determinations and measuring these effects are described and provided.

54 Claims, 30 Drawing Sheets

PUBLICATIONS

Neyfakh et al., Efflux-mediated multidrug resistance in *Bacillus subtilis*: Similarities and dissimilarities with the mammalian system, Proc. Nati. Acad. Sci. USA, 1991, 4781-4785, 88.

Pages et al., Inhibitors of efflux pumps in Gram-negative bacteria, Trends in Molecular Medicine, 2005 382-389, 11.

Polli et al., Rational Use of in Vitro P-glycoprotein Assays in Drug Discovery, J Pharmacol Exp Ther 2001, 620-628, 299.

Putman et al., Molecular Properties of Bacterial Multidrug Transporters, Microbiology and Molecular Biology Reviews, 2000, 672-693, 64.

Rautio et al., In vitro P-glycoprotein inhibition assays for assessment of clinical drug interaction potential of new drug candidates: a recommendation for probe substrates, Drug Metabolism and Disposition, 2006, 786-792, 34.

Roelofsen et al., Increased Levels of the Multidrug Resistance Protein in Lateral Membranes of Proliferating Hepatocyte-Derived Cells, Gastroenterology 1997, 511-521, 112.

Scharenberg et al., The ABCG2 transporter is an efficient Hoechst 33342 efflux pump and is preferentially expressed by immature human hematopoietic progenitors, Blood. 2002, 507-512, 99.

Schinkel and Jonker, Mammalian drug efflux transporters of the ATP binding cassette (ABC) family: an overview, Advanced Drug Delivery Reviews 2003, 3-29, 55.

Tiberghien and Loor, Ranking of P-glycoprotein substrates and inhibitors by a calcein-AM fluorometry screening assay, Anti-Cancer Drugs, 1996, 568-578, 7.

Van Der Heijden et al., Involvement of Breast Cancer Resistance Protein Expression on Rheumatoid Arthritis Synovial Tissue Macrophages in Resistance to Methotrexate and Leflunomide, Arthritis & Rheumatism, 2009, 669-677, 60.

Van Veen et al., A bacterial antibiotic resistance gene that complements the human multidrug-resistance P-glycoprotein gene, Nature, 1998, 291-295, 391.

Van Veen et al., Multidrug resistance mediated by a bacterial homolog of the human multidrug transporter MDR1, Proc. Natl. Acad. Sci. USA 1996,10668-10672, 93.

Viveiros et al., New Methods for the Identification of Efflux Mediated MDR Bacteria, Genetic Assessment of Regulators and Efflux Pump Constituents, Characterization of Efflux Systems and Screening for Inhibitors of Efflux Pumps, Current Drug Targets, 2008, 760-778, 9.

Yee, Shiyin, In vitro permeability across Caco-2 cells (colonic) can predict in vivo (small intestinal) absorption in man-fact or myth, Pharmaceutical Research, 1997, 763-766, 14.

Young, Ian T., Proof without prejudice: use of the kolmogorov-smirnov test for the analysis of histograms from flow systems and other sources, J Histochem Cytochem, 1977, 935-941, 25.

Zhang et al., A regulatory viewpoint on transporter-based drug interactions, Xenobiotica, 2008, 709-724, 38.

\* cited by examiner

FIG. 1-1    PRIOR ART

Table 1: Selectivity and specificity of various fluorescent probes developed for MDR detection:

| FLUORESCENT PROBE | EXCITATION MAXIMUM (nm) | EMISSION MAXIMUM (nm) | SELECTIVITY | REFERENCE |
|---|---|---|---|---|
| BBR 3390 (aza-anthrapyrazole) | [488] | [525] | ABCG2 | Hazlehurst et al, 1999 |
| BCECF AM, (2', 7'-bis(2-carboxyethyl)-5(6)-carboxyfluorescein | | | MDR1 | Homolya et al, 1993; Brezden et al, 1994 |
| BODIPY – ceramide | | | | Elliott et al, 2004 |
| BODIPY – Taxol | | | Pgp | Binaschi et al, 1995; Fellner et al, 2002; Elliott et al, 2004 |
| BODIPY – Prazosin | | | Pgp | Lee et al, 1998 |
| | | | BCRP | Litman et al, 2000; Robey et al, 2003; Van der Pol et al, 2003; Elliott et al, 2004 |
| BODIPY – Verapamil | | | Pgp | Dey et al, 1999; Elliott et al, 2004 |
| Calcein | 470 | 509 | MRP | Hollo et al, 1994; Homolya et al, 1993; Homolya et al, 1996; Elliott et al, 2004 |
| Calcein AM | | | MRP1 | Dogan et al, 2004 |
| CDCF, 5(6)-carboxy-2',7'-dichlorofluorescein | | | MRP2/ABCC2 | Laupeze et al, 1999; Heredi-Szabo et al, 2008 |
| CFDA, carboxyfluorescein diacetate | | | MRP1 | Dogan et al, 2004; van der Kolk et al, 1998 |
| CMFDA (product GSMF, glutathione methylfluorescein) | | | MRP1/2 | Roelofsen et al, 1997; Gutmann et al, 1999 |
| DiOC$_2$(3) | 444 | 512 | Pgp | Minderman et al, 1996 |

FIG. 1-2    PRIOR ART

Table 1: Selectivity and specificity of various fluorescent probes developed for MDR detection:

| Probe | | | Target | Reference |
|---|---|---|---|---|
| Doxorubicine | | | Pgp | Broxterman et al, 1996a |
| | | | MRP | Priebe et al, 1998; Young et al, 1999 |
| | | | mutABCG2 | Bogush et al, 1995; Garcia-Escarp, et al, 2004 |
| Daunorubicine | | | Pgp | Bogush et al, 1995; Brooks et al, 2003 |
| | | | MRP | Priebe et al, 1998 |
| | | | mutABCG2 | Garcia-Escarp et al, 2004, Merlin et al, 1995; Doyle et al, 1998 |
| Epirubicin | | | Pgp | Bogush et al, 1995 |
| Fluo-3 AM | | | MDR | Wall et al, 1990; Homolya et al, 1993; Brezden et al, 1994; Oricky et al, 2004; Elliott et al, 2004 |
| | | | MRP | Cantz et al, 2000; Prechtl et al, 2000 |
| Fluo-4 AM | | | | Homolya et al, 1993; Elliott et al, 2004 |
| Fura-2 AM | | | MRP1 | Chearwae et al, 2006; Elliott et al, 2004 |
| Fura-Red AM | | | Pgp | Di Virgilio et al, 1990; Homolya et al, 1993; Fu et al, 2002 |
| JC-1 | | | | Abrahamse et al, 2001; Elliott et al, 2004 |
| | | | MDR1/ABCB1 | Kuhnel et al, 1997; Legrand et al, 2001 |
| | | | ABCG2 | |
| Hoechst 33342 | 365 | 400 | Pgp | Shapiro & Ling, 1997; Lalmy et al, 1995 |
| Indo - 1 AM | | | ABCG2 | Homolya et al, 1993; Wierdl et al, 2003 |
| LysoTracker Green | | | MDR1 | Bresden et al, 1994 |
| | | | ABCG2 | Robey et al, 2001 |
| MitoTracker Green | | | Pgp | Marques-Santos et al, 2003 |

FIG. 1-3    PRIOR ART

Table 1: Selectivity and specificity of various fluorescent probes developed for MDR detection:

| Compound | | | Target | Reference |
|---|---|---|---|---|
| Mitoxantrone | 647 | 670 | Pgp | Taylor et al, 1991 |
| | | | MRP | Morrow et al, 2006 |
| | | | ABCG2 | Robey et al, 2001; Minderman et al, 2002; Wierdl et al, 2003; Elliott et al, 2004; Litman, 2000 |
| Monochlorobimane | 390 | 478 | MRP2 | Roelofsen et al, 1995 |
| Rhodamine 6G | 527 | 552 | MRP | Neyfakh et al, 1988; Yeheskely-Hayon et al, 2009 |
| | | | Pgp/ABCB1 | Kessel et al, 1991; Feller et al, 1995; Neyfakh et al 1988; Lee et al, 1994; Twentyman et al, 1994; Broxterman et al, 1997 |
| Rhodamine 123 | 496 | 526 | mutABCG2 | Garcia-Escarp et al, 2004; Alqawi et al, 2004; Dogan et al, 2004, Lamy et al, 2995; Robey et al, 2001 |
| | | | MRP | Yeheskely-Hayon et al, 2009 |
| | | | | Elliott et al, 2004 |
| Rhodamine 800 | | | Pgp/ABCB1 | Frey et al, 1995 |
| Oxazine 1 | | | Pgp/ABCB1 | Frey et al, 1995 |
| Pheophorbide A | 415 | 673 | ABCG2 | Jonker et al, 2002; Robey et al, 2004 |
| SNARF-1 (5(6)-carboxyl seminaphthorhodafluor) | | | MRP1 | Jin & Jones, 2009 |
| SYTO13 | | | mutABCG2 | Garcia-Escarp et al, 2004 |
| SYTO16 | | | Pgp | Broxterman et al, 1997b |
| SY-38 | | | Pgp/ABCB1 | Frey T et al, 1995 |
| SY-3150 | | | Pgp/ABCB1 | Frey et al, 1995 |
| Thiazole Blue | | | Pgp/ABCB1 | Frey T et al, 1995 |
| Thiazole Orange | | | Pgp/ABCB1 | Frey T et al, 1995 |
| Tetramethylrhodamine Methyl Ester (TMRM) | 563 | 583 | MRP1 | Yeheskely-Hayon et al, 2009 |
| Oxazole Yellow | | | Pgp/ABCB1 | Frey T et al, 1995 |

TO FIG. 5-2

FROM
FIG. 6-1
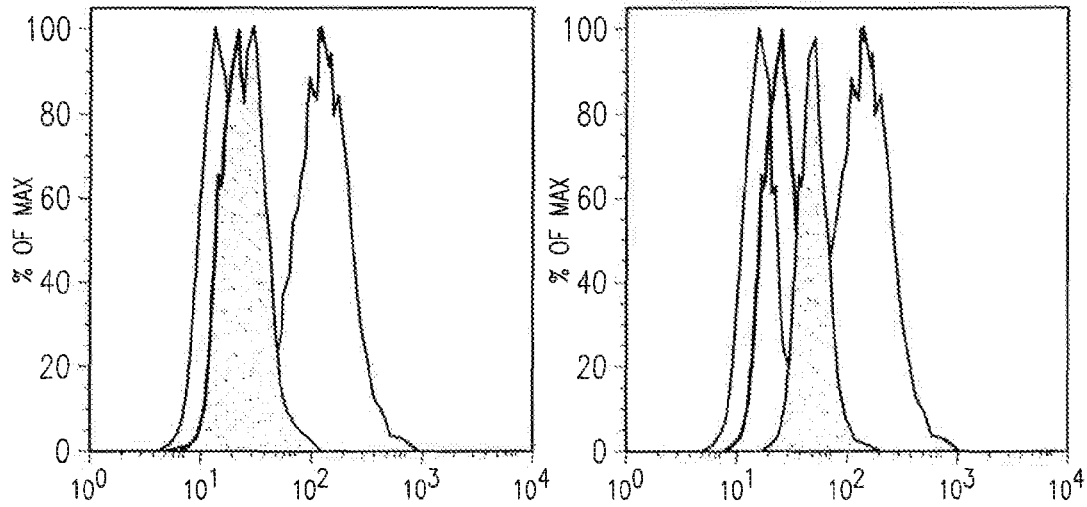
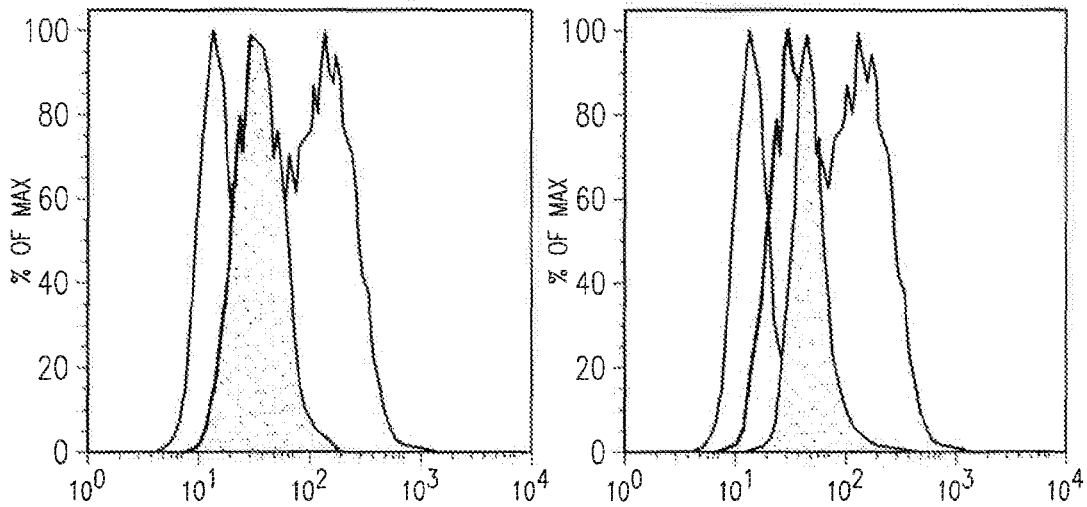
FIG. 6-2

TO FIG. 7A-2

FROM

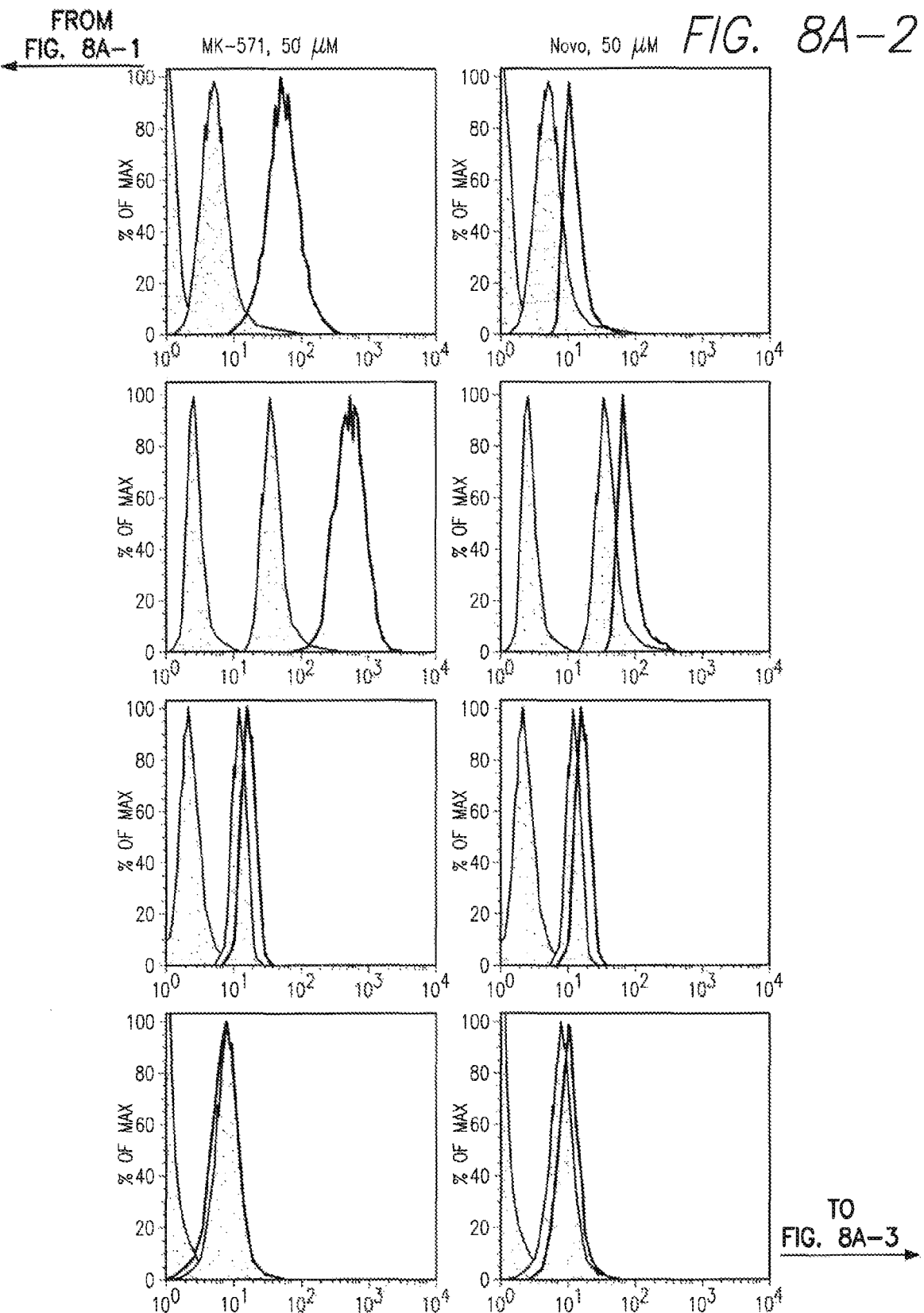

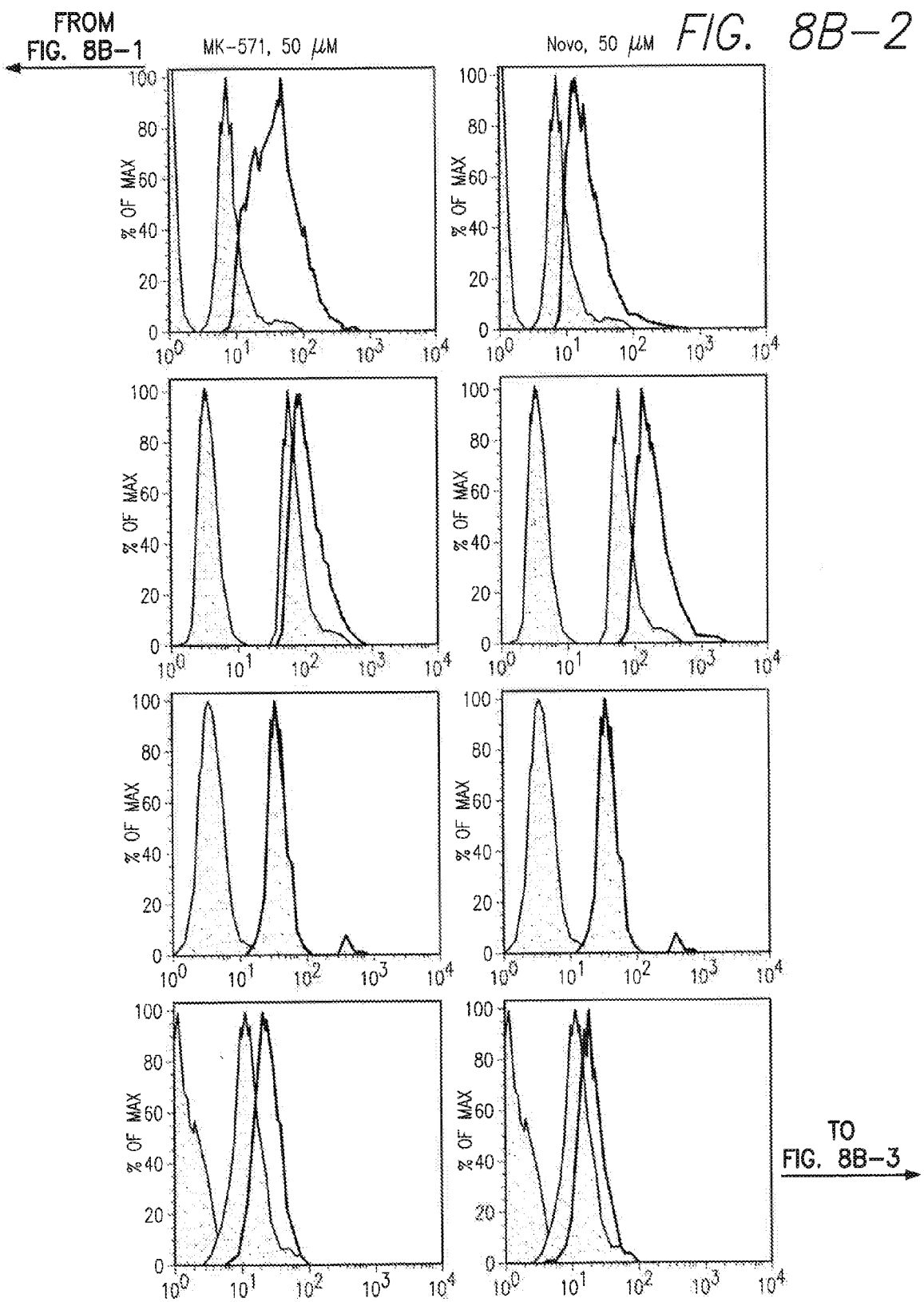

TO

TO

PROCESSES AND KITS FOR DETERMINING MULTI-DRUG RESISTANCE OF CELLS

FIELD OF THE INVENTION

This invention relates to the field of multi-drug resistance (MDR) in cells, and in tissues, organs and organisms containing such cells. This invention also relates to the use of certain xanthene compounds in MDR directed to, among other applications: determining drug resistance of cells, detecting and profiling multidrug resistant phenotypes in cells of interest, determining activity levels of membrane transporters involved in drug resistance, and determining the effect of test compounds on membrane transport by such membrane transporters.

All patents, patent applications, patent publications, scientific articles and the like, cited or identified in this application are hereby incorporated by reference in their entirety in order to describe more fully the state of the art to which the present invention pertains.

BACKGROUND OF THE INVENTION

Multidrug resistance relates to resistance of tumor cells to a whole range of chemotherapy drugs with different structures and cellular targets [Leonard et al., The Oncologist 8:411-424 (2003)]. The phenomenon of multi drug resistance (MDR) is a well known problem in oncology and thus warrants profound consideration in considering various cancer treatments. One of the underlying molecular rationales for MDR is the up-regulation of a family of MDR transporter proteins that cause chemotherapy resistance in cancer by actively extruding a large variety of therapeutic compounds from the malignant cells. MDR transporters belong to the evolutionarily conserved family of the ATP binding cassette (ABC) proteins, and are presented in practically all living organisms from prokaryotes to mammals [Gottesman et al., Nat Rev Cancer 2:48-58 (2002)]. ABC transporters play an important protective function against toxic compounds in a variety of cells and tissues, especially in secretory organs, at the sites of absorption, and at blood-tissue barriers. The three major multidrug resistance ABC proteins are MDR1 (including P-glycoprotein, ABCB1), multidrug resistance associated protein 1 (including MRP1, ABCC1) and ABCG2 (including placenta-specific ABC transporter, ABCP/breast cancer resistance protein, BCRP/mitoxantrone resistance protein and MXR). MDR1 and MRP1 can transport a large variety of hydrophobic drugs, and MRP1 can also extrude anionic drugs or drug conjugates. Other members of the MRP/ABCC family have also been indicated to be involved in cancer multidrug resistance (for details, see [Haimeur et al., Curr Drug Metab 5:21-53 (2004)]). The transport properties of ABCG2 are overlapping with those of both MDR1 and the MRP type proteins; thus these three proteins form a special network in chemo-defense mechanisms.

Because of a significant role that ABC transporters play in cancer multidrug resistance and the body's protection against xenobiotics, sensitive and specific quantitative assays are required for the detection of the activity of these proteins. High throughput assay systems are also required to screen for potential transporter-interacting partners. The estimation of the activity of ABC transporter is not easily achieved by the routinely available classical non-functional methods, such as Northern blotting, RNase protection, RNA in situ hybridization, RT PCR or immunostaining. MDR-ABC protein expression is often not correlated with mRNA levels or is often below the detection threshold, as relatively few active transporter molecules may cause major alterations in drug transport. Additionally, functional activity of ABC transporters may not correlate with their expression levels determined by the foregoing methods.

The ability of ABC transporters to actively transport compounds against the concentration gradient across the cell membrane has allowed the development of a number of functional assays to measure the level and function of transporter protein. Lipophilic dyes are capable of diffusing across cell membranes. Upon the loading of the cells with the dye(s), the resulting fluorescence intensity will depend on the activity of ABC transporters; the cells with highly active transporters will demonstrate lower fluorescence because of the increased efflux of the dye/substrate. The functions of MDR-ABC transporters have been characterized by measuring the cellular uptake, efflux, or steady-state distribution of a number of fluorescent substrates (summarized in Table 1, FIG. 1) using flow cytometry, fluorescent microscopy or fluorimetry. Substrate specificities of Pgp, MRP and BCRP are distinct, but also overlapping [Litman et al., Cell Mol Life Sci. 58:931-959 (2001)], as shown in Table 1, FIG. 1.

Several drawbacks have been noted relating to the sensitivity of most fluorophores used in this application because of protein binding, sequestration, or changes in fluorescence due to the intracellular milieu such as pH or free calcium levels [Hollo et al., Biochem Piophys Acta 1191:384-388 (1994)]. To increase sensitivity of the method, hydrophobic ester derivatives, such as AM esters of the fluorescent dyes have been used. These cell permeable derivatives of fluorescent dyes are also actively exported from cells by MDR proteins. When these ester derivatives reach the cytosol, however, intracellular esterases cleave the ester groups so that the dyes are now impermeable and require active transport. The resulting free dye can now be actively exported by MDR proteins in the cells [Homolya et al., J Biol. Chem. 268:21493-21496 (1993); Liming a et al., Exp Cell Res. 212:291-296 (1994)]. Some of the dyes are only fluorescent after AM hydrolysis.

Clinicians are especially interested in identifying the drug resistance profile, and the substrate specificity and drug extrusion activity of the various multi-drug resistance proteins expressed in a given tumor sample. The demonstration of the transport activity of various multi-drug resistance proteins in the plasma membrane requires a sensitive and reproducible in vitro multi-drug resistance assay. To date, BCRP has gained prominence as one of the three major ATP-binding cassette (ABC) membrane efflux transporters alongside P-gp and MRP, conferring drug resistance in cancer and inflammation chemotherapies [Litman et al., J Cell Sci. 113:2011-2021 (2000); van der Heijden et al., Arthritis Rheum. 60:669-677 (2009); Koshiba et al., Xenobiotica 38:863-868 (2008)]. Besides being present in drug-resistant cancer and T-cells, BCRP is also endogenously expressed at a high level in human placenta and to a lesser extent in liver, small intestine and colon, ovary, veins, capillaries, kidney, adrenal, and lung, with little to no expression in brain, heart, stomach, prostate, spleen, and cervix [Doyle et al., Oncogene 22(47):7340-7358 (2003)]. It has been demonstrated that calcein AM is useful for the quantitative functional analysis of the presence of active ABCB and ABCC but not ABCG transporters in cells Litman et al., J Cell Sci. 113:2011-2021 (2000)]. Thus, it is important to have a simple, reproducible and sensitive method to determine activity of all three types of ABC transporters in live cells.

To detect functional activity of drug efflux pumps, two assays using fluorescent dyes are commonly employed: one measures cellular dye accumulation and the other measures dye retention. The accumulation assay measures dye uptake in the presence or absence of known pump modulators. In the retention assay, the cells are loaded with the substrate in the absence of any reversal agent, washed, and then further incubated without dye but in the presence of reversing agents to allow time for the substrate to be transported out of the cell by a drug efflux pump. The distinction between accumulation and retention is necessary when evaluating cells for MDR phenotypes, as substrates act differently under different experimental conditions. Accumulation/retention assays offer high throughput, generic readouts (increase in fluorescence intensity), and are readily automated. These assays are not designed, however, to distinguish Pgp substrates from inhibitors [Tiberqhien, F. and Loor, F., Anticancer Drugs 7:568-578 (1996)] and do not directly measure transport.

The cell-based bidirectional permeability assay (or monolayer efflux assay) is currently accepted as the "method of choice" for determining the P-gp inhibition potential of test compounds in drug discovery laboratories and across the industry [Horio et al., J Biol. Chem. 264:14880-14884 (1989); Horio et al., Proc Natl Acad Sci USA. 85:3580-3584 (1988); Polli et al., J Pharmacol Exp Ther. 299:620-628 (2001); Rautio et al., Drug Metab Dispos 34(5) 786-792 (2006)]. The FDA guidance document [Drug Guidance for Industry, www.fda.gov/cder/guidance/6695dft.pdf, (2006)] also recommends conducting bidirectional permeability studies using Caco-2 cells or other cell lines (e.g., MDCK, LLC-PK1 etc.), either wild-type or transfected (with P-gp or other MDR proteins), to determine the P-gp inhibition potential of test compounds [Zhang et al., Xenobiotica 38:709-724 (2008)]. The experimental protocol for this assay is well established and quite uniform across different laboratories. Typically, bidirectional permeability of a well accepted MDR substrate is assessed alone and in the presence of a single concentration of test compound to estimate the inhibition potential.

This type of the assay is generally conducted for studying in vitro drug interactions with membrane transporter proteins that belong to two major superfamilies—ABC transporters [rev. in Schinkel, A. H. and Jonker, J. W., Adv Drug Deli Rev. 55:3-29 (2003)] and solute carrier (SLC) transporters [rev. in Hediger et al., Pflugers Arch. 447:465-468 (2004)]. Many pharmaceutical agents and toxins are transported by multi-specific SLC transporters for organic anions (e.g., OATP-SLCO/SLC21 and OAT-SLC22A1-3) and organic cations (OCT-SLC 22A4-5). These solute carriers, often called "uptake transporters," include a large variety of related membrane proteins, and in many cases possess overlapping substrate profiles with the MDR-ABC proteins [Marzolini et al., Pharmacogenomics 5:273-282 (2004); Miyazaki et al., Trends Pharmacol Sci 25:654-662 (2004)]. Some of these transporters perform obligatory exchange of organic compounds (e.g., OAT3), while in others transport is modulated and/or driven by monovalent ions and the membrane potential (e.g., OCTN). Moreover, there is a coordinated expression pattern for various SLC and ABC transporters in the liver, kidney, and BBB, which may govern the overall vectorial transport of many compounds that are mutual substrates of MDR-ABC and SLC proteins [Kusuhara, H. and Sugiyama, Y., Neuro Rx 2:73-85 (2005)].

Transepithelial transport depends on the polar distribution of proteins and lipids in the plasma membrane of epithelial cells. Typically, one plasma membrane contains a transporter that allows a specific ligand to enter the epithelial cells, and the plasma membrane on the opposite side of the cell contains a transporter that functions to export the ligand from the cell, resulting in net transepithelial transport of the ligand from one side of the epithelium to the other. In general, the substrates for transport by MDR proteins are highly lipophilic, and so enter epithelial cells freely from both surfaces. MDR proteins in the apical plasma membrane could expel substrates across the apical plasma membrane. Thus, ligand entering the cell from the basolateral surface is likely to leave the cell across the apical plasma membrane, whereas ligand entering the cell across the apical plasma membrane is likely to leave the cell across the same plasma membrane, with the result that basolateral to apical flux exceeds apical to basolateral flux. The net effect would be secretion of cytotoxic drugs by each of the epithelia listed above.

The monolayer efflux assay, where the ratio of basolateral-to-apical (B→A) permeability versus apical-to-basolateral (A→B) permeability is compared with a value of 1, is regarded as the standard for identifying MDR substrates because this assay measures efflux in the most direct manner [Polli et al., J Pharmacol Exp Ther 299:620-628 (2001)]. Due to concentration-dependent inhibition of active efflux on the apical side by MDR inhibitors, the B→A permeability decreases whilst A→B permeability increases with ratio approaching unity as the dose of inhibitor increases. The affinity of inhibitor to MDR protein(s) may be studied by calculating the active flux that can be obtained from the B→A fluxes in the absence and presence of MDR inhibitors. Inhibition potency, determined by inhibitor concentration-dependent transport assay, is usually represented as an $IC_{50}$ value, the concentration that gives 50% of maximum inhibition of a known P-gp substrate. Specificity of the inhibitor to P-gp may be determined by competitive assays, which involve a transport assay of a known substrate in the presence of known inhibitors (specific to various transporters) with and without compounds under test. Thus, appropriate design of competitive inhibition assays using known selected substrates and modulators will show the specificity of the inhibitors towards the efflux pump.

Bacterial multidrug efflux systems are a serious problem in the pharmacological treatment of patients with infectious diseases since the substrate spectra of many multidrug transporters include clinically relevant antibiotics [Putman et al., Microbiol Mol Biol Rev. 64(4):672-693 (2000)]. Multidrug resistant pumps operate via an active efflux mechanism and are typically ATP- or PMF- (proton motive force) dependent. Multidrug transporters are associated with both intrinsic and acquired resistance to antibiotics. For example, homologous to human P-gp ABC-type multidrug transporter LmrA of *L. lactis* displays very broad antibiotic specificity, demonstrating that ATP-dependent multidrug transporters can seriously affect the efficacy of many antibiotics [van Veen et al., Proc Natl Acad Sci ISA 93:10668-10672 (1996); van Veen et al., Nature 391(6664):291-295 (1998)]. Dyes such as acriflavine, ethidium bromide, rhodamine 6G and pyronin Y are used as substrates for many bacterial efflux pumps and their susceptibility in the presence or absence of efflux pump inhibitors has been used as a screen for the presence of efflux-related resistance mechanisms [DeMarco et al., Antimicrob Agents Chemother. 51:3235-3239 (2007)]. The bacterial multidrug efflux systems transport similar drugs and are sensitive to similar inhibitors as the mammalian multidrug transporter, P-gp [Neyfakh et al., Proc Natl Acad Sci USA. 88:4781-4785 (1991)].

There remains a need for a general non-toxic MDR probe that a) will recognize all three major ABC transporter's types in live cells (unlike the most common MDR probe Calcein AM and other calcium indicator dyes such as Fluo-3 and Fluo-4); b) will be brighter (e.g. possess higher quantum yield and molar extinction coefficient) and more sensitive than common general MDR probes, such as doxorubicin and mitoxantrone; c) could be used in all types of the efflux assays discussed above; d) will require few processing steps and provide a reproducible protocol; and e) will be compatible with other common fluorescent dyes used in flow cytometry and diverse fluorescent proteins expressed in cells.

SUMMARY OF THE INVENTION

This invention relates to a process for determining drug resistance of cells of interest comprising the first step (A) of providing: (i) a clinical or biological sample comprising cells; (ii) at least one xanthene compound that is transportable across a cell membrane by membrane transporters: MDR1, MRP and BCRP; and (iii) one or more membrane transporter inhibitors. In step (B), cells from a first portion of the clinical or biological sample (i) are contacted with at least one xanthene compound (ii) while in step (C), cells from a second portion of the clinical or biological sample (i) are contacted with at least one xanthene compound (ii) and one or more inhibitors (iii). The fluorescent signals generated in steps (B) and (C) are then measured in step (D). By comparing the fluorescent signals measured in step (D), the elevated activities of MDR1, MRP and BCRP, or a combination thereof, are determined, thereby determining the drug resistance of the cells of interest.

This invention also relates to a process for determining drug resistance of cells of interest. In this process, the following are provided in step (A): (i) at least three portions of a clinical or biological sample comprising cells; (ii) at least one xanthene compound that is transportable across a cell membrane by membrane transporters: MDR1, MRP and BCRP; and (iii) one or more membrane transporter inhibitors. Three contacting steps are carried out. In step (B), cells from a first portion of the clinical or biological sample (i) are contacted with at least one xanthene compound (ii) under conditions sufficient to inhibit efflux of the xanthene compound or compounds from the cells. In step (C), cells from a second portion of the clinical or biological sample (i) are contacted with at least one xanthene compound (ii) under conditions sufficient to permit efflux of the xanthene compound or compounds from the cells. In step (D), cells from a third portion of the clinical or biological sample (i) are contacted with at least one xanthene compound (ii) and one or more inhibitors (iii). The fluorescent signals generated in steps (B), (C) and D is then measured in step (E). The fluorescent signals measured in step (D) are then compared in step (F), to determine elevated activities of said MDR1, MRP and BCRP, or a combination thereof, thereby determining the drug resistance of the cells of interest.

This invention also provides a process for determining the effect of a test compound on transport across a cell membrane by the membrane transporters: MDR1, MRP and/or BCRP. In this process, three components are provided in step (A): (i) a clinical or biological sample comprising cells; (ii) at least one xanthene compound that is transportable across a cell membrane by membrane transporters: MDR1, MRP and BCRP; and (iii) one or more test compounds. Two contacting steps are then carried out. These include step (B) of contacting cells from a first portion of the clinical or biological sample (i) with at least one xanthene compound (ii). In step (C), cells from a second portion of the clinical or biological sample (i) are contacted with at least one xanthene compound (ii) and one or more test compounds (iii). The fluorescent signals generated in step (B) and step (C) are measured in step (D). The measured fluorescent signals are then compared in step (E) to determine elevated activities of MDR1, MRP and BCRP, or a combination thereof, thereby determining the effect of the one or more test compounds (iii) on cell membrane transport by the membrane transporters.

The present also provides a process for determining the effect of a test compound on transport across a cell membrane by the membrane transporters: MDR1, MRP and/or BCRP. In step (A) of this process, there are provided (i) at least three portions of a clinical or biological sample comprising cells; (ii) at least one xanthene compound that is transportable across a cell membrane by membrane transporters: MDR1, MRP and BCRP; and (iii) one or more membrane transporter inhibitors. Three contacting steps are then carried out, including step (B) of contacting cells from a first portion of the clinical or biological sample (i) with at least one xanthene compound under conditions sufficient to inhibit efflux of the xanthene compound or compounds from the cells. In a second contacting step, cells from a second portion of the clinical or biological sample (i) are contacted with at least one xanthene compound (ii) under conditions sufficient to permit efflux of the xanthene compound or compounds from the cells. In the third contacting step, cells from a third portion of the clinical or biological sample (i) are contacted with at least one xanthene compound (ii) and one or more inhibitors (iii). In step (E), the fluorescent signals generated in steps (B), (C) and D are measured. The measured fluorescent signals are compared in step (F) to determine elevated activities of MDR1, MRP and BCRP, or a combination thereof, thereby determining the drug resistance of the cells of interest.

This invention additionally provides a kit for determining drug resistance of cells of interest, or detecting and profiling multidrug resistant phenotypes in cells of interest, or determining activity levels of membrane transporters MDR1, MRP and BCRP. The kit comprises in packaged combination: (i) at least one xanthene compound that is transportable across a cell membrane by membrane transporters: MDR1, MRP and BCRP; (ii) one or more membrane transporter inhibitors; and (iii) instructions therefor.

BRIEF DESCRIPTION OF THE FIGURES

FIG. 7 shows results comparing performance of two fluorescent probes (Fluo-8™ and Rhod-4™ dyes) against Calcein AM.

FIG. 8 are results of MDR tests with four different inhibitors comparing Rhod-4™ dye and Fluo-8™ against Doxorubicin and Mitoxantrone.

FIG. 9 illustrate results of MDR tests with four different inhibitors comparing Fluo-8™ and Rhod-4™ against Calcein AM.

DESCRIPTION OF THE INVENTION

Figure 2:
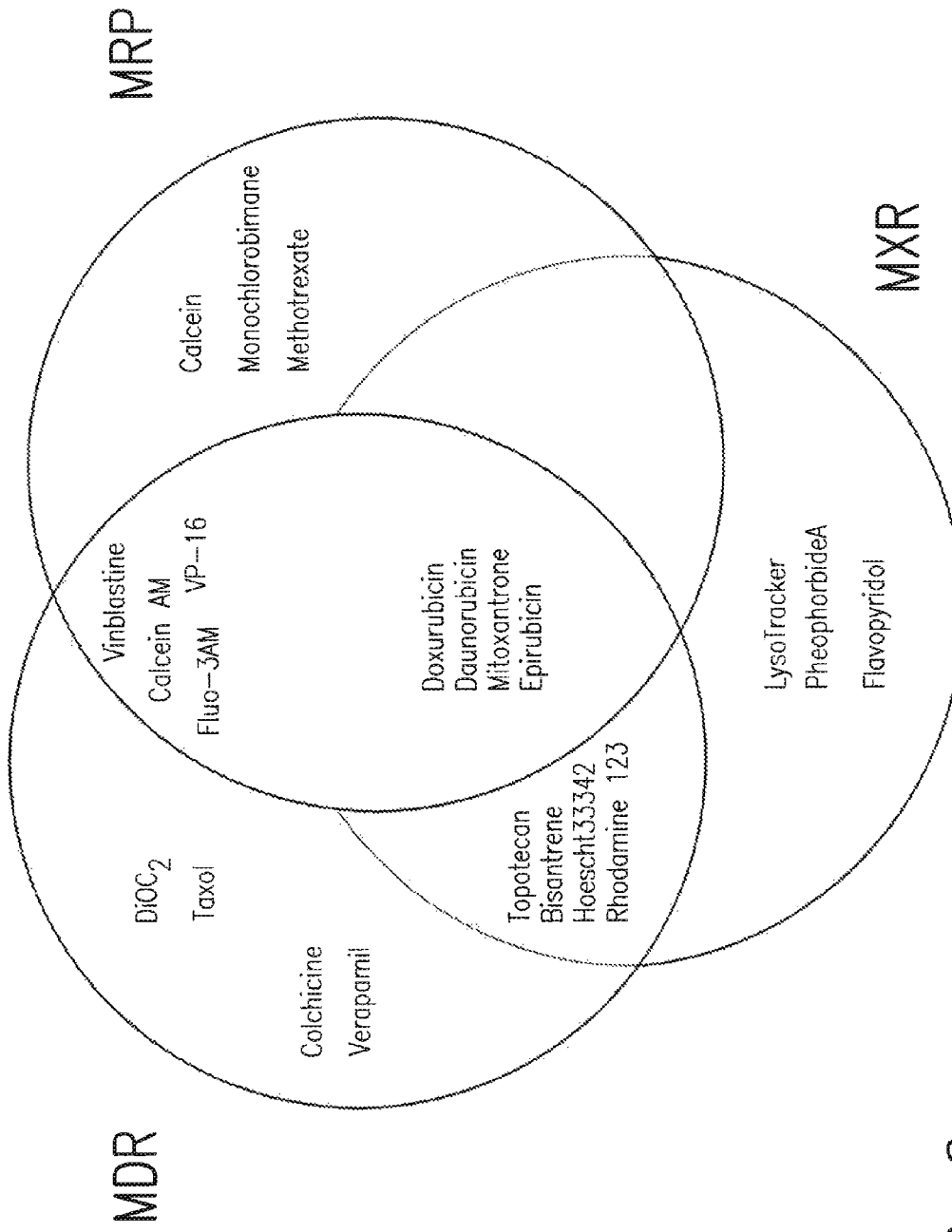
FIG. 2 is a Venn diagram of fluorescent substrates used for studying MDR-ABC transporter functions.
Figure 3A:
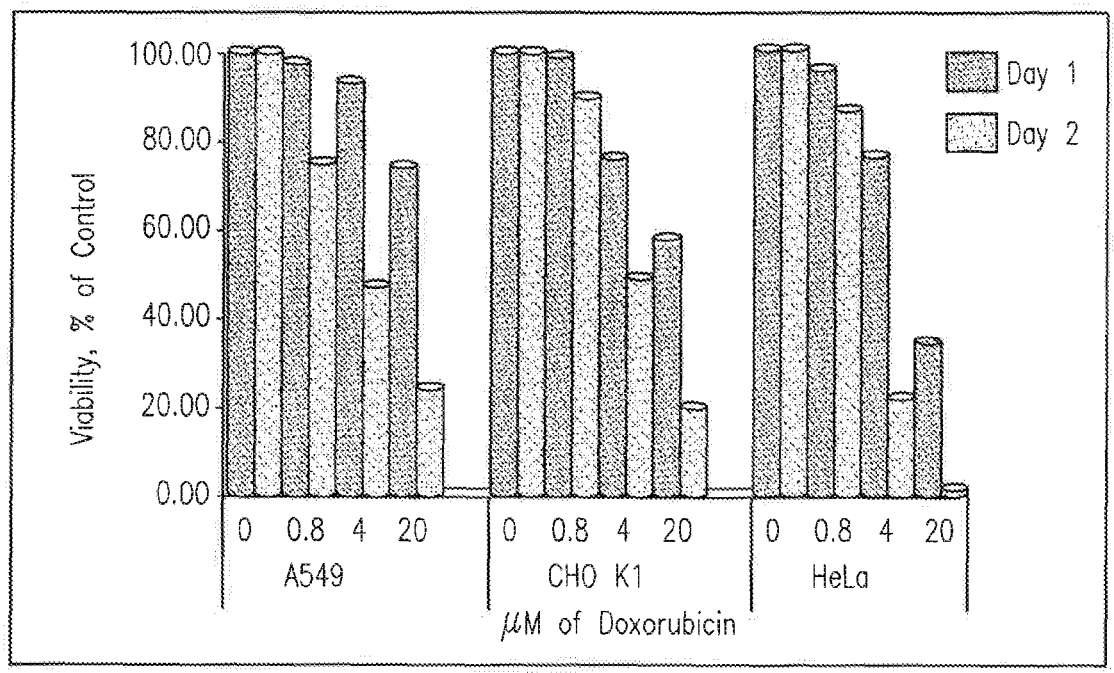
FIG. 3 are bar graphs of MDR-related chemoresistance of CHO K1 and A549 cell lines toward Doxorubicin (FIG. 3A), Taxol (FIG. 3B), Vincristine (FIG. 3C) and Mitoxantrone (FIG. 3D).
Figure 3B:
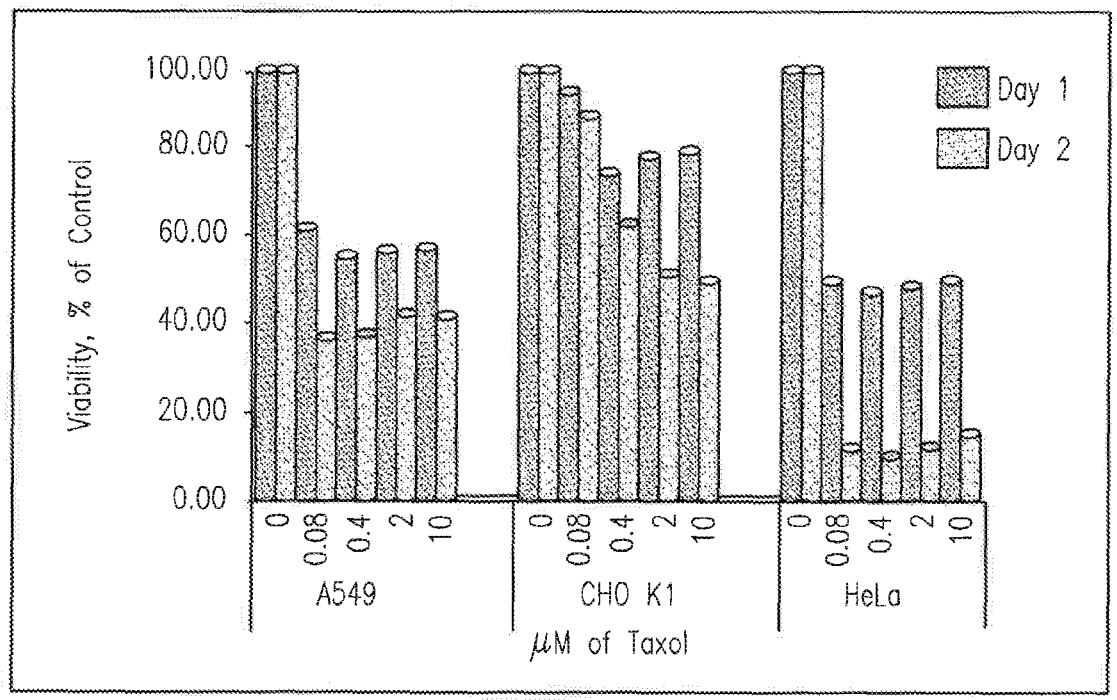
Figure 3C:
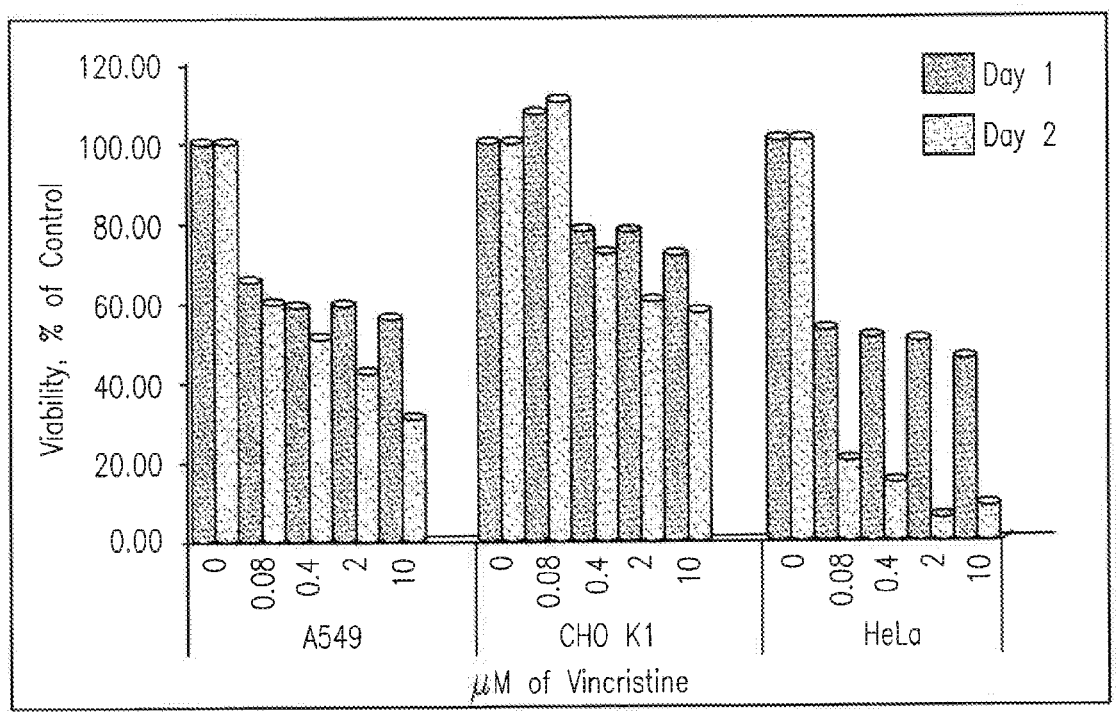
Figure 3D:
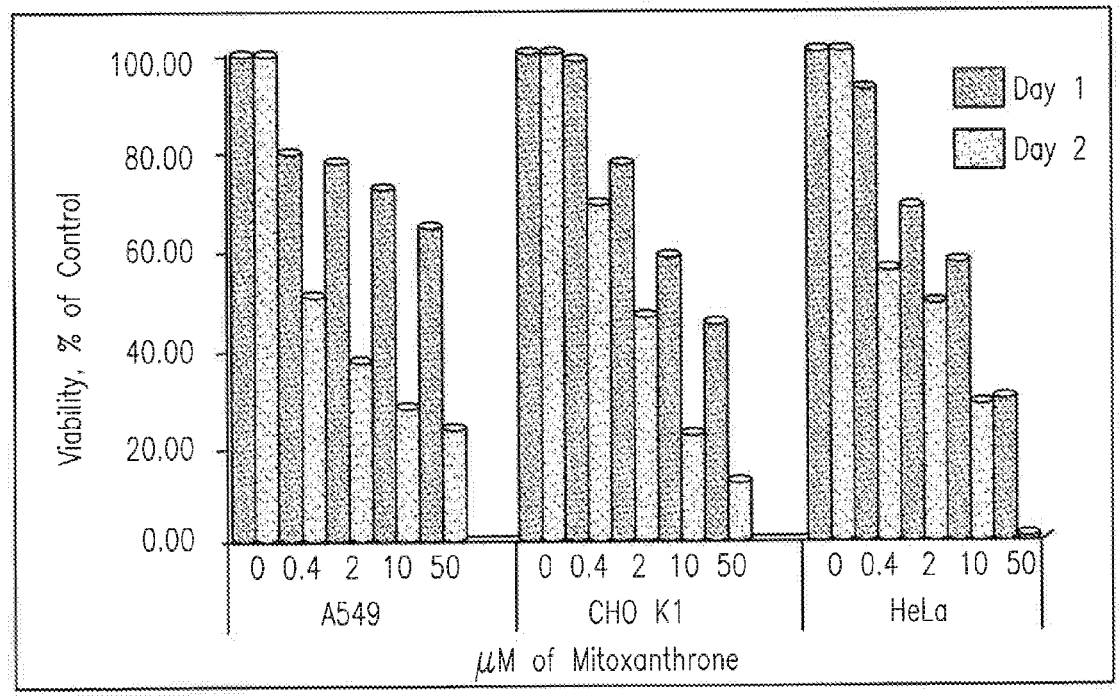
Figure 4:
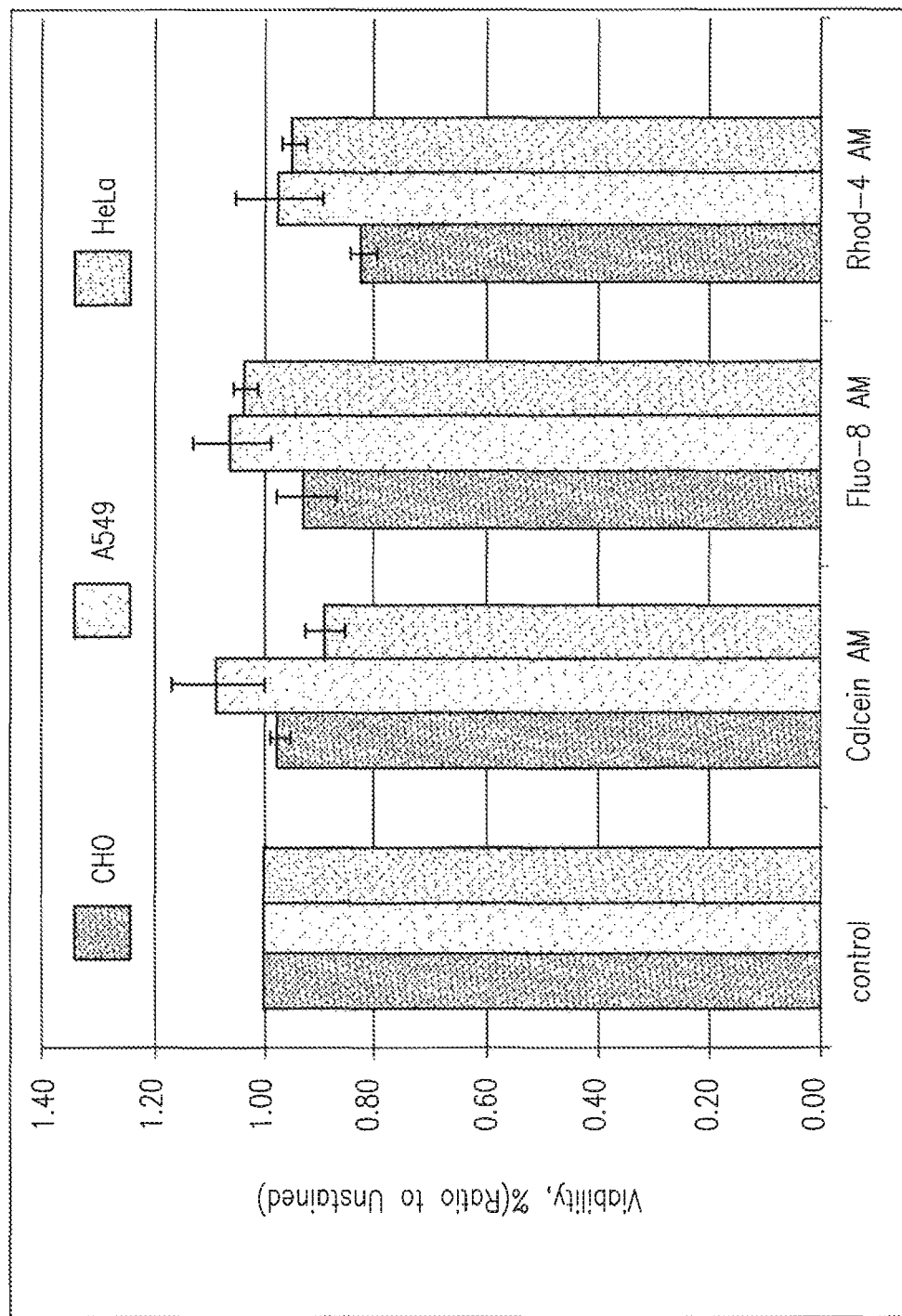
FIG. 4 depicts results of an MDR assay and toxicity in cells treated with two fluorescent probes (Fluo-8™ and Rhod-4™).

As described above, the three major multidrug resistance ABC proteins are MDR1 (including P-glycoprotein, ABCB1), multidrug resistance associated protein 1 (including MRP1, ABCC1) and ABCG2 (including placenta-specific ABC transporter, ABCP/breast cancer resistance protein, BCRP/mitoxantrone resistance protein and MXR). MDR1 and MRP1 can transport a large variety of hydrophobic drugs, and MRP1 can also extrude anionic drugs or drug conjugates. Other members of the MRP/ABCC family have also been indicated to be involved in cancer multidrug resistance (for details, see [Haimeur et al., Curr Drug Metab 5:21-53 (2004)]). The transport properties of ABCG2 are overlapping with those of both MDR1 and the MRP type proteins; thus these three proteins form a special network in chemo-defense mechanisms (see Table 2 below).

washing steps, thus being time- and effort consuming. It is demonstrated that the washing step is optional when employing Fluo-8™ AM and Rhod-4™ AM and may be omitted from both uptake and efflux protocols to simplify the assay and make it more user-friendly. If a large number of samples is to be analyzed, however, the excess of dye should be washed away and samples kept on ice until the measurement is performed. Otherwise, samples would have to be analyzed in small batches to avoid artifactual measurements.

Acetate or acetoxy methyl ester (AM) derivatives of Fluo-8™ and Rhod-4™ dyes demonstrate fast internalization, favorable uptake/efflux kinetics and much better sensitivity than commonly used fluorescent substrates of general specificity (such as doxorubicin and mitoxantrone).

With appropriate compensation correction, both probes can be used in combination with propidium iodide or 7-amino-actinomycin D, the common viability dyes

TABLE 1

Substrate and inhibitor specificity of the major multidrug resistance proteins that belong to the ABC transporter family

| MDR Protein | Gene subfamily | Substrates of the protein | Reversal Agents* | Probes for Detection* |
|---|---|---|---|---|
| Pgp | Mdr1/ABCB | Anthracyclines (DOX, DNR), colchicines, vinca alkaloids, etoposide, taxanes | Verapamil, CsA, reserpine, CsD, quinoline, PK11195 | DiOC$_2$(3), Rho 123, DOX, Calcein AM, JC-1 |
| MRP | MRP/ABCC | Anthracyclines (DOX, DNR), camptothecin, vinca alkaloids, methotrexate, etoposide, NOT TAXANES | Genistein, flavopyridol, probenecid, MK-571, CsA | Fluo-3, DOX, DNR, Calcein AM, SNARF, |
| BCRP | ABCG | Anthracyclines (DOX, DNR), mitoxantrone, topotecan, flavopyridol, methotrexate, NOT vinca alkaloids, taxanes | Fumitremorgin, Novobiocin, Ko134, GF120918, Genistein, CsA, reserpine, tamoxifen, flavopiridol | Rho123, JC-1, Mxt, DNR, BODIPY-prazozin, bisantrene, Hoechst 33342, LysotrackerGreen |

Dyes have been previously described for MDR detection. Many of these are listed in Table 1, FIG. 1.

The present invention relates to functional detection of multidrug resistant phenotypes in live cells (both suspension and adherent) by measuring the active dye efflux mediated by different ABC transporter proteins using flow cytometry, microplate fluorimetry and/or other device capable of detecting a fluorescence signal.

The suggested application presents a new use for the calcium indicators as described in U.S. Patent Application Publication No. 2008/0254498 A1 (hereby incorporated by reference), in particular Fluo-8™ AM and Rhod-4™ AM (now commercially available from AAT Bioquest) and also offers important advantages over existing functional dye efflux/uptake assays. Unlike the most common MDR probe, Calcein AM, and unlike other calcium indicators such as Fluo-3™ and Fluo-4™, Fluo-8™ AM and Rhod-4™ AM are capable of detection and distinguishing between all three of the major types of ABC transporters in live cells.

The described application offers a quick, reproducible, specific and relatively simple way for functional detection of ABC transporter proteins that allow high-volume specimen throughput and employs widely available instrumentation. Standard dye uptake and dye efflux protocols include several employed in flow cytometry. Moreover, their spectral characteristics are compatible with common dyes used in multicolor flow cytometry experiments (such as phycoerythrin), and with different fluorescent proteins such as green fluorescent and red fluorescent proteins (GFP and RFP).

Assays disclosed herein are high-throughput in the sense that these assays may be carried out in a 96-well or higher density format (e.g., 384- or 1536-well plates). Desirably, such assays demonstrate a signal of sufficient intensity that it can be easily measured from a microtiter plate in low volume and have a suitable signal-to-noise ratio and CV determined from the measurements across the entire plate (statistical parameter, Z', which has an acceptable lower limit of 0.5).

The MDR probes suggested in the present application should also be compatible with clinical samples (both blood and solid tissues), bacterial samples and transwell type of cellular assays.

Fluo-8™ AM and Rhod-4™ AM probes demonstrate performance similar to or better than Calcein AM regarding pH independence and can be used in an operational range of pH 6.0 to 8.0. Despite being calcium indicators, differences in fluorescence intensities of MDR probes Fluo-8™ AM and Rhod-4™ AM in the proposed protocol are solely dependent upon the presence of the ABC transporters and do not depend upon the intracellular $Ca^{2+}$ concentration (similarly to Calcein™ AM).

It should be appreciated by those skilled in the art that rather than being exclusively confined to Fluo-8™ AM and Rhod-4™ AM, any compound can be employed in the method of the invention that meets the following criteria: it is cell permeable; it is a good substrate for all the three MDR proteins; it gets transformed in the cell by generally present enzymes to a signal generating compound and accumulates within the cell. All those considerations are part of this invention.

DEFINITIONS

By multidrug resistance (MDR) is meant the occurrence of transport protein-mediated cell efflux in a cell(s). Since such a cell efflux typically transports a variety of substances (including chemotherapy drugs) to the outside of the cell membrane, it interferes with the cancer chemotherapy. Tumor cells demonstrating such an efflux are termed "multi-drug resistant"

By fluorophore is meant a component of a molecule which causes a molecule to be fluorescent.

By fluorogenic is meant a process by which fluorescence is generated. In the context of analytical assays, the term refers to a chemical reaction dependent on the presence of a particular analyte that produces fluorescent molecules.

By "MDR probe" is meant an entity, be it a small organic fluorophore, a fluorescent protein, a nanoparticle or a quantum dot, that is useful for monitoring an active and effective transport of a variety of compounds to the exterior of the cell membrane, by one or more transport proteins that are typically over-expressed in the cell.

By "ABC-transporter protein" or "membrane transporter" is meant a membrane bound protein that can transport a given compound through the cell membrane even against the concentration gradient by using the energy obtained through ATP hydrolysis.

By a "transport protein-mediated cell efflux" is meant the active and effective transport of a variety of compounds to the extracellular compartment of the cell, by one or more transport proteins that are typically over-expressed in the cell's plasma membrane.

By an "inhibitor of transport protein-mediated cell efflux" or "transport blocking agent" is meant a compound that can block the active transport of a compound of interest (e.g. Fluo-8™ AM or Rhod-4™ AM) to the outside of the cell membrane by any mechanism of action. A "general inhibitor of efflux" blocks all active transport to the outside of the cell membrane regardless of the type of transport protein expressed in the sample. A "selective inhibitor of efflux" blocks only that transport that is due to a selected transport protein or a selected transport-mediated efflux pathway.

By "MDR1 or P-glycoprotein" is meant a membrane bound protein of ~170 kDa molecular weight, functional expression of which causes multi-drug resistance of the given cell.

By "MRP or Multi-drug Resistance protein" is meant a ~190 kDa glycoprotein belonging to a family of ABC transporters, functional expression of which confers multi-drug resistance on a given cell by mediating the ATP-dependent membrane transport of glutathione S-conjugates of chemotherapeutic drugs.

By ABCP/MXR/BCRP protein is meant an ABC half-transporter which forms homodimers in the plasma membrane and actively extrudes a wide variety of chemically unrelated compounds from the cells and protects cells against various xenobiotics. This protein participates in stem-cell protection/regulation.

By "MDR activity" is meant the activity of a protein (or membrane transporter) that causes multi-drug resistance. i.e., the activity of an ABC transporter protein or membrane transporter protein.

By a "substrate of an MDR protein" or "substrate of a membrane transporter" is meant a compound that can be extruded from the cell through an MDR mediated active transport mechanism.

By a "cell permeable compound" is meant a usually hydrophobic compound that can enter the cell in a practically unconstrained manner.

By "clinical or biological sample" is meant such biological, clinical and even non-biological samples, including but not limited to blood, urine, feces, saliva, pus, semen, serum, cerebral spinal fluid (CSF) and any other tissue or organ samples, including biopsies.

Sensitivity

Cyclosporin A (noncompetitive broad-spectrum MDR modulator, 5 µM), verapamil (specific Pgp/ABCB1 subfamily inhibitor, 20 µM), probenecid, MK-571 (both are specific MRP/ABCC subfamily inhibitors, 0.2 mM and 50 µM correspondingly), novobiocin and fumitremorgin C (specific for BCRP/ABCG subfamily, 0.5 mM and 100 µM correspondingly) were used in all experiments unless specified differently. Concentrations of the modulators used in the experiments were non-toxic to the cells (based upon standard 3-(4,5-Dimethylthiazol-2-yl)-2,5-Diphenyltetrazolium Bromide (MTT) testing, data not shown). Fluo-8™ was used in all experiments at 5 µM, and Rhod-4™—at 4 µM final concentrations. Flow cytometry data were analyzed by comparison of median fluorescence or using Kolmogorov-Smirnov statistics [Young, J Histochem Cytochem 25:935-941 (1977)]

Kolmogorov-Smirnov statistics measures the difference between two distribution functions and generates a D value ranging between 0 and 1.0, with higher values indicating a greater difference between the distribution functions. The D value generated by the KS statistics was modified by ascribing a negative value if the fluorescence of a negative control (no inhibitor) was brighter than the fluorescence of the sample with inhibitor. The method was one of those recommended by the First International MDR1 Methods Detection Workshop (St. Jude Children's Research Hospital, Memphis, Tenn.).

KS values appear to be a reliable method for accurately measuring of MDR. Intensity staining was categorized as follows (for MRP detection using $DiOC_2(3)$ probe):

Bright (D≧0.30)
Moderate (0.20≦D≦0.30)
Dim (0.15≦D<0.20)
Negative (D<0.15)
Notably, D-values cut-points may vary slightly (about 10%) based upon staining different proteins with different dyes.

In various tables below, D-value for each protocol and each inhibitor were compared to MAF values (MDR Activity Factor) that were calculated using the following formula: $MAF=100*((MFI_{inh}-MFI_0)/MFI_{inh})$, where $MFI_{inh}$ and $MFI_0$ are mean fluorescence intensity values measured in the presence and absence of inhibitor. The cut-off values of MAF for Calcein AM that have been adopted in clinical assays are about 20-25.

This invention provides a process for determining drug resistance of cells of interest, the process comprising the steps of: (A) providing: (i) a clinical or biological sample comprising cells; (ii) at least one xanthene compound that is transportable across a cell membrane by membrane transporters: MDR1, MRP and BCRP; and (iii) one or more membrane transporter inhibitors; (B) contacting cells from a first portion of the clinical or biological sample (i) with at least one xanthene compound (ii); (C) contacting cells from a second portion of the clinical or biological sample (i) with at least one xanthene compound (ii) and one or more inhibitors (iii); (D) measuring fluorescent signals generated in step (B) and step (C); and (E) comparing the fluorescent signals measured in step (D) to determine elevated activities of MDR1, MRP and BCRP, or a combination thereof, thereby determining the drug resistance of the cells of interest.

This invention also provides a process for determining the effect of a test compound on transport across a cell membrane by the membrane transporters: MDR1, MRP and/or BCRP, the process comprising the steps of: (A) providing: (i) a clinical or biological sample comprising cells; (ii) at least one xanthene compound that is transportable across a cell membrane by membrane transporters: MDR1, MRP and BCRP; and (iii) one or more test compounds; (B) contacting cells from a first portion of the clinical or biological sample (i) with at least one xanthene compound (ii); (C) contacting cells from a second portion of the clinical or biological sample (i) with at least one xanthene compound (ii) and one or more test compounds (iii); (D) measuring fluorescent signals generated in step (B) and step (C); and (E) comparing the fluorescent signals measured in step (D) to determine elevated activities of said MDR1, MRP and BCRP, or a combination thereof, thereby determining the effect of the one or more test compounds (iii) on cell membrane transport by the membrane transporters.

Other aspects of this process are contemplated by the present invention including carrying out step (D) by measuring cellular uptake of the xanthene compound or compounds (ii). In step (A), the one or more inhibitors (iii) are provided in an amount sufficient to substantially prevent transport of the xanthene compound or compounds (ii) across a cell membrane by one or more of the membrane transporters MDR1, MRP and BCRP.

The xanthene compound (ii) may take a number of forms, including one where it has the structure

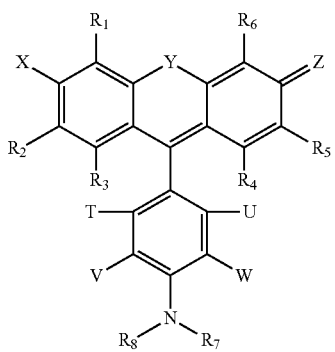

wherein $R^1$-$R^6$ are independently H, halogen, carboxy, alkoxy, aryloxy, thiol, alkylthiol, arylthiol, azido, nitro, nitroso, cyano, amino, hydroxy, phosphonyl, sulfonyl, carbonyl, boronic acid, aryl, or heteroaryl; or alkyl, or alkoxy, optionally substituted one or more times by halogen, amino, hydroxy, phosphonyl, sulfonyl, carbonyl, boronic acid, aryl or heteroaryl, wherein heteroatom Y is independently selected from O, S, Se, $NR^9$ and $CR.^{10}R^{11}$, wherein X is independently selected from $OR^{12}$, $NR^{12}R^{13}$ and Z is independently selected from O and $NR^{16}R^{17}$, where each $R^9$, $R^{10}$, $R^{11}$, $R^{12}$, $R^{13}$, $R^{16}$ and $R^{17}$ is independently H, an alkyl having 1-12 carbons, carboxyalkyl, substituted or non-substituted amino alkyl or alkylsulfonate, wherein T and U are independently selected from alkyl having 1-12 carbons, alkoxy having 1-12 carbons, aryloxy, amino, halogen, cyano, carboxy, carboxyalkyl, carbonyl, sulfonyl, phosphonyl, boronic acid, aryl, and heteroaryl, and wherein V and W are independently selected from $OR^{14}$, $SR^{15}$ or $NR^{12}R^{13}$, such that at least one of V or W, in combination with $NR^7R^8$, forms a metal chelator, where each $R^7$, $R^8$, and $R^{12}$-$R^{15}$ are independently H, an alkyl having 1-12 carbons, carboxyalkyl, alkoxy or aryloxy.

In another embodiment, the xanthene compound (ii) has the structure

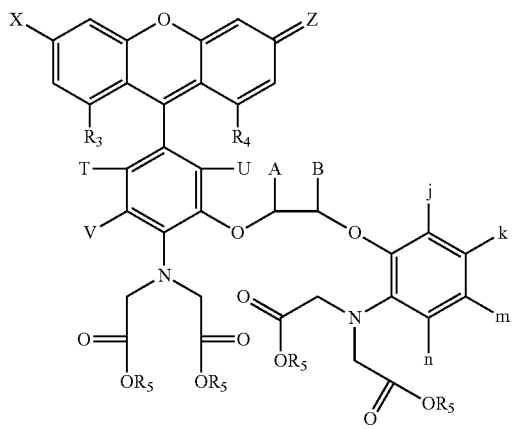

wherein A and B are independently hydrogen, alkyl, cycloalkyl, or aryl; or A and B taken in combination are cycloalkyl or aryl;

wherein $R^3$, $R^4$, j, k, m, n and V are independently hydrogen, halogen, carboxy, alkoxy, aryloxy, thiol, alkylthiol, arylthiol, azido, nitro, nitroso, cyano, amino, hydroxy, phosphonyl, sulfonyl, carbonyl, boronic acid, aryl, or heteroaryl; or alkyl, or alkoxy that is itself optionally substituted one or more times by halogen, amino, hydroxy, phosphonyl, sulfonyl, carbonyl, boronic acid, aryl or heteroaryl;

wherein each $R^5$ is independently hydrogen, alkyl having 1-9 carbons, acetoxymethyl, or a biologically compatible salt; and wherein T and U are independently hydrogen, alkyl having 1-12 carbons, alkoxy having 1-12 carbons, aryloxy, amino, halogen, cyano, carboxy, acetoxymethylcarbonyl, carboxyalkyl, carbonyl, sulfonyl, phosphonyl, boronic acid, aryl or heteroaryl; provided that at least one of T and U is not hydrogen.

In yet another embodiment, the xanthene compound (ii) has the structure

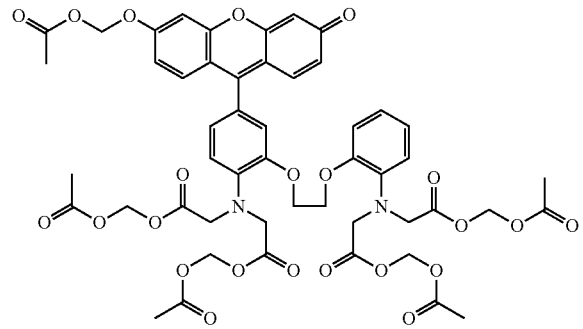

With regard to the membrane transporter inhibitors (iii), these may comprise general inhibitors, specific inhibitors or a combination of general inhibitors and specific inhibitors. Among general inhibitors are cyclosporin A, biricodar (VX-710), tariquidar (XR9576), plant polyphenols, curcumin, tRA98006 or imatinib mesylate and a combination of any of the foregoing.

Among specific inhibitors mention should be made of valspodar (PSC833), verapamil, vanadate, PAK-104P, MK-571, FTC, Ko134, Elacridar (GF 120918), novobiocin, probenecid, BIB-E, disulfuram, indomethacin, furocemide, Penicillin G, sulfinpirazole, laniquidar (R101933), zosuquidar (LY335979), ontogeny (ONT-093), isothiocyanates, phytoestrogens, TAG-139, flavenoids, MS-209, NSAIDs, mitotane (NSC-38271), PK11195, cyclosporine D, anthranilamide, pipecolinate, quinoline, OC-144-093, diallyl sulfide, amooranin, agosterol A, siRNA, rifampicin, amiodarone, quinidine, quinine, nifedipine, dexniguldipin, LY455776, V-104, tricyclic izoxazoles, pluronic L61, or fumitremorgin C and a combination of any of the foregoing.

The aforementioned inhibitors, both general and specific inhibitors are listed and described in terms of particular membrane transporter functions in Table 3 below:

TABLE 3

Specificity of MDR Inhibitors.

| Inhibitor | MDR1 | MRP1 | MRP2 | BCRP |
|---|---|---|---|---|
| Cyclosporine A | + | + | + | + |
| Valspodar (PSC833) | + | | + | |
| Verapamil | + | | | |
| Vanadate | + | | | |
| Biricodar (VX-710) | + | + | + | + |
| PAK-104P | + | + | + | |
| MK571 | | + | + | |
| FTC | | | | + |
| Ko143 | | | | + |
| Elacridar (GF120918) | + | | | + |
| Probenecid | | + | | |
| BIB-E | | | | + |
| Disulfiram | + | + | | |
| Indomethacin | | + | | |
| Furocemide | | + | | |
| Penicillin G | | + | | |
| Sulfinpirazole | | + | | |
| Laniquidar (R101933) | + | ? | ? | ? |
| Tariquidar (XR9576) | + | + | + | + |
| Zosuquidar (LY335979) | + | | | |
| Ontogen (ONT-093) | + | | | ? |
| Plant polyphenols | + | + | ? | + |
| Curcumin | + | + | ? | + |
| tRA98006 | + | + | + | + |
| Isothiocyanates | + | + | + | |
| Phytoestrogens | | | | + |
| TAG-139 | | | | + |
| Imatinib Mesylate | + | + | | + |
| flavonoids | + | | | + |
| MS-209 | + | + | | |
| NSAIDs | | + | | |
| NSC-38271 (mitotane) | + | | | |
| PK11195 | + | | | |
| Cyclosporine D | + | | | |
| Anthranilamide | + | | | |
| Pipecolinate | + | | | |
| Quinoline | + | | | |
| OC-144-093 | + | | | |
| Diallyl Sulfide | + | | | |
| Amooranin | + | | | |
| Agosterol A | + | + | | |
| siRNA | + | | | |
| Rifampicin | | + | | |
| Amiodarone | + | | | |
| Quinidine | + | + | | |
| Quinin | + | + | | |
| Nifedipine | + | | | |
| Dexniguldipin | + | | | |
| LY455776 | + | + | | |
| V-104 | + | + | | |
| Tricyclic Izoxazoles | | + | | |
| Pluronic L61 | + | | | |

In other aspects, at least one viability dye (iv) can be usefully provided in step (A). Among such viability dyes (iv) are those comprising propidium iodide, 7-amino-actinomycin D (7-AAD), DRAQ7™, membrane-impermeable form of Nuclear-ID™ Red, membrane-impermeable form of Nuclear-ID™ Green, SYTOX® Green, SYTOX® Orange, SYTOX® Blue, YOYO, TOTO or TO-PRO, or a compound having the structure:

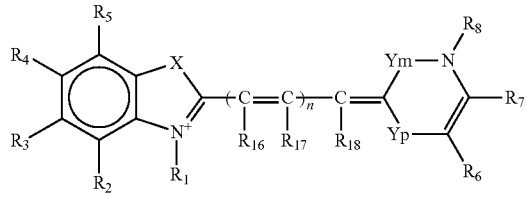

wherein X comprises $CR^{11}R^{12}$, $NR^{11}$, O, S or Se where $R^{11}$ and $R^{12}$ independently comprise hydrogen, a halogen, an amino group, an alkyl group wherein said alkyl group is saturated or unsaturated, linear or branched, substituted or unsubstituted, an alkoxy group wherein said alkyl group is saturated or unsaturated, branched or linear, substituted or unsubstituted, or when taken together, $R^{11}$ and $R^{12}$ form a 5 or 6 membered ring;

wherein n can be 0, 1, 2 or 3;

wherein Y is $—CR^9=CR^{10}—$;

wherein m and p can have values of 0 or 1 and m+p=1;

wherein at least one of $R^1$, $R^2$, $R^3$, $R^4$, $R^5$, $R^{11}$ or $R^{12}$ comprises Q(1) or at least one of $R^6$, $R^7$, $R^8$, $R^9$ or $R^{10}$ comprises Q(2);

wherein Q(1) comprises a sulfonate ($SO_3^-$), a sulfonate ester ($SO_2ER^{13}$), a sulfoxide ($SOR^{13}$), a sulfone ($SO_2CR^{13}R^{14}R^{15}$), a sulfonamide ($SO_2NR^{13}R^{14}$), a phosphate ($PO_4^=$), a phosphate monoester ($PO_3^-ER^{13}$), a phosphate diester ($PO_2ER^{13}ER^{14}$), a alkyl phosphonate ($PO_3^=$) a alkyl phosphonate monoester ($PO_2^-ER^{13}$) a alkyl phosphonate diester ($POER^{13}ER^{14}$), a thiophosphate ($PSO_3^=$), a thiophosphate monoester ($PSO_2^-ER^{13}$) a thiophosphate diester ($PSOER^{13}ER^{14}$), a thiophosphonate ($PSO_2^=$), a thiophosphonate monoester ($PSO^-ER^{13}$) a thiophosphonate ($PSER^{13}ER^{14}$), a phosphonamide ($PONR^{13}R^{14}NR^{19}R^{23}$), its thioanalogue ($PSNR^{13}R^{14}NR^{19}R^{20}$), a phosphoramide ($PONR^{13}R^{14}NR^{15}NR^{19}R^{20}$), its thioanalogue ($PSNR^{13}R^{14}NR^{15}NR^{19}R^{20}$), a phosphoramidite ($PO_2R^{19}NR^{13}R^{14}$) or its thioanalogue ($POSR^{19}NR^{13}R^{14}$) wherein any of E can independently comprise O or S and the structures are as described previously;

wherein Q is attached directly, or indirectly through a linker arm comprising carbon, sulfur, oxygen, nitrogen, and any combinations thereof and wherein said linker arm may be saturated or unsaturated, linear or branched, substituted or unsubstituted and any combinations thereof and wherein when Q is a sulfonamide, it does not comprise a terminal reactive group or a linker joining the dye to a target molecule;

wherein Q(2) comprises an alkyl, aminoalkyl, substituted aminoalkyl, a benzyl, a substituted benzyl, a sulfoxide ($SOR^{13}$), a sulfone ($SO_2CR^{13}R^{14}R^{16}$), a sulfonamide ($SO_2NR^{13}R^{14}$), a phosphate ($PO_4^=$), a phosphate monoester ($PO_3^-ER^{13}$), a phosphate diester ($PO_2ER^{13}ER^{14}$), a phosphonate ($PO_3^=$) a phosphonate monoester ($PO_2^-ER^{13}$) a phosphonate diester ($POER^{13}ER^{14}$), a thiophosphate ($PSO_3^=$), a thiophosphate monoester ($PSO_2^-ER^{13}$) a thiophosphate diester ($PSOER^{13}ER^{14}$), a thiophosphonate ($PSO_2^=$), a thiophosphonate monoester ($PSO^-ER^{13}$) a thiophosphonate diester (PSER$^{13}$ER$^{14}$), a phosphonamide (PONR$^{13}$R$^{14}$NR$^{19}$R$^{20}$), its thioanalogue (PSNR$^{13}$R$^{14}$NR$^{19}$R$^{20}$), a phosphoramide (PONR$^{13}$R$^{14}$NR$^{15}$NR$^{19}$R$^{20}$), its thioanalogue (PSNR$^{13}$R$^{14}$NR$^{15}$NR$^{19}$R$^{20}$), a phosphoramidite (PO$_2$R$^{19}$NR$^{13}$R$^{14}$) or its thioanalogue (POSR$^{19}$NR$^{13}$R$^{14}$) wherein any of E can independently comprise O or S and the structures are as described previously;

wherein Q(2) is attached directly, or indirectly through a linker arm comprising carbon, sulfur, oxygen, nitrogen, and any combinations thereof and wherein said linker arm may be saturated or unsaturated, linear or branched, substituted or unsubstituted and any combinations thereof and wherein when Q' is a sulfonamide, it does not comprise a terminal reactive group or a linker joining the dye to a target molecule;

wherein R$^{13}$, R$^{14}$, R$^{15}$, R$^{19}$ and R$^{20}$ can be hydrogen, a halogen, an amino group, an alkyl group wherein said alkyl group is saturated or unsaturated, linear or branched, substituted or unsubstituted, an alkoxy group wherein said alkoxy group is saturated or unsaturated, branched or linear, substituted or unsubstituted, or when taken together R$^{13}$ and R$^{14}$ form a five or six membered ring;

wherein R$^{13}$ and R$^{14}$ may further comprise a heteroatom containing side chain wherein said side chain is joined to the R group by a linkage which comprises an ether linkage (—OR$^{25}$), a thioether linkage (—SR$^{25}$), or an amine linkage (—NR$^{25}$R$^{26}$ or N$^+$R$^{25}$R$^{26}$R$^{27}$) and wherein R$^{25}$, R$^{26}$ and R$^{27}$ independently comprise hydrogen, Z, an alkyl group wherein said alkyl group is saturated or unsaturated, linear or branched, substituted or unsubstituted, an alkoxy group that is saturated or unsaturated, branched or linear, substituted or unsubstituted, or when taken together, R$^{25}$ and R$^{26}$, and R$^{26}$ and R$^{27}$ independently comprise a five or six membered ring, and wherein any of R$^{25}$, R$^{26}$ or R$^{27}$ may further comprise said heteroatom containing side chain;

wherein R$^{16}$, R$^{17}$, R$^{18}$ and the remaining R$^1$, R$^2$, R$^3$, R$^4$, R$^5$, R$^6$, R$^7$, R$^8$, R$^9$, R$^{10}$, R$^{11}$ and R$^{12}$ can independently be hydrogen, Z, an alkyl group wherein said alkyl group is saturated or unsaturated, linear or branched, substituted or unsubstituted, an alkoxy group wherein said alkoxy group is saturated or unsaturated, branched or linear; substituted or unsubstituted, or when taken together, R$^2$ and R$^3$, R$^3$ and R$^4$, R$^4$ and R$^5$, R$^6$ and R$^7$, and R$^7$ and R$^8$ may form a 5 or 6 membered ring; or when taken together R$^1$ and R$^{16}$, R$^{11}$ and R$^{16}$, R$^{16}$ and R$^{17}$, R$^{17}$ and R$^{18}$, and R$^{18}$ and R$^9$ may form a 5 or 6 membered ring;

wherein Z comprises a carboxyl group (CO$_2^-$), a carbonate ester (COER$^{13}$), a sulfonate (SO$_3^-$), a sulfonate ester (SO$_2$ER$^{13}$), a sulfoxide (SOR$^{13}$), a sulfone (SO$_2$CR$^{13}$R$^{14}$R$^{15}$), a sulfonamide (SO$_2$NR$^{13}$R$^{14}$), a phosphate (PO$_4^=$), a phosphate monoester (PO$_3^-$ER$^{13}$), a phosphate diester (PO$_2$ER$^{13}$ER$^{14}$), a phosphonate (PO$_3^=$) a phosphonate monoester (PO$_2^-$ER$^{13}$) a phosphonate diester (POER$^{13}$ER$^{14}$), a thiophosphate (PSO$_3^=$), a thiophosphate monoester (PSO$_2^-$ER$^{13}$) a thiophosphate diester (PSO$^-$ER$^{13}$ER$^{14}$), a thiophosphonate (PSO$_2^=$), a thiophosphonate monoester (PSO$^-$ER$^{13}$) a thiophosphonate diester (PSER$^{13}$ER$^{14}$), a phosphonamide (PONR$^{13}$R$^{14}$NR$^{19}$R$^{20}$), its thioanalogue (PSNR$^{13}$R$^{14}$NR$^{19}$R$^{20}$), a phosphonamide (PONR$^{13}$R$^{14}$NR$^{15}$NR$^{19}$R$^{20}$), its thioanalogue (PSNR$^{13}$R$^{14}$NR$^{15}$NR$^{19}$R$^{20}$), a phosphoramidite (PO$_2$R$^{19}$NR$^{13}$R$^{14}$) or its thioanalogue (POSR$^{19}$NR$^{13}$R$^{14}$) where E can be independently O or S and the structures are as described previously;

wherein Z is attached directly, or indirectly through a linker arm comprising carbon, sulfur, oxygen, nitrogen, and any combinations thereof and wherein said linker arm may be saturated or unsaturated, linear or branched, substituted or unsubstituted and any combinations thereof;

wherein any of R$^1$, R$^2$, R$^3$, R$^4$, R$^5$, R$^6$, R$^7$, R$^8$, R$^9$ or R$^{10}$, R$^{11}$ or R$^{12}$ may further comprise a heteroatom containing side chain wherein said side chain is joined to the R group by a linkage which comprises an ether linkage (—OR$^{25}$), a thioether linkage (—SR$^{25}$), or an amine linkage (—NR$^{25}$R$^{26}$ or —N$^+$R$^{25}$R$^{26}$R$^{27}$);

wherein R$^{25}$, R$^{26}$ and R$^{27}$ independently comprise hydrogen, Z, an alkyl group wherein said alkyl group is saturated or unsaturated, linear or branched, substituted or unsubstituted, an alkoxy group that is saturated or unsaturated, branched or linear, substituted or unsubstituted, or when taken together, R$^{25}$ and R$^{26}$, and R$^{26}$ and R$^{27}$ independently comprise a five or six membered ring, and wherein any of R$^{25}$, R$^{26}$ or R$^{27}$ may further comprise said heteroatom containing side chain; and wherein R$^8$ may comprise a substituted group capable of forming symmetric or asymmetric polymeric dye.

In carrying out the above process, the cells (i) can be contacted with the viability dye or dyes (iv) before, during or after the contacting steps (B) and (C).

Other non-xanthene dyes can be used in conjunction with the present invention and the xanthenes compounds (ii). Thus, in step (A), there is further provided at least one non-xanthene dye (v) and wherein the non-xanthene dye (v) is included to carry out step (B) and step (C). Among useful non-xanthene dyes (v) are those comprising a nuclear identification stain, calcein AM, Pheophorbide A, Chloromethylfluorescein diacetate (CMFDA), Hoechst 33342, BODIPY-Prazozin, Fura-2 AM, monobromobimane, BODIPY-Taxol or 3,3'-diethyloxacarbocyanine iodide (DIOC$_2$(3)] or a dye from Table 1, FIG. 1, and a combination of any of the foregoing.

A number of different means are available to carrying out measurement of the fluorescent signals. Thus, in said step (D), measuring can be carried out by a means comprising a flow cytometer, a microplate reader, a microscope, a fluorimeter, a high content screening platform, a high-content cell analysis system or a laser-scanning cytometer and a combination of the foregoing. Such means, instruments, apparatus and the like are commercially available.

Useful levels of sensitivity are obtained by the present invention. In one aspect, the MAF value of the elevated levels of MDR1, MRP and BCRP, or a combination thereof, is greater than about 20. In another aspect, the MAF value is greater than about 25.

Quenching reagents are also useful employed in this invention. Such agents eliminate the need to wash cells after incubation with a xanthene compound, especially useful in microplate-based analytical measurements. Thus, in step (A), there may be provided a quenching reagent (vi) for minimizing extracellular fluorescent signal from the xanthene compound or compounds (ii). Among such quenching reagents are those comprising Evans Blue, o-tolidine, Trypan Blue, Trypan Red or Brilliant Black, and a combination of the foregoing.

Also contemplated by the present invention is the use of surfactants which can optionally be included during the dye loading step in order to enhance the uptake of the xanthine dyes of the present invention. For example, Pluronic surfactants (BASF Corporation) are suitable for this application. Pluronic surfactants act to disperse and stabilize water-insoluble dyes in aqueous solution, thereby facilitating their cellular uptake from aqueous dispersions. An example of an especially suitable surfactant would be Pluronic F127. High concentrations of pluronic surfactants will inhibit ABC transporters, so the concentration must be optimized and titrated carefully. See pluronic L61 listed in Table 3 above as an ABC transporter inhibitor. Pluronic L81, P85 and F108 are also listed in this capacity, with the inhibition potency decreasing in the cited series. With respect to dye loading with minimal ABC transporter inhibition, 0.02% to 0.2% (w/v) pluronic acid is roughly the optimal concentration range for most cell types. A concentration of 0.1% (w/v) is an especially suitable concentration for such applications. The uptake of the xanthine dye, as its cell-permeable ester, employing a surfactant, such as pluronic acid F-127 in the incubating solution, can increase dye loading within cells at least 2-fold relative to loading without the surfactant for the same period of time. Employing pluronic can facilitate measurement of ABC transporter activity in cells that are especially difficult to load with xanthine dyes, including plant protoplasts and myotubules. The use of such surfactants can be employed concomitantly or simultaneously with the xanthene compounds to achieve greater cellular uptake of the xanthene compounds. The surfactants are useful in both cellular uptake and efflux processes for determining drug resistance of cells as well as processes for determining the effect of a test compound across a cell membrane by the membrane transporters MDR1, MRP and/or BRCP. Thus, in the processes of the present invention, at least one surfactant (vii) is provided in step (A) for increasing cellular uptake of the xanthene compound or compounds (ii), and such surfactant or surfactants are used in the various contacting steps with the xanthenes compound or compounds (ii).

Determination of drug resistance in cells can also be carried with cellular efflux. Thus, this invention further provides a process for determining drug resistance of cells of interest, the process comprising the steps of: (A) providing: (i) at least three portions of a clinical or biological sample comprising cells; (ii) at least one xanthene compound that is transportable across a cell membrane by membrane transporters: MDR1, MRP and BCRP; and (iii) one or more membrane transporter inhibitors; (B) contacting cells from a first portion of the clinical or biological sample (i) with at least one xanthene compound (ii) under conditions sufficient to inhibit efflux of the xanthene compound or compounds (ii) from the cells; (C) contacting cells from a second portion of the clinical or biological sample (i) with at least one xanthene compound (ii) under conditions sufficient to permit efflux of the xanthene compound or compounds (ii) from the cells; (D) contacting cells from a third portion of the clinical or biological sample (i) with at least one xanthene compound (ii) and one or more inhibitors (iii); (E) measuring fluorescent signals generated in steps (B), (C) and D; and (F) comparing the fluorescent signals measured in step (D) to determine elevated activities of MDR1, MRP and BCRP, or a combination thereof, thereby determining the drug resistance of the cells of interest.

The present invention additionally provides a process for determining the effect of a test compound on transport across a cell membrane by the membrane transporters: MDR1, MRP and/or BCRP, the process comprising the steps of: (A) providing: (i) at least three portions of a clinical or biological sample comprising cells; (ii) at least one xanthene compound that is transportable across a cell membrane by membrane transporters: MDR1, MRP and BCRP; and (iii) one or more membrane transporter inhibitors; (B) contacting cells from a first portion of the clinical or biological sample (i) with at least one xanthene compound (ii) under conditions sufficient to inhibit efflux of the xanthene compound or compounds (ii) from the cells; (C) contacting cells from a second portion of the clinical or biological sample (i) with at least one xanthene compound (ii) under conditions sufficient to permit efflux of the xanthene compound or compounds (ii) from the cells; (D) contacting cells from a third portion of the clinical or biological sample (i) with at least one xanthene compound (ii) and one or more inhibitors (iii); (E) measuring fluorescent signals generated in steps (B), (C) and D; and (F) comparing the fluorescent signals measured in step (D) to determine elevated activities of MDR1, MRP and BCRP, or a combination thereof, thereby determining the drug resistance of the cells of interest.

In the just described processes, one or more inhibitors (iii) are provided in step (A) in an amount sufficient to substantially prevent transport of the xanthene compound (II) across a cell membrane by one or more of the membrane transporters MDR1, MRP and BCRP. Also in these processes, contacting in step (B) is carried out under said conditions wherein temperature is lowered to inhibit efflux. The temperature can be generally in a range from about 4° C. to about 10° C.

In another aspect of these processes, contacting in step (C) is carried out under conditions wherein temperature is raised or brought to a level to permit efflux. Here, the temperature level is in a range from about 15° C. to about 37° C.

The one or more membrane transporter inhibitors (iii) used in these processes may comprise general inhibitors, specific inhibitors or a combination of general inhibitors and specific inhibitors. As previously described above, such general inhibitors comprise cyclosporin A, biricodar (VX-710), tariquidar (XR9576), plant polyphenols, curcumin, tRA98006 or imatinib mesylate and a combination of any of the foregoing. Further, the specific inhibitors comprise valspodar (PSC833), verapamil, vanadate, PAK-104P, MK-571, FTC, Ko134, Elacridar (GF 120918), novobiocin, probenecid, BIB-E, disulfuram, indomethacin, furocemide, Penicillin G, sulfinpirazole, laniquidar (R101933), zosuquidar (LY335979), ontogeny (ONT-093), isothiocyanates, phytoestrogens, TAG-139, flavenoids, MS-209, NSAIDs, mitotane (NSC-38271), PK11195, cyclosporine D, anthranilamide, pipecolinate, quinoline, OC-144-093, diallyl sulfide, amooranin, agosterol A, siRNA, rifampicin, amiodarone, quinidine, quinine, nifedipine, dexniguldipin, LY455776, V-104, tricyclic izoxazoles, pluronic L61, or fumitremorgin C and a combination of any of the foregoing.

As previously described, the xanthene compound (ii) used in these latter processes has the structure of

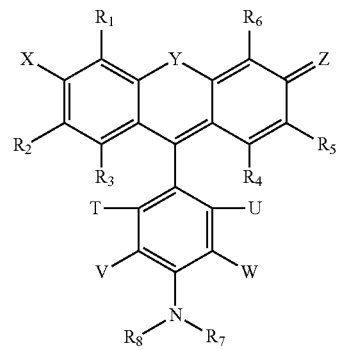

wherein $R^1$-$R^6$ are independently H, halogen, carboxy, alkoxy, aryloxy, thiol, alkylthiol, arylthiol, azido, nitro, nitroso, cyano, amino, hydroxy, phosphonyl, sulfonyl, carbonyl, boronic acid, aryl, or heteroaryl; or alkyl, or alkoxy, optionally substituted one or more times by halogen, amino, hydroxy, phosphonyl, sulfonyl, carbonyl, boronic acid, aryl or heteroaryl, wherein heteroatom Y is independently selected from O, S, Se, $NR^9$ and $CR^{10}R^{11}$, wherein X is independently selected from $OR^{12}$, $NR^{12}R^{13}$ and Z is independently selected from O and $NR^{16}$ where each $R^9$, $R^{10}$, $R^{11}$, $R^{12}$, $R^{13}$, $R^{16}$ and $R^{17}$ is selected from O and NR independently H, an alkyl having 1-12 carbons, carboxyalkyl, substituted or non-substituted amino alkyl or alkylsulfonate, wherein T and U are independently selected from alkyl having 1-12 carbons, alkoxy having 1-12 carbons, aryloxy, amino, halogen, cyano, carboxy, carboxyalkyl, carbonyl, sulfonyl, phosphonyl, boronic acid, aryl, and heteroaryl, and wherein V and W are independently selected from $OR^{14}$, $SR^{15}$ or $NR^{12}R^{13}$, such that at least one of V or W, in combination with $NR^7R^8$, forms a metal chelator, where each $R^7$, $R^8$, and $R^{12}$-$R^{15}$ are independently H, an alkyl having 1-12 carbons, carboxyalkyl, alkoxy or aryloxy.

In a different embodiment of these processes, the xanthene compound (ii) has the structure

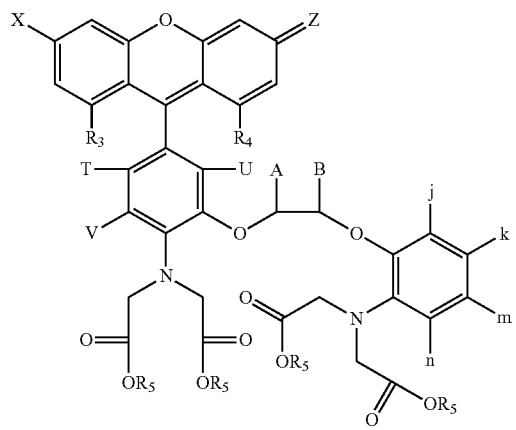

wherein A and B are independently hydrogen, alkyl, cycloalkyl, or aryl; or A and B taken in combination are cycloalkyl or aryl;

wherein $R^3$, $R^4$, j, k, m, n and V are independently hydrogen, halogen, carboxy, alkoxy, aryloxy, thiol, alkylthiol, arylthiol, azido, nitro, nitroso, cyano, amino, hydroxy, phosphonyl, sulfonyl, carbonyl, boronic acid, aryl, or heteroaryl; or alkyl, or alkoxy that is itself optionally substituted one or more times by halogen, amino, hydroxy, phosphonyl, sulfonyl, carbonyl, boronic acid, aryl or heteroaryl;

wherein each $R^5$ is independently hydrogen, alkyl having 1-9 carbons, acetoxymethyl, or a biologically compatible salt; and wherein T and U are independently hydrogen, alkyl having 1-12 carbons, alkoxy having 1-12 carbons, aryloxy, amino, halogen, cyano, carboxy, acetoxymethylcarbonyl, carboxyalkyl, carbonyl, sulfonyl, phosphonyl, boronic acid, aryl or heteroaryl; provided that at least one of T and U is not hydrogen.

In yet another embodiment, the xanthene compound (ii) has the structure

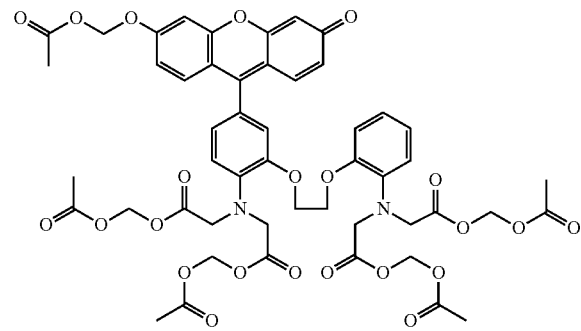 [SMILES: CC(=O)OCOC(=O)CN(CC(=O)OCOC(C)=O)c1ccccc1OCCOc1cc(-c2c3ccc(=O)cc-3oc3cc(OCOC(C)=O)ccc23)ccc1N(CC(=O)OCOC(C)=O)CC(=O)OCOC(C)=O]

In a different aspect of these processes, there is further provided in step (A) at least one viability dye (iv). This viability dye (iv) comprises propidium iodide, 7-amino-actinomycin D (7-AAD), DRAQ-7, Nuclear ID Red, Nuclear ID Green, SYTOX Green, SYTOX Orange, SYTOX Blue, YOYO, TOTO or TO-PRO, and a compound having the structure:

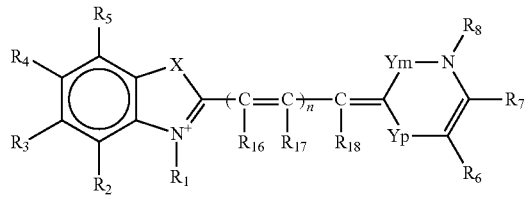

wherein X comprises $CR^{11}R^{12}$, $NR^{11}$, O, S or Se where $R^{11}$ and $R^{12}$ independently comprise hydrogen, a halogen, an amino group, an alkyl group wherein said alkyl group is saturated or unsaturated, linear or branched, substituted or unsubstituted, an alkoxy group wherein said alkyl group is saturated or unsaturated, branched or linear, substituted or unsubstituted, or when taken together, $R^{11}$ and $R^{12}$ form a 5 or 6 membered ring;

wherein n can be 0, 1, 2 or 3;

wherein Y is $-CR^9=CR^{16}-$;

wherein m and p can have values of 0 or 1 and m+p=1;

wherein at least one of $R^1$, $R^2$, $R^3$, $R^4$, $R^5$, $R^{11}$ or $R^{12}$ comprises Q(1) or at least one of $R^6$, $R^7$, $R^8$, $R^9$ or $R^{10}$ comprises Q(2);

wherein Q(1) comprises a sulfonate ($SO_3^-$), a sulfonate ester ($SO_2ER^{13}$), a sulfoxide ($SOR^{13}$), a sulfone ($SO_2CR^{13}R^{14}R^{15}$), a sulfonamide ($SO_2NR^{13}R^{14}$), a phosphate ($PO_4^-$), a phosphate monoester ($PO_3^-ER^{13}$), a phosphate diester ($PO_2ER^{13}ER^{14}$), a alkyl phosphonate ($PO_3^=$) a alkyl phosphonate monoester ($PO2^-ER^{13}$) a alkyl phosphonate diester ($POER^{13}ER^{14}$), a thiophosphate ($PSO_3^=$), a thiophosphate monoester ($PSO_2^-ER^{13}$) a thiophosphate diester ($PSOER^{13}ER^{14}$), a thiophosphonate ($PSO_2^=$), a thiophosphonate monoester ($PSO^-ER^{13}$) a thiophosphonate diester ($PSER^{13}ER^{14}$), a phosphonamide ($PONR^{13}R^{14}NR^{19}R^{20}$), its thioanalogue ($PSNR^{13}R^{14}NR^{19}R^{20}$), a phosphonamide ($PONR^{13}R^{14}NR^{15}NR^{19}R^{20}$), its thioanalogue ($PSNR^{13}R^{14}NR^{15}NR^{19}R^{20}$), a phosphoramidite ($PO_2R^{19}NR^{13}R^{14}$) or its thioanalogue ($POSR^{19}NR^{13}R^{14}$) wherein any of E can independently comprise O or S and the structures are as described previously;

wherein Q is attached directly, or indirectly through a linker arm comprising carbon, sulfur, oxygen, nitrogen, and any combinations thereof and wherein said linker arm may be saturated or unsaturated, linear or branched, substituted or unsubstituted and any combinations thereof and wherein when Q is a sulfonamide, it does not comprise a terminal reactive group or a linker joining the dye to a target molecule;

wherein Q(2) comprises an alkyl, aminoalkyl, substituted aminoalkyl, a benzyl, a substituted benzyl, a sulfoxide ($SOR^{13}$), a sulfone ($SO_2CR^{13}R^{14}R^{15}$), a sulfonamide ($SO_2NR^{13}R^{14}$), a phosphate ($PO_4^-$), a phosphate monoester ($PO_3^-ER^{13}$), a phosphate diester ($PO_2ER^{13}ER^{14}$), a phosphonate ($PO_3^=$) a phosphonate monoester ($PO_2^-ER^{13}$) a phosphonate diester ($POER^{13}ER^{14}$), a thiophosphate ($PSO_3^=$), a thiophosphate monoester ($PSO_2^-ER^{13}$) a thiophosphate diester ($PSOER^{13}ER^{14}$), a thiophosphonate ($PSO_2^=$), a thiophosphonate monoester ($PSO^-ER^{13}$) a thiophosphonate diester ($PSER^{13}ER^{14}$), a phosphonamide ($PONR^{13}R^{14}NR^{19}R^{20}$), its thioanalogue ($PSNR^{13}R^{14}NR^{19}R^{20}$), a phosphoramide (PONR$^{13}$R$^{14}$NR$^{15}$NR$^{19}$R$^{20}$), its thioanalogue (PSNR$^{13}$R$^{14}$NR$^{15}$NR$^{19}$R$^{20}$), a phosphoramidite (PO$_2$R$^{19}$NR$^{13}$R$^{14}$) or its thioanalogue (POSR$^{19}$NR$^{13}$R$^{14}$) wherein any of E can independently comprise O or S and the structures are as described previously;

wherein Q(2) is attached directly, or indirectly through a linker arm comprising carbon, sulfur, oxygen, nitrogen, and any combinations thereof and wherein said linker arm may be saturated or unsaturated, linear or branched, substituted or unsubstituted and any combinations thereof and wherein when Q' is a sulfonamide, it does not comprise a terminal reactive group or a linker joining the dye to a target molecule;

wherein R$^{13}$, R$^{14}$, R$^{15}$, R$^{19}$ and R$^{20}$ can be hydrogen, a halogen, an amino group, an alkyl group wherein said alkyl group is saturated or unsaturated, linear or branched, substituted or unsubstituted, an alkoxy group wherein said alkoxy group is saturated or unsaturated, branched or linear, substituted or unsubstituted, or when taken together R$^{13}$ and R$^{14}$ form a five or six membered ring;

wherein R$^{13}$ and R$^{14}$ may further comprise a heteroatom containing side chain wherein said side chain is joined to the R group by a linkage which comprises an ether linkage (—OR$^{25}$), a thioether linkage (—SR$^{25}$), or an amine linkage (—NR$^{25}$R$^{26}$ or —N$^+$R$^{25}$R$^{26}$R$^{27}$), and wherein R$^{25}$, R$^{26}$ and R$^{27}$ independently comprise hydrogen, Z, an alkyl group wherein said alkyl group is saturated or unsaturated, linear or branched, substituted or unsubstituted, an alkoxy group that is saturated or unsaturated, branched or linear, substituted or unsubstituted, or when taken together, R$^{25}$ and R$^{26}$, and R$^{26}$ and R$^{27}$ independently comprise a five or six membered ring, and wherein any of R$^{25}$, R$^{26}$ or R$^{27}$ may further comprise said heteroatom containing side chain;

wherein R$^{16}$, R$^{17}$, R$^{18}$ and the remaining R$^1$, R$^2$, R$^3$, R$^4$, R$^5$, R$^6$, R$^7$, R$^8$, R$^9$, R$^{10}$, R$^{11}$ and R$^{12}$ can independently be hydrogen, Z, an alkyl group wherein said alkyl group is saturated or unsaturated, linear or branched, substituted or unsubstituted, an alkoxy group wherein said alkoxy group is saturated or unsaturated, branched or linear, substituted or unsubstituted, or when taken together, R$^2$ and R$^3$, R$^3$ and R$^4$, R$^4$ and R$^5$, R$^6$ and R$^7$, and R$^7$ and R$^8$ may form a 5 or 6 membered ring; or when taken together R$^1$ and R$^{16}$, R$^{11}$ and R$^{16}$, R$^{16}$ and R$^{17}$, R$^{17}$ and R$^{18}$, and R$^{18}$ and R$^9$ may form a 5 or 6 membered ring;

wherein Z comprises a carboxyl group (CO$_2^-$), a carbonate ester (COER$^{13}$), a sulfonate (SO$_3^-$), a sulfonate ester (SO$_2$ER$^{13}$), a sulfoxide (SOR$^{13}$), a sulfone (SO$_2$CR$^{13}$R$^{14}$R$^{15}$), a sulfonamide (SO$_2$NR$^{13}$R$^{14}$), a phosphate (PO$_4^=$), a phosphate monoester (PO$_3^-$ER$^{13}$), a phosphate diester (PO$_2$ER$^{13}$ER$^{14}$), a phosphonate (PO$_3^=$) a phosphonate monoester (PO$_2^-$ER$^{13}$) a phosphonate diester (POER$^{13}$ER$^{14}$), a thiophosphate (PSO$_3^=$), a thiophosphate monoester (PSO$_2^-$ER$^{13}$) a thiophosphate diester (PSOER$^{13}$ER$^{14}$), a thiophosphonate (PSO$_2^=$), a thiophosphonate monoester (PSO$^-$ER$^{13}$) a thiophosphonate diester (PSER$^{13}$ER$^{14}$), a phosphonamide (PONR$^{13}$R$^{14}$NR$^{19}$R$^{20}$), its thioanalogue (PSNR$^{13}$R$^{14}$NR$^{19}$R$^{20}$), a phosphoramide (PONR$^{13}$R$^{14}$NR$^{15}$NR$^{19}$R$^{20}$), its thioanalogue (PSNR$^{13}$R$^{14}$NR$^{15}$NR$^{19}$R$^{20}$), a phosphoramidite (PO$_2$R$^{19}$NR$^{13}$R$^{14}$) or its thioanalogue (POSR$^{19}$NR$^{13}$R$^{14}$) where E can be independently O or S and the structures are as described previously;

wherein Z is attached directly, or indirectly through a linker arm comprising carbon, sulfur, oxygen, nitrogen, and any combinations thereof and wherein said linker arm may be saturated or unsaturated, linear or branched, substituted or unsubstituted and any combinations thereof;

wherein any of R$^1$, R$^2$, R$^3$, R$^4$, R$^5$, R$^6$, R$^7$, R$^8$, R$^9$ or R$^{10}$, R$^{11}$ or R$^{12}$ may further comprise a heteroatom containing side chain wherein said side chain is joined to the R group by a linkage which comprises an ether linkage (—OR$^{25}$), a thioether linkage (—SR$^{25}$), or an amine linkage (—NR$^{25}$R$^{26}$ or —N$^+$R$^{25}$R$^{26}$R$^{27}$), wherein R$^{25}$, R$^{26}$ and R$^{27}$ independently comprise hydrogen, Z, an alkyl group wherein said alkyl group is saturated or unsaturated, linear or branched, substituted or unsubstituted, an alkoxy group that is saturated or unsaturated, branched or linear, substituted or unsubstituted, or when taken together, R$^{25}$ and R$^{26}$, and R$^{26}$ and R$^{27}$ independently comprise a five or six membered ring, and wherein any of R$^{25}$, R$^{26}$ or R$^{27}$ may further comprise said heteroatom containing side chain, and wherein R$^8$ may comprise a substituted group capable of forming symmetric or asymmetric polymeric dye.

Mention should be made that the cells (i) can be contacted with the viability dye (iv) before, during or after contacting steps (B), (C) and (D) in the processes above.

Non-xanthene dyes can also be used in these processes. Thus, in step (A), there is further provided at least one such non-xanthene dye (v) which is included in step (B), step (C) and step (D). As previously described above, the non-xanthene dye (v) comprises a nuclear identification stain, calcein AM, Pheophorbide A, Chloromethylfluorescein diacetate (CMFDA), Hoechst 33342, BODIPY-Prazozin, Fura-2 AM, monobromobimane, BODIPY-Taxol or 3,3'-diethyloxacarbocyanine iodide (DIOC$_2$(3)] or a dye from Table 1, FIG. 1, and a combination of any of the foregoing.

Measuring in these latter processes is done similarly as in other processes above. Thus, in step (E), measuring is carried out by a means comprising a flow cytometer, a microplate reader, a microscope, a fluorimeter, a high content screening platform, a high-content cell analysis system or a laser-scanning cytometer and a combination of the foregoing.

In terms of sensitivity of these processes, the MAF value of the elevated levels of MDR1, MRP and BCRP, or a combination thereof, is greater than 20, and even greater than about 25.

Quenching reagents are also useful in the latter processes. Thus in step (A), there is further provided a quenching reagent (vi) for minimizing extracellular fluorescent signal from the xanthene compound (ii). As described for other processes above, the quenching reagent (vi) comprises Evans Blue, o-tolidine, Trypan Blue, Trypan Red or Brilliant Black, and a combination of the foregoing.

Reagent Kits:

As explained above, multidrug resistance (MDR) relates to the resistance of tumor cells to a variety of chemotherapy drugs with different structures and cellular targets. The phenomenon of multidrug resistance (MDR) is a well-known problem in oncology and thus needs profound consideration in cancer treatment. One of the underlying molecular rationales for MDR is the up-regulation of a family of transmembrane ATB binding cassette (ABC) transporter proteins that are present in practically all living organisms. These proteins cause chemotherapy resistance in cancer by actively extruding a wide range of therapeutic compounds from the malignant cells. The same ABC transporters play an important protective function against toxic compounds in a variety of cells and tissues and at blood-tissue barriers.

Enzo Life Sciences' eFluxx-ID™ Multidrug Resistance Assay Kits have been designed for functional detection and profiling of multidrug resistant phenotypes in live cells (both suspension and adherent) and will be shortly available commercially. The kits include either a green fluorescent or orange fluorescent eFluxx-ID™ Detection Reagent as a major component. Both dyes are excited by a 488 nm laser. Being a substrate for all three main ABC transporter proteins, these reagents serve as indicators of transporter protein activity in cells. The proprietary AM-ester forms of the eFluxx-ID™ Detection Reagents are hydrophobic non-fluorescent compounds that readily penetrate the cell membrane and are subsequently hydrolyzed inside of the cells by intracellular esterases. The resulting probe is a hydrophilic fluorescent dye that is trapped within the cell unless actively pumped out by an ABC transporter. The fluorescence signal of the dye generated within the cells thus depends upon the activity of the ABC transporters. The cells with highly active transporters will demonstrate lower fluorescence because of the active efflux of the reagent from the cell. Application of specific inhibitors of the various ABC transporter proteins, included in the kit, allows differentiation between the three common types of pumps. The activity of a particular MDR transporter is defined by the difference between the amount of the dye accumulated in the presence and in the absence of the inhibitors, respectively The flow cytometry assay is based upon determining fluorescence intensities of the tested cells after a short in vitro incubation of cell suspensions with the eFluxx-ID Detection Reagent, in the presence or absence of specific ABC transporter inhibitors. The results of the test can be quantified by calculating the MDR activity factor (MAE), which allow comparison of multidrug resistance between the samples or cell lines.

Commercial kits, such as the just-described Enzo's eFluxx-ID™ Multidrug Resistance Assay Kits, are valuable because they eliminate the need for individual laboratories to optimize procedures, saving both time and resources. They also allow better cross-comparison of results generated from different laboratories. The present invention additionally provides reagent kits, i.e., reagent combinations or means, comprising all of the essential elements required to conduct a desired assay method. The reagent system is presented in a commercially packaged form, as a composition or admixture where the compatibility of the reagents will allow, in a test kit, i.e., a packaged combination of one or more containers, devices or the like holding the necessary reagents, and usually written instructions for the performance of the assays. Reagent systems of the present invention include all configurations and compositions for performing the various labeling and staining formats described herein.

The reagent system will contain at least one fluorogenic indicator, generally comprising packaged combinations of the following:

(1) one or more fluorogenic global MDR indicator;

(2) optionally, one or more fluorogenic indicator with selectivity for some sub-class of MDR analyte;

(3) optionally, one or more specific inhibitors of MDR activity; and (4) instructions for usage of the included reagents;

Generic instructions, as well as specific instructions for the use of the reagents on particular instruments, such as a flow cytometer or microplate-based detection platform may be provided. Recommendations regarding filter sets, monochromator settings and/or illumination sources for optimal performance of the reagents for a particular application also may be provided. Instructions for quantitative assay evaluation also may be provided.

A test kit form designed to directly monitor activity of various ABC transporter proteins in live cells, both pro- and eukaryotic. Such form, for example, can contain an indicator of global MDR activity (e.g. Fluo-8™ AM or Rhod-4™ AM), and additional ancillary chemicals, such as verapamil (Pgp specific inhibitor), MK-571 (MRP1/2 specific inhibitor), novobiocin (BCRP specific inhibitor), assay buffer (e.g. medium), and diluent. In some instances, one or more fluorogenic compound (MDR probes) may be added to a kit form for better specificity of the detection. One or more chemicals serving as inhibitors of MDR activity may be added to a kit form.

The present invention provides a kit for determining drug resistance of cells of interest, or detecting and profiling multidrug resistant phenotypes in cells of interest, or determining activity levels of membrane transporters MDR1, MRP and BCRP, the kit comprising in packaged combination: (i) at least one xanthene compound that is transportable across a cell membrane by membrane transporters: MDR1, MRP and BCRP; (ii) one or more membrane transporter inhibitors; and (iii) instructions therefor.

In one aspect, this kit further comprising buffer (iv). In another aspect, this kit measures cellular uptake or efflux of the xanthene compound or compounds (i). In this kit, the one or more inhibitors (ii) can be provided in an amount sufficient to substantially inhibit transport of the xanthene compound or compounds (i) across a cell membrane by one or more of the membrane transporters MDR1, MRP and BCRP.

Such xanthenes compounds have been described above and can take various forms, including a xanthene compound (i) having the structure of

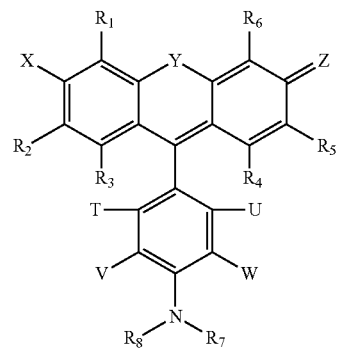

wherein $R^1$-$R^6$ are independently H, halogen, carboxy, alkoxy, aryloxy, thiol, alkylthiol, arylthiol, azido, nitro, nitroso, cyano, amino, hydroxy, phosphonyl, sulfonyl, carbonyl, boronic acid, aryl, or heteroaryl; or alkyl, or alkoxy, optionally substituted one or more times by halogen, amino, hydroxy, phosphonyl, sulfonyl, carbonyl, boronic acid, aryl or heteroaryl, wherein heteroatom Y is independently selected from O, S, Se, $NR^9$ and $CR^{10}R^{11}$, wherein X is independently selected from $OR^{12}$, $NR^{12}R^{13}$ and Z is independently selected from O and $NR^{16}R^{17}$, where each $R^9$, $R^{10}$, $R^{11}$, $R^{12}$, $R^{13}$, $R^{16}$ and $R^{17}$ is independently H, an alkyl having 1-12 carbons, carboxyalkyl, substituted or non-substituted amino alkyl or alkylsulfonate, wherein T and U are independently selected from alkyl having 1-12 carbons, alkoxy having 1-12 carbons, aryloxy, amino, halogen, cyano, carboxy, carboxyalkyl, carbonyl, sulfonyl, phosphonyl, boronic acid, aryl, and heteroaryl, and wherein V and W are independently selected from $OR^{14}$, $SR^{15}$ or $NR^{12}R^{13}$, such that at least one of V or W, in combination with $NR^7R^8$, forms a metal chelator, where each $R^7$, $R^8$, and $R^{12}$-$R^{15}$ are independently H, an alkyl having 1-12 carbons, carboxyalkyl, alkoxy or aryloxy.

As also described above, the xanthene compound (i) has the structure

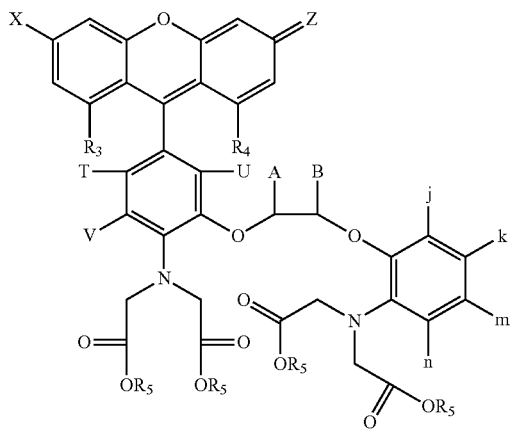

wherein A and B are independently hydrogen, alkyl, cycloalkyl, or aryl; or A and B taken in combination are cycloalkyl or aryl;

wherein $R^3$, $R^4$, j, k, m, n and V are independently hydrogen, halogen, carboxy, alkoxy, aryloxy, thiol, alkylthiol, arylthiol, azido, nitro, nitroso, cyano, amino, hydroxy, phosphonyl, sulfonyl, carbonyl, boronic acid, aryl, or heteroaryl; or alkyl, or alkoxy that is itself optionally substituted one or more times by halogen, amino, hydroxy, phosphonyl, sulfonyl, carbonyl, boronic acid, aryl or heteroaryl;

wherein each $R^5$ is independently hydrogen, alkyl having 1-9 carbons, acetoxymethyl, or a biologically compatible salt; and wherein T and U are independently hydrogen, alkyl having 1-12 carbons, alkoxy having 1-12 carbons, aryloxy, amino, halogen, cyano, carboxy, acetoxymethylcarbonyl, carboxyalkyl, carbonyl, sulfonyl, phosphonyl, boronic acid, aryl or heteroaryl; provided that at least one of T and U is not hydrogen.

Moreover, the xanthene compound (i) in this kit has the structure

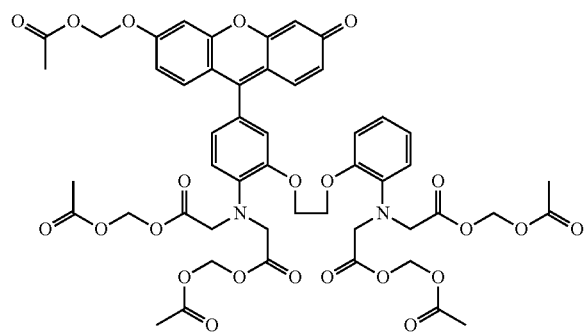 [SMILES: CC(=O)OCOC(=O)CN(CC(=O)OCOC(C)=O)c1ccccc1OCCOc1cc(-c2c3ccc(=O)cc-3oc3cc(OCOC(C)=O)ccc23)ccc1N(CC(=O)OCOC(C)=O)CC(=O)OCOC(C)=O]

As part of the kit, the one or more inhibitors (ii) comprise general inhibitors, specific inhibitors or a combination of general inhibitors and specific inhibitors. Among such general inhibitors previously described are those comprising cyclosporin A, biricodar (VX-710), tariquidar (XR9576), plant polyphenols, curcumin, tRA98006 or imatinib mesylate and a combination of any of the foregoing. Among specific inhibitors also described previously are those comprising valspodar (PSC833), verapamil, vanadate, PAK-104P, MK-571, FTC, Ko134, Elacridar (GF 120918), novobiocin, probenecid, BIB-E, disulfuram, indomethacin, furocemide, Penicillin G, sulfinpirazole, laniquidar (R101933), zosuquidar (LY335979), ontogeny (ONT-093), isothiocyanates, phytoestrogens, TAG-139, flavenoids, MS-209, NSAIDs, mitotane (NSC-38271), PK11195, cyclosporine D, anthranilamide, pipecolinate, quinoline, OC-144-093, diallyl sulfide, amooranin, agosterol A, siRNA, rifampicin, amiodarone, quinidine, quinine, nifedipine, dexniguldipin, LY455776, V-104, tricyclic izoxazoles, pluronic L61, or fumitremorgin C and a combination of any of the foregoing.

At least one viability dye (iv) may also be incorporated and used as part of the afore-described kit. Such viability dyes (iv) comprise propidium iodide, 7-amino-actinomycin D (7-AAD), DRAQ7™, membrane impermeable form of Nuclear-ID™ Red, membrane impermeable form of Nuclear-ID™ Green, SYTOX® Green, SYTOX® Orange, SYTOX® Blue, YOYO, TOTO or TO-PRO, and a compound having the structure:

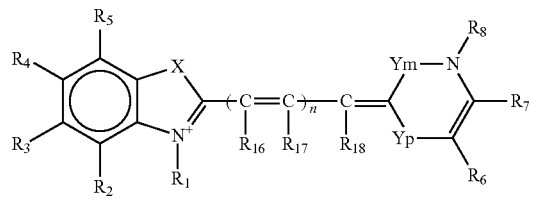

wherein X comprises $CR^{11}R^{12}$, $NR^{11}$, O, S or Se where $R^{11}$ and $R^{12}$ independently comprise hydrogen, a halogen, an amino group, an alkyl group wherein said alkyl group is saturated or unsaturated, linear or branched, substituted or unsubstituted, an alkoxy group wherein said alkyl group is saturated or unsaturated, branched or linear, substituted or unsubstituted, or when taken together, $R^{11}$ and $R^{12}$ form a 5 or 6 membered ring;

wherein n can be 0, 1, 2 or 3;

wherein Y is $—CR^9 = CR^{16}—$;

wherein m and p can have values of 0 or 1 and m+p=1;

wherein at least one of $R^1$, $R^2$, $R^3$, $R^4$, $R^5$, $R^{11}$ or $R^{12}$ comprises Q(1) or at least one of $R^6$, $R^7$, $R^8$, $R^9$ or $R^{10}$ comprises Q(2);

wherein Q(1) comprises a sulfonate ($SO_3^-$), a sulfonate ester ($SO_2ER^{13}$), a sulfoxide ($SOR^{13}$), a sulfone ($SO_2CR^{13}R^{14}R^{15}$), a sulfonamide ($SO_2NR^{13}R^{14}$), a phosphate ($PO_4^=$), a phosphate monoester ($PO_3^-ER^{13}$), a phosphate diester ($PO_2ER^{13}ER^{14}$), a alkyl phosphonate ($PO_3^=$) a alkyl phosphonate monoester ($PO_2^-ER^{13}$) a alkyl phosphonate diester ($POER^{13}ER^{14}$), a thiophosphate ($PSO_3^=$), a thiophosphate monoester ($PSO_2^-ER^{13}$) a thiophosphate diester ($PSOER^{13}ER^{14}$), a thiophosphonate ($PSO_2^=$), a thiophosphonate monoester ($PSO^-ER^{13}$) a thiophosphonate diester ($PSER^{13}ER^{14}$), a phosphonamide ($PONR^{13}R^{14}NR^{19}R^{20}$), its thioanalogue ($PSNR^{13}R^{14}NR^{19}R^{20}$), a phosphoramide ($PONR^{13}R^{14}NR^{15}NR^{19}R^{20}$), its thioanalogue ($PSNR^{13}R^{14}NR^{15}NR^{19}R^{20}$), a phosphoramidite ($PO_2R^{19}NR^{13}R^{14}$) or its thioanalogue ($POSR^{19}NR^{13}R^{14}$) wherein any of E can independently comprise O or S and the structures are as described previously;

wherein Q is attached directly, or indirectly through a linker arm comprising carbon, sulfur, oxygen, nitrogen, and any combinations thereof and wherein said linker arm may be saturated or unsaturated, linear or branched, substituted or unsubstituted and any combinations thereof and wherein when Q is a sulfonamide, it does not comprise a terminal reactive group or a linker joining the dye to a target molecule;

wherein Q(2) comprises an alkyl, aminoalkyl, substituted aminoalkyl, a benzyl, a substituted benzyl, a sulfoxide ($SOR^{13}$), a sulfone ($SO_2CR^{13}R^{14}R^{15}$), a sulfonamide ($SO_2NR^{13}R^{14}$), a phosphate ($PO_4^=$), a phosphate monoester ($PO_3^-ER^{13}$), a phosphate diester ($PO_2ER^{13}ER^{14}$), a phosphonate ($PO_3^=$) a phosphonate monoester ($PO_2^-ER^{13}$) a phosphonate diester ($POER^{13}ER^{14}$), a thiophosphate ($PSO_3^=$), a thiophosphate monoester ($PSO_2^-ER^{13}$) a thiophosphate diester ($PSOER^{13}ER^{14}$), a thiophosphonate ($PSO_2^=$), a thiophosphonate monoester ($PSO^-ER^{13}$) a thiophosphonate diester ($PSER^{13}ER^{14}$), a phosphonamide ($PONR^{13}R^{14}NR^{19}R^{20}$), its thioanalogue ($PSNR^{13}R^{14}NR^{19}R^{20}$), a phosphoramide ($PONR^{13}R^{14}NR^{15}NR^{19}R^{20}$), its thioanalogue ($PSNR^{13}R^{14}NR^{15}NR^{19}R^{20}$), a phosphoramidite ($PO_2R^{19}NR^{13}R^{14}$) or its thioanalogue ($POSR^{19}NR^{13}R^{14}$) wherein any of E can independently comprise O or S and the structures are as described previously;

wherein Q(2) is attached directly, or indirectly through a linker arm comprising carbon, sulfur, oxygen, nitrogen, and any combinations thereof and wherein said linker arm may be saturated or unsaturated, linear or branched, substituted or unsubstituted and any combinations thereof and wherein when Q' is a sulfonamide, it does not comprise a terminal reactive group or a linker joining the dye to a target molecule;

wherein $R^{13}$, $R^{14}$, $R^{15}$, $R^{19}$ and $R^{20}$ can be hydrogen, a halogen, an amino group, an alkyl group wherein said alkyl group is saturated or unsaturated, linear or branched, substituted or unsubstituted, an alkoxy group wherein said alkoxy group is saturated or unsaturated, branched or linear, substituted or unsubstituted, or when taken together $R^{13}$ and $R^{14}$ form a five or six membered ring;

wherein $R^{13}$ and $R^{14}$ may further comprise a heteroatom containing side chain wherein said side chain is joined to the R group by a linkage which comprises an ether linkage ($—OR^{25}$), a thioether linkage ($—SR^{25}$), or an amine linkage ($—NR^{25}R^{26}$ or $N^+R^{25}R^{26}R^{27}$), and wherein $R^{25}$, $R^{26}$ and $R^{27}$ independently comprise hydrogen, Z, an alkyl group wherein said alkyl group is saturated or unsaturated, linear or branched, substituted or unsubstituted, an alkoxy group that is saturated or unsaturated, branched or linear, substituted or unsubstituted, or when taken together, $R^{25}$ and $R^{26}$, and $R^{26}$ and $R^{27}$ independently comprise a five or six membered ring, and wherein any of $R^{25}$, $R^{26}$ or $R^{27}$ may further comprise said heteroatom containing side chain;

wherein $R^{16}$, $R^{17}$, $R^{18}$ and the remaining $R^1$, $R^2$, $R^3$, $R^4$, $R^5$, $R^6$, $R^7$, $R^8$, $R^9$, $R^{10}$, $R^{11}$ and $R^{12}$ can independently be hydrogen, Z, an alkyl group wherein said alkyl group is saturated or unsaturated, linear or branched, substituted or unsubstituted, an alkoxy group wherein said alkoxy group is saturated or unsaturated, branched or linear, substituted or unsubstituted, or when taken together, $R^2$ and $R^3$, $R^3$ and $R^4$, $R^4$ and $R^5$, $R^6$ and $R^7$, and $R^7$ and $R^8$ may form a 5 or 6 membered ring; or when taken together $R^1$ and $R^{16}$, $R^{11}$ and $R^{16}$, $R^{16}$ and $R^{17}$, $R^{17}$ and $R^{18}$, and $R^{18}$ and $R^9$ may form a 5 or 6 membered ring;

wherein Z comprises a carboxyl group ($CO_2^-$), a carbonate ester ($COER^{13}$), a sulfonate ($SO_3^-$), a sulfonate ester ($SO_2ER^{13}$), a sulfoxide ($SOR^{13}$), a sulfone ($SO_2CR^{13}R^{14}R^{15}$), a sulfonamide ($SO_2NR^{13}R^{14}$), a phosphate ($PO_4^=$), a phosphate monoester ($PO_3^-ER^{13}$), a phosphate diester ($PO_2ER^{13}ER^{14}$), a phosphonate ($PO_3^=$) a phosphonate monoester ($PO_2^-ER^{13}$), a phosphonate diester ($POER^{13}ER^{14}$), a thiophosphate ($PSO_3^=$), a thiophosphate monoester ($PSO_2^-ER^{13}$) a thiophosphate diester ($PSOER^{13}ER^{14}$), a thiophosphonate ($PSO_2^=$), a thiophosphonate monoester ($PSO^-ER^{13}$) a thiophosphonate diester ($PSER^{13}ER^{14}$), a phosphonamide ($PONR^{13}R^{14}NR^{19}R^{20}$), its thioanalogue ($PSNR^{13}R^{14}NR^{19}R^{20}$), a phosphoramide ($PONR^{13}R^{14}NR^{15}NR^{19}R^{20}$), its thioanalogue ($PSNR^{13}R^{14}NR^{15}NR^{19}R^{20}$), a phosphoramidite ($PO_2R^{19}NR^{13}R^{14}$) or its thioanalogue ($POSR^{19}NR^{13}R^{14}$) where E can be independently O or S and the structures are as described previously;

wherein Z is attached directly, or indirectly through a linker arm comprising carbon, sulfur, oxygen, nitrogen, and any combinations thereof and wherein said linker arm may be saturated or unsaturated, linear or branched, substituted or unsubstituted and any combinations thereof;

wherein any of $R^1$, $R^2$, $R^3$, $R^4$, $R^5$, $R^6$, $R^7$, $R^8$, $R^9$ or $R^{10}$, $R^{11}$ or $R^{12}$ may further comprise a heteroatom containing side chain wherein said side chain is joined to the R group by a linkage which comprises an ether linkage ($—OR^{25}$), a thioether linkage ($—SR^{25}$), or an amine linkage ($—NR^{25}R^{26}$ or $—N^+R^{25}R^{26}R^{27}$);

wherein $R^{25}$, $R^{26}$ and $R^{27}$ independently comprise hydrogen, Z, an alkyl group wherein said alkyl group is saturated or unsaturated, linear or branched, substituted or unsubstituted, an alkoxy group that is saturated or unsaturated, branched or linear, substituted or unsubstituted, or when taken together, $R^{25}$ and $R^{26}$, and $R^{26}$ and $R^{27}$ independently comprise a five or six membered ring, and wherein any of $R^{25}$, $R^{26}$ or $R^{27}$ may further comprise said heteroatom containing side chain, and wherein $R^8$ may comprise a substituted group capable of forming symmetric or asymmetric polymeric dye.

As in the case of the variously described processes of the present invention, at least one non-xanthene dye (v) can be incorporated and used in this kit. Such non-xanthene dyes have been described above and comprise a nuclear identification stain, calcein AM, Pheophorbide A, Chloromethylfluorescein diacetate (CMFDA), Hoechst 33342, BODIPY-Prazozin, Fura-2 AM, monobromobimane, BODIPY-Taxol or 3,3'-diethyloxacarbocyanine iodide ($DIOC_2(3)$) or a dye from Table 1, FIG. 1, and a combination of any of the foregoing.

Quenching reagents are also applicable to the kit of the present invention. These quenching reagents minimize extracellular fluorescent signal from the xanthene compound (i). Examples of useful quenching reagents have been given above and include Evans Blue, o-tolidine, Trypan Blue, Trypan Red or Brilliant Black, and a combination of the foregoing.

The examples which follow are set forth to illustrate various aspects of the present invention but are not intended in any way to limit its scope as more particularly set forth and defined in the claims that follow thereafter.

DESCRIPTION OF THE PREFERRED EMBODIMENTS

Example 1

Demonstration of Multidrug Resistance in Mammalian Cell Lines Using MTT Method

Human cervical adenocarcinoma epithelial cell line HeLa (putative MDR negative cell line), human lung carcinoma cell line A549 (over-expression of MPR1 and BCRP) [Sharenberg et al., Blood 99:507-512 (2002); McCollum et al., Cancer Res 68:7419-7427 (2008)]) and hamster ovary CHO K1 cell line (over-expression of all three major ABC transporter proteins) [Ling et al., Cancer Treat Rep 67:869-874 (1983);

Gupta et al., Biochem Biophys Res Comm 153:598-605 (1988)]) were obtained from ATCC (Manassas, Va.). HeLa cells were routinely cultured in Eagle's Minimum Essential Medium with low glucose (ATCC), supplemented with 10% fetal bovine serum (ATCC) and 100 U/ml penicillin, 100 ug/ml streptomycin (Sigma-Aldrich, St. Louis, Mo.). A549 and CHO K1 cells were routinely cultured in F-12K medium (ATCC), supplemented with 10% fetal bovine serum (ATCC) and 100 U/ml penicillin, 100 µg/ml streptomycin (Sigma-Aldrich, St. Louis, Mo.). Cell cultures were maintained in a humidified incubator at 37° C., with 5% $CO_2$ atmosphere.

To confirm drug resistance of the above cell lines used as models, cells were seeded in 96-well plates at a density of $5 \times 10^3$ cells/well and 24 h later, treated with increasing doses of different drugs that are commonly used for cancer chemotherapy and are known to be associated with the phenomenon of MDR (taxol, doxorubicin, vincristine, mitoxantrone). A standard 3-(4,5-dimethylthiazol-2-yl)-2,5-diphenyltetrazolium bromide (MTT) viability test was performed 24 and 48 h post-treatment, as described elsewhere [Mosmann T., J Immunol Methods 65(1-2):55-63 (1983)]. Viability was calculated as a ratio of $OD_{595}$ for treated cells to the $OD_{595}$ of untreated control cells. Data from the MTT test confirmed higher chemoresistance of CHO K1 and A549 cells compared to HeLa cells toward all toxic compounds used in the study (FIGS. 2A-D). CHO K1 and A549 cell lines were used as model cell lines demonstrating MDR activity in all following studies. No genetically modified cell lines were used as models in the present application since the levels of MDR activity in these cell lines is already much higher compared with standard clinical samples.

Example 2

Minimal Fluo-8™ AM and Rhod-4™ AM Dye Toxicity

Human cervical adenocarcinoma epithelial cell line HeLa (putative MDR negative cell line), human lung carcinoma cell line A549 and hamster ovary CHO K1 cell line were cultured as described in the Example 1. Fluo-8™ AM and Rhod-4™ AM fluorescent probes were dissolved in anhydrous DMSO at the following concentrations: Fluo-8™ AM—1 mM (a 200× stock solution), Rhod-4™ AM—2 mM (a 1000× stock solutions). 1 mM (2000×) stock solution of Calcein AM was prepared for control measurements. Stock solutions of the dyes were aliquoted and stored at −20° C. in the dark.

Figures 1, 8A:
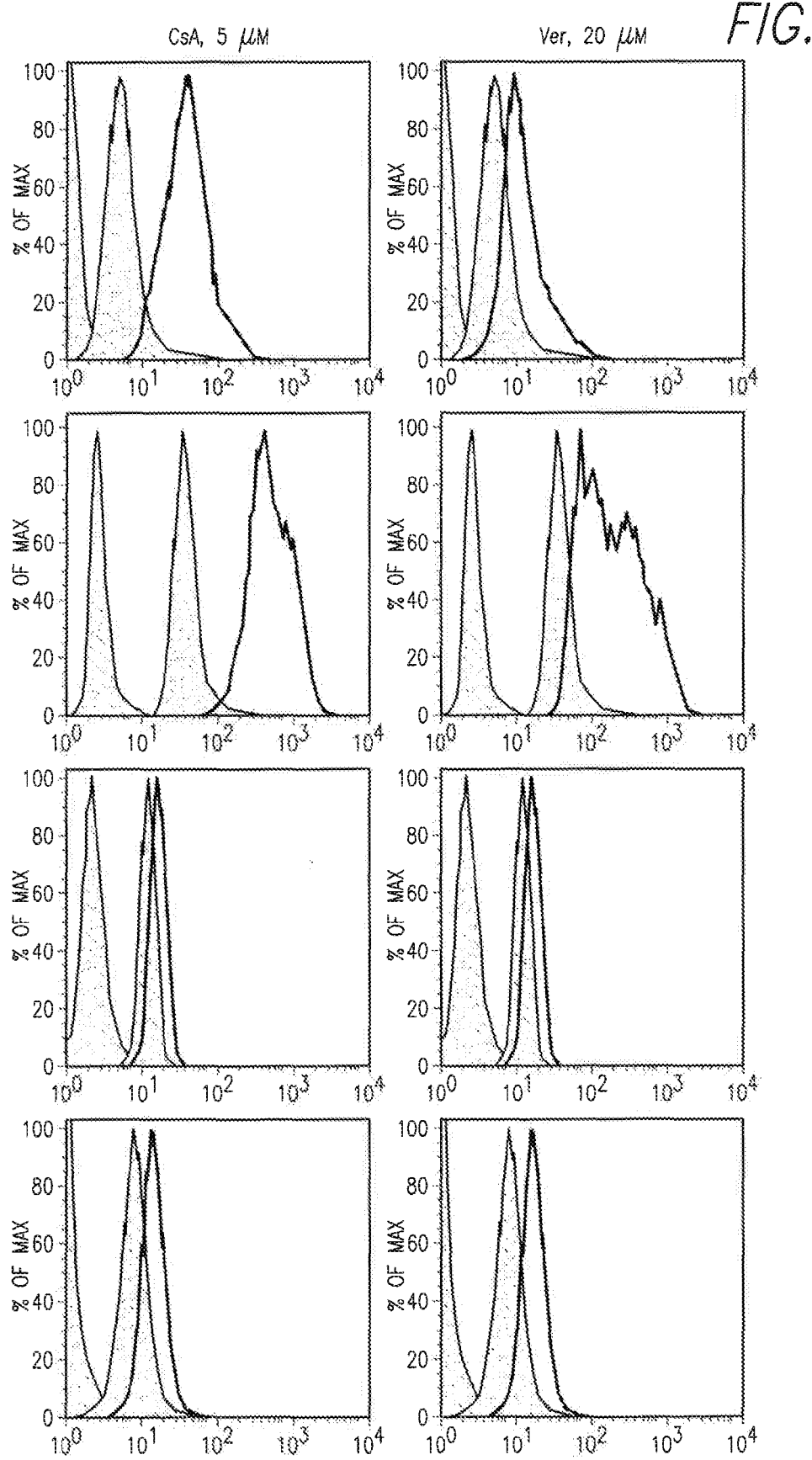
Figures 3, 8A:
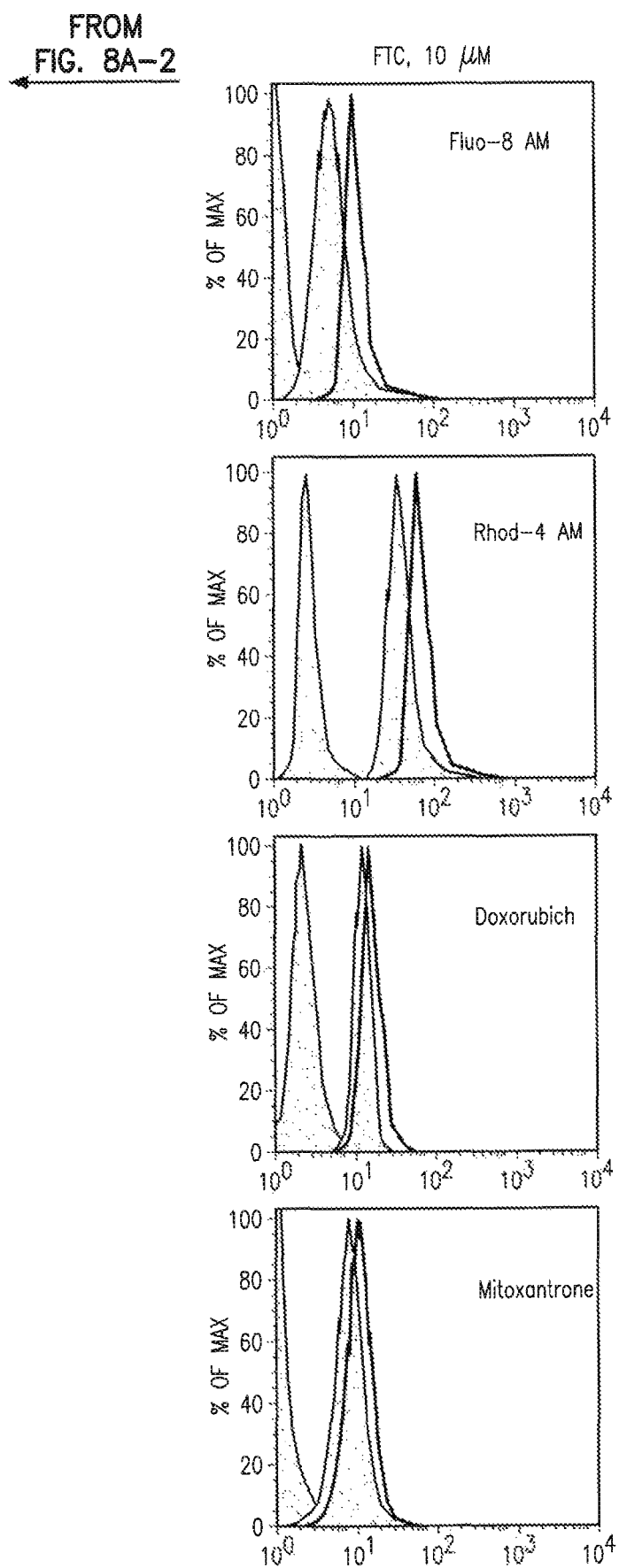
Figures 1, 8B:
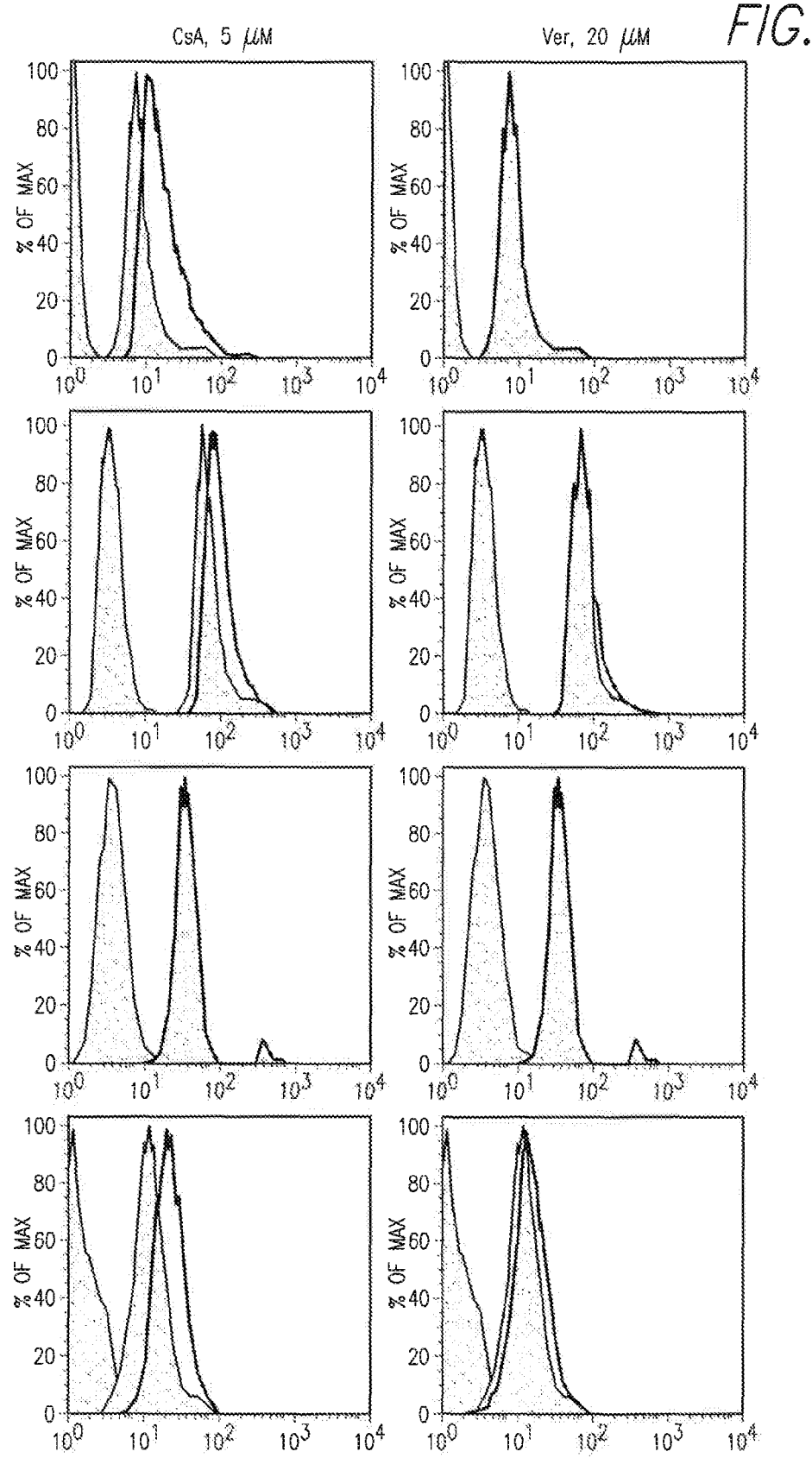
Figures 3, 8B:
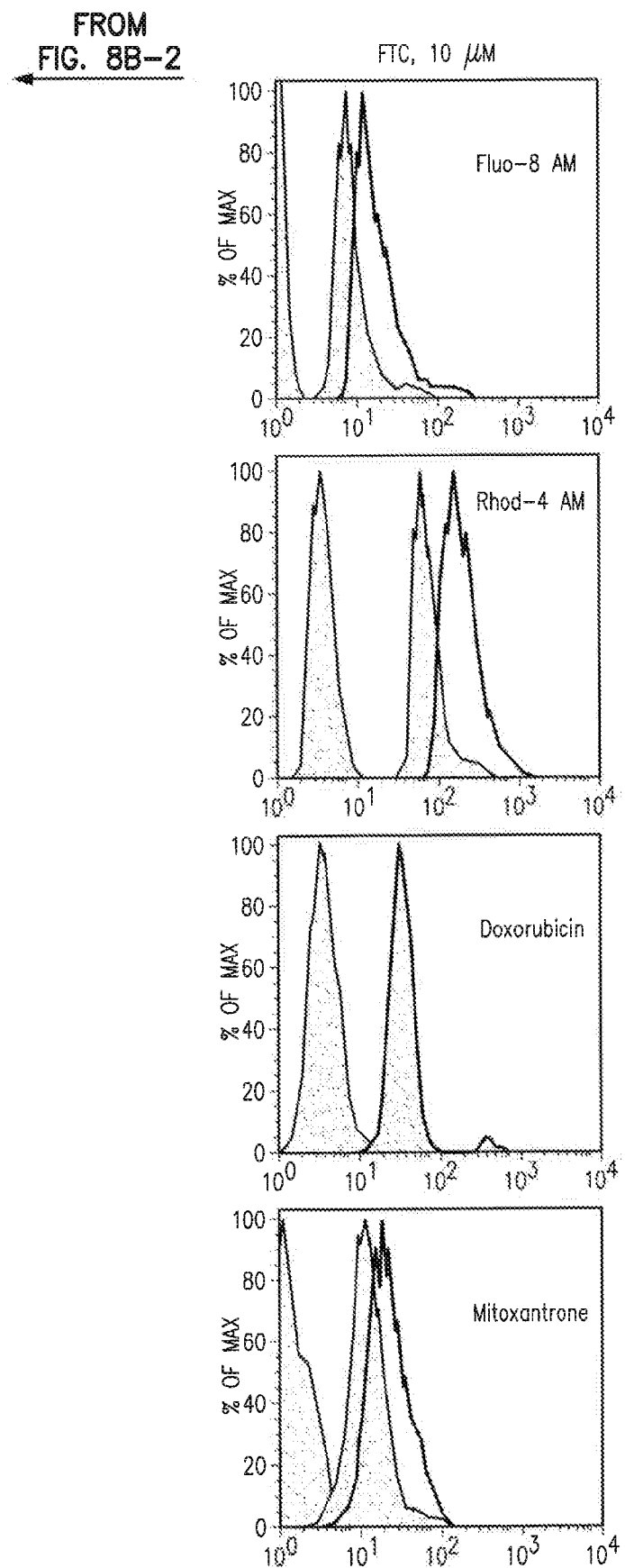
Figures 1, 2, 9A:
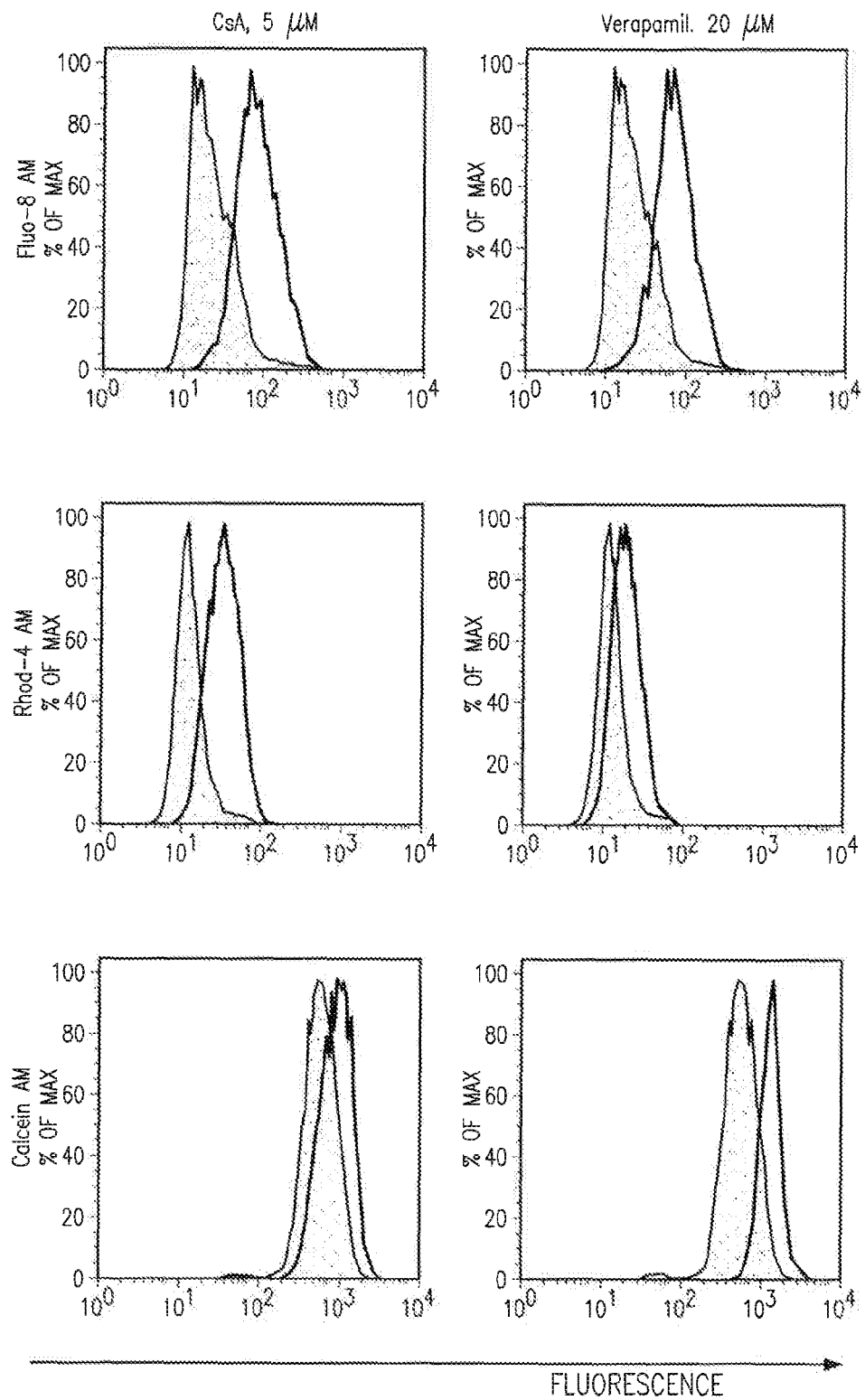
Figures 2, 9A:
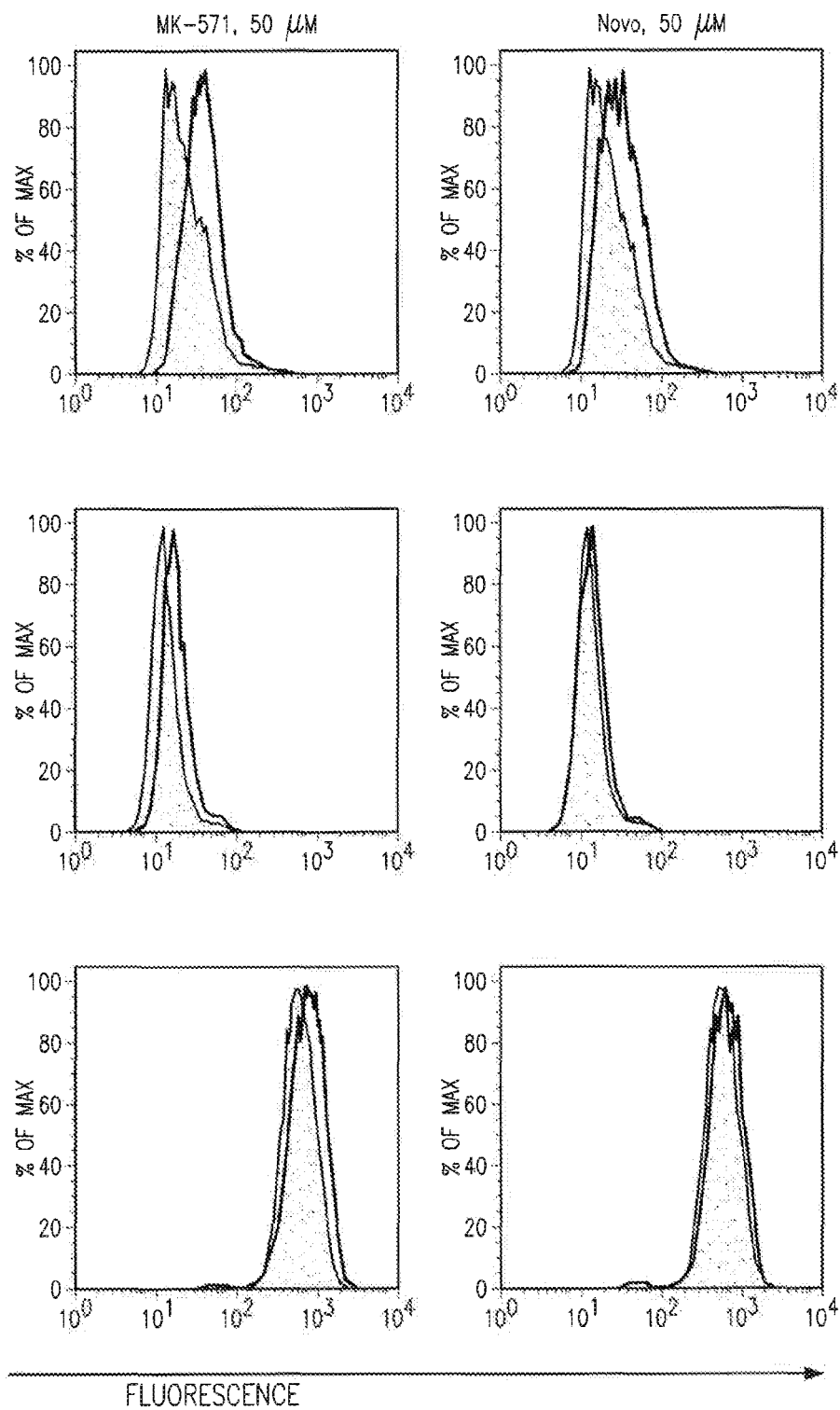
Figures 1, 2, 9B:
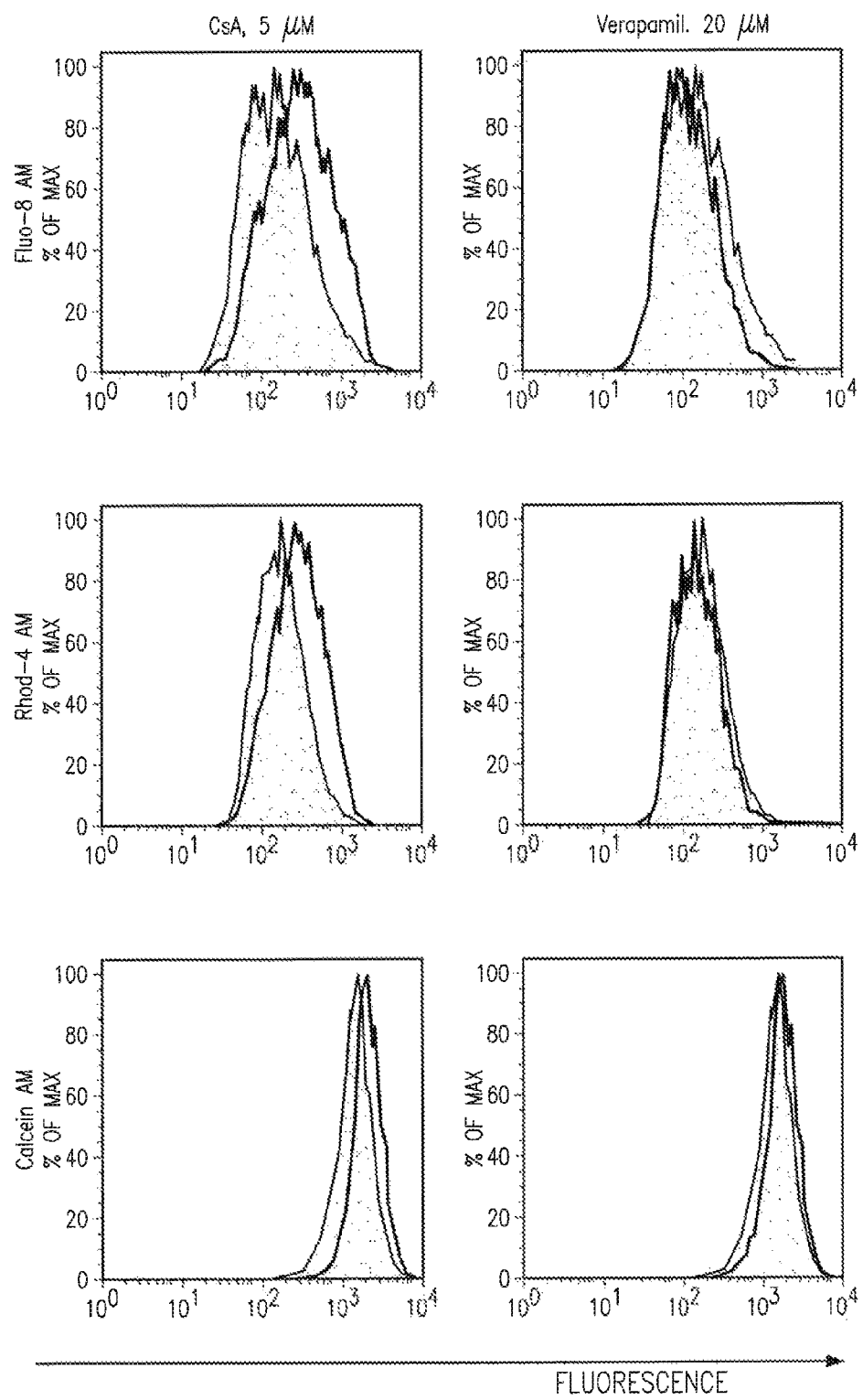
Figures 2, 9B:
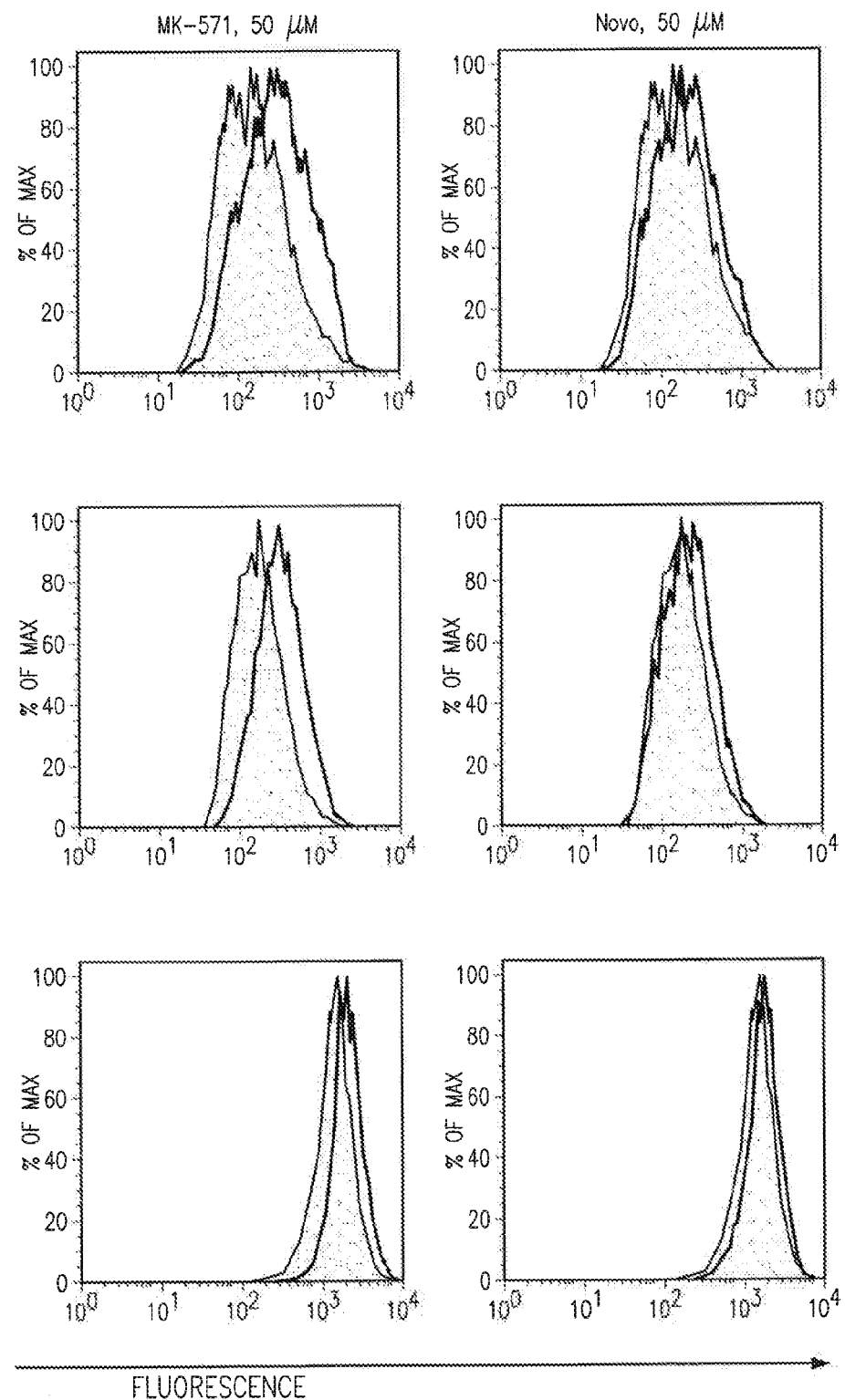

Three model cell lines (CHO K1, A549 and HeLa cells) were seeded in 96 well plates ($5 \times 10^3$ cells/well) and 24 h later were treated with the working concentrations of dyes (0.5 µM of Calcein AM, 5 µM of Fluo-8™ AM, 4 µM of Rhod-4™ AM) used in the MDR assay for 3 h at 37° C. Then reagents were removed and a standard MTT test was performed as described elsewhere [Mosmann T., J Immunol Methods 65(1-2):55-63 (1983)]. Viability was calculated as a ratio of $OD_{595}$ for treated cells to the $OD_{595}$ of untreated control cells (FIG. 3). Data presented in FIG. 3 show that Fluo-8™ was not toxic to the cells, and Rhod-4™ shows only minimal toxicity in CHO K1 cell line after prolonged incubation. Standard MDR experimental protocols do not require, however, such long incubation periods with the dye at 37° C.; therefore, in the authentic assay any toxic effect would be much milder than illustrated in this example. Additionally, the concentration of Rhod-4™ AM can be decreased further for particularly sensitive cell lines.

Example 3

Development of the Minimal Step Assay Procedure for the Dye Uptake Flow Cytometry Protocol Human cervical adenocarcinoma epithelial cell line HeLa (putative MDR negative cell line), human lung carcinoma cell line A549 and hamster ovary CHO K1 cell line were cultured as described in the Example 1. All dyes stocks were prepared as described in Example 2. The following stocks of inhibitors in DMSO were prepared: 5 mM of cyclosporine A (general specificity inhibitor, 1000×), 5 mM of verapamil (MDR-specific inhibitor, 250×), 0.2 M of probenecid (MRP-specific inhibitor, 1000×), 10 mM of MK-571 (MRP-specific inhibitor, 200×), 0.5 M of novobiocin (BCRP-specific inhibitor, 10000×) and 10 mM of fumitremorgin C (BCRP-specific inhibitor, 1000×).

Cells were grown on tissue culture dishes and on the day of assay were trypsinized and washed twice with warm (37° C.) phosphate-buffered saline (PBS). Post-wash, the cells were re-suspended in warm phenol red indicator-free medium at a density of $1 \times 10^6$/ml. For each detection set, sixteen tubes (5 samples in triplicates plus non-stained control for background fluorescence) in numbered tubes each containing $5 \times 10^5$/cells (0.5 ml) were prepared. Warm medium (0.25 mL) containing different inhibitors [4 samples, one general inhibitor (5 µM of cyclosporine A) and three specific inhibitors (20 µM of verapamil, 0.2 mM of probenecid or 0.5 mM of novobiocin)] or vehicle only (1 sample) was added to each designated tube, and cells were mixed thoroughly with gentle pipeting. The non-stained control sample did not receive any inhibitor. After incubation for 5 min at 37° C., 0.25 ml of warm medium with Fluo-8™ AM probe (5 µM final concentration) or Rhod-4™ AM probe (2 µM final concentration) was added to each tube excluding non-stained control that receives plain medium and cells were incubated for 30 min at 37° C. and analyzed immediately by flow cytometry. In the second set of the tubes, the reaction was stopped by rapid centrifugation (1 min) at relatively low speed (200×g). After wash with ice-cold PBS and discarding the supernatant, cells were re-suspended in 0.5 ml of ice-cold medium and kept on ice until flow cytometry analysis. The third set of cells simply was spun down (1 min, 200×g) to remove the excess of the probe, resuspended in ice-cold medium and kept on ice until flow cytometry analysis.

Flow cytometry experiments were performed using a FACS Calibur benchtop flow cytometer (BD Biosciences) equipped with a blue (488 nm) laser, and the signals were registered in the FITC (530/30 filter), PE (585/42 filter) and PerCP (670 LP filter) channels. Fluo-8™ dye fluorescence was measured in the FL1 channel, and Rhod-4™ dye fluorescence—in the FL2 channel. Flow cytometry data were analyzed by comparison of median fluorescence or using Kolmogorov-Smirnov statistics [Young, J Histochem Cytochem 25:935-941 (1977)] or by calculating MAF values (MDR Activity Factor) using the following formula: $MAF=100*((MFI_{inh}-MFI_0)/MFI_{inh})$, where $MFI_{inh}$ and $MFI_0$ are mean fluorescence intensity values measured in the presence and absence of inhibitor [Hollo et al., Biochem Piophys Acta. 1191:384-388 (1994)].

Figures 1, 5:
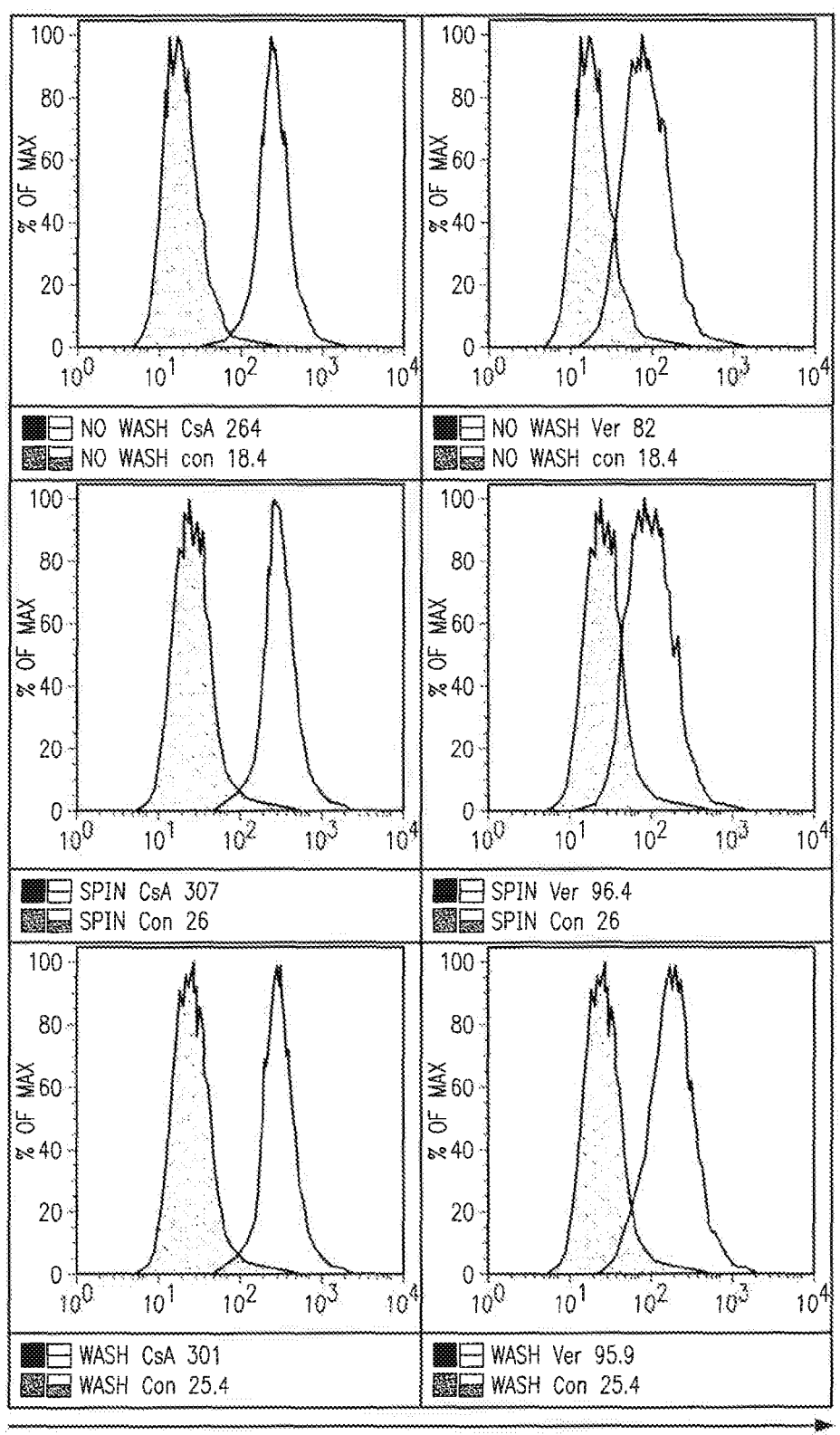
FIG. 1 is a table listing various dyes which have been used in MDR detection.
FIG. 5 illustrates results of optimization studies of dye uptake assays.
Figures 2, 5:
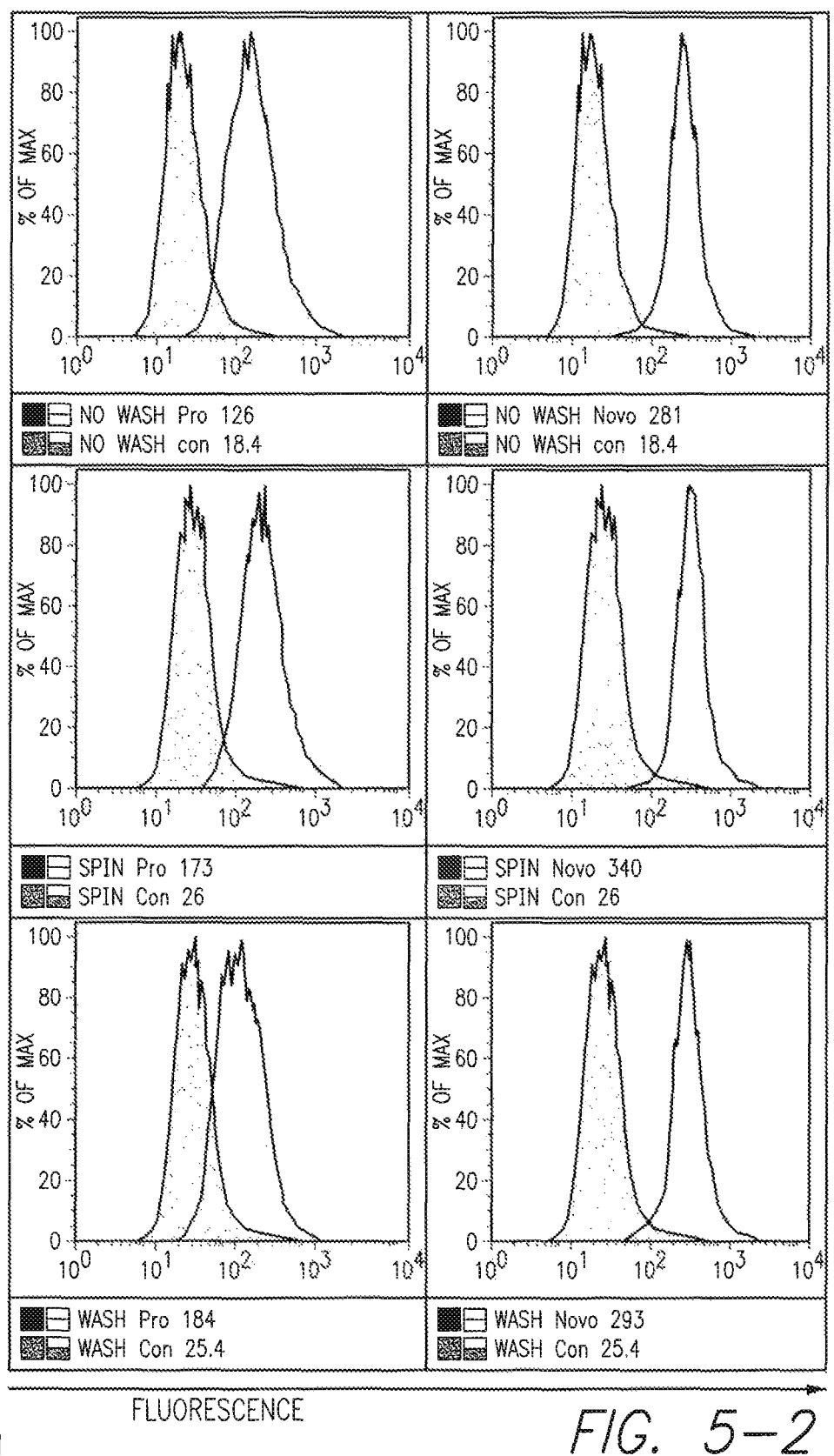

In Table 4 and FIG. 5, the results of a typical experiment with CHO K1 cell line and Fluo-8™ AM probe are presented.

TABLE 4

Optimization of the dye uptake protocol for the MDR assay, CHO K1 cell line, Fluo-8 ™ AM probe.

| Value | Protocol | Cyclosporin A | Verapamil | Probenecid | Novobiocin |
|---|---|---|---|---|---|
| MAP | No Wash | 93.0 | 77.6 | 85.4 | 93.5 |
|  | Spin | 91.5 | 73.0 | 85.0 | 92.4 |
|  | Wash | 91.6 | 73.5 | 86.2 | 91.3 |
| D-values | No Wash | 0.97 | 0.81 | 0.9 | 0.98 |
|  | Spin | 0.94 | 0.76 | 0.9 | 0.97 |
|  | Wash | 0.94 | 0.76 | 0.87 | 0.94 |

Experiments with another model cell line (A549) and with other tested probe (Rhod-4™ AM) demonstrated similar results that allow us to conclude that in the novel MDR detection assay, dye uptake protocol may be simplified and used without additional washing steps. In this case, however, the samples must be analyzed within a 30 min interval. If immediate flow cytometry assay is not possible, then washing and storing on ice is recommended, since according to literature reports, most of ABC transporters are inactive at +4° C.

Example 4

Development of the Minimal Step Assay Procedure for the Dye Efflux Flow Cytometry Protocol Human cervical adenocarcinoma epithelial cell line HeLa (putative MDR negative cell line), human lung carcinoma cell line A549 and hamster ovary CHO K1 cell line were cultured as described in the Example 1. All dyes and inhibitors stocks were prepared as described in Examples 2 and 3.

Cells were grown in tissue culture dishes and on the day of assay they were trypsinized and washed twice with ice-cold PBS. Post-wash, the cells were re-suspended in cold phenol red indicator-free medium at a density of $1 \times 10^6$/ml. For each detection set, eighteen tubes (6 tubes without inhibitor and 3 tubes for each inhibitor tested, in triplicates) each containing $2.5–5 \times 10^5$/cells were prepared. Cells were centrifuged at 200×g for 5 min, and after discarding supernatant, re-suspended at $1 \times 10^6$/ml in ice-cold indicator-free medium containing Fluo-8™ AM or Rhod-4™ AM probes. Additionally, an aliquot of non-stained cells was prepared for background fluorescence measurements. Cells were incubated with the probe(s) on ice for 60 min, than centrifuged at 200×g for 5 min. After discarding the supernatant, cells were either washed twice with PBS or simply were spun down to remove the excess of the probe and resuspended at $5 \times 10^5$ cells/sample in 0.5 ml of following solutions:

1. warm (37° C.) indicator-free medium containing vehicle only (3 tubes)
2. warm (37° C.) indicator-free medium containing inhibitor (3 tubes for each inhibitor tested)
3. ice-cold indicator-free medium (3 tubes)

Tube sets 1 and 2 were immediately transferred to a water bath (37° C.) and incubated for 90 min. Tube set 3 was kept on ice. Post incubation, 4 ml of ice-cold indicator-free medium was added per tube, tubes were centrifuged at 200×g for 5 min, supernatant was discarded, and cell pellet was re-suspended in the cold indicator-free medium and centrifuged again. Finally, cells were re-suspended in 0.5 ml of cold indicator-free medium and maintained on ice until analysis. Alternatively, cells were analyzed without washing. Flow cytometry experiments were performed as described in Example 3.

Figure 6:
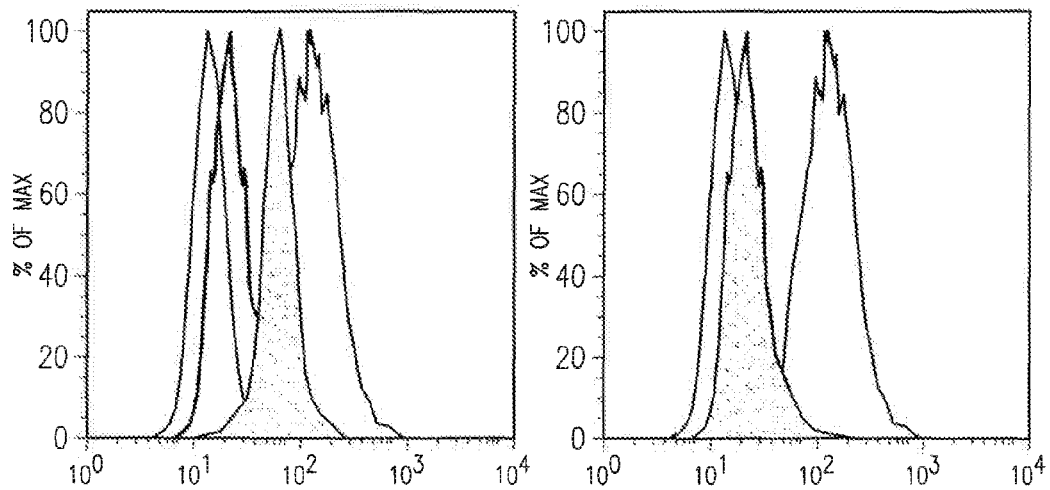
FIG. 6 illustrates results of optimization studies of dye efflux assays.
Figure 1:
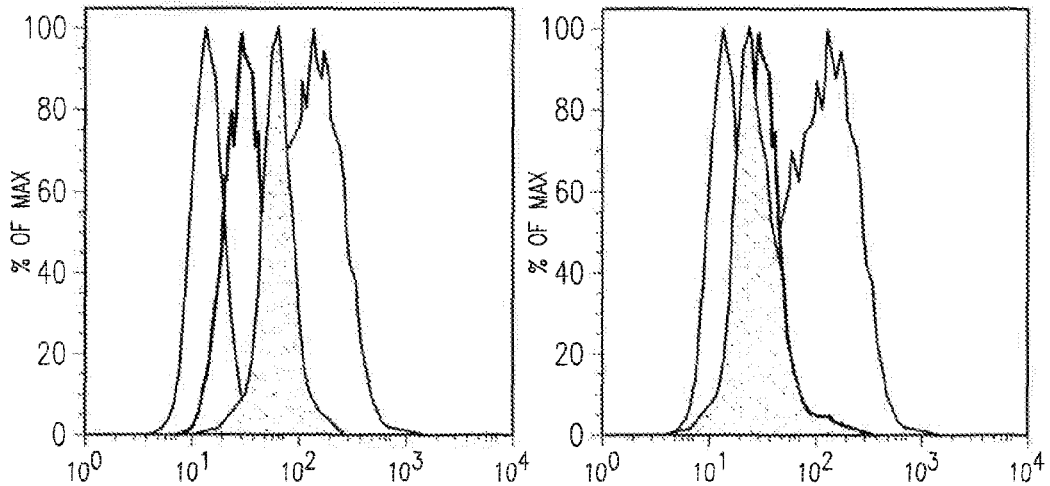
Figures 1, 7A:
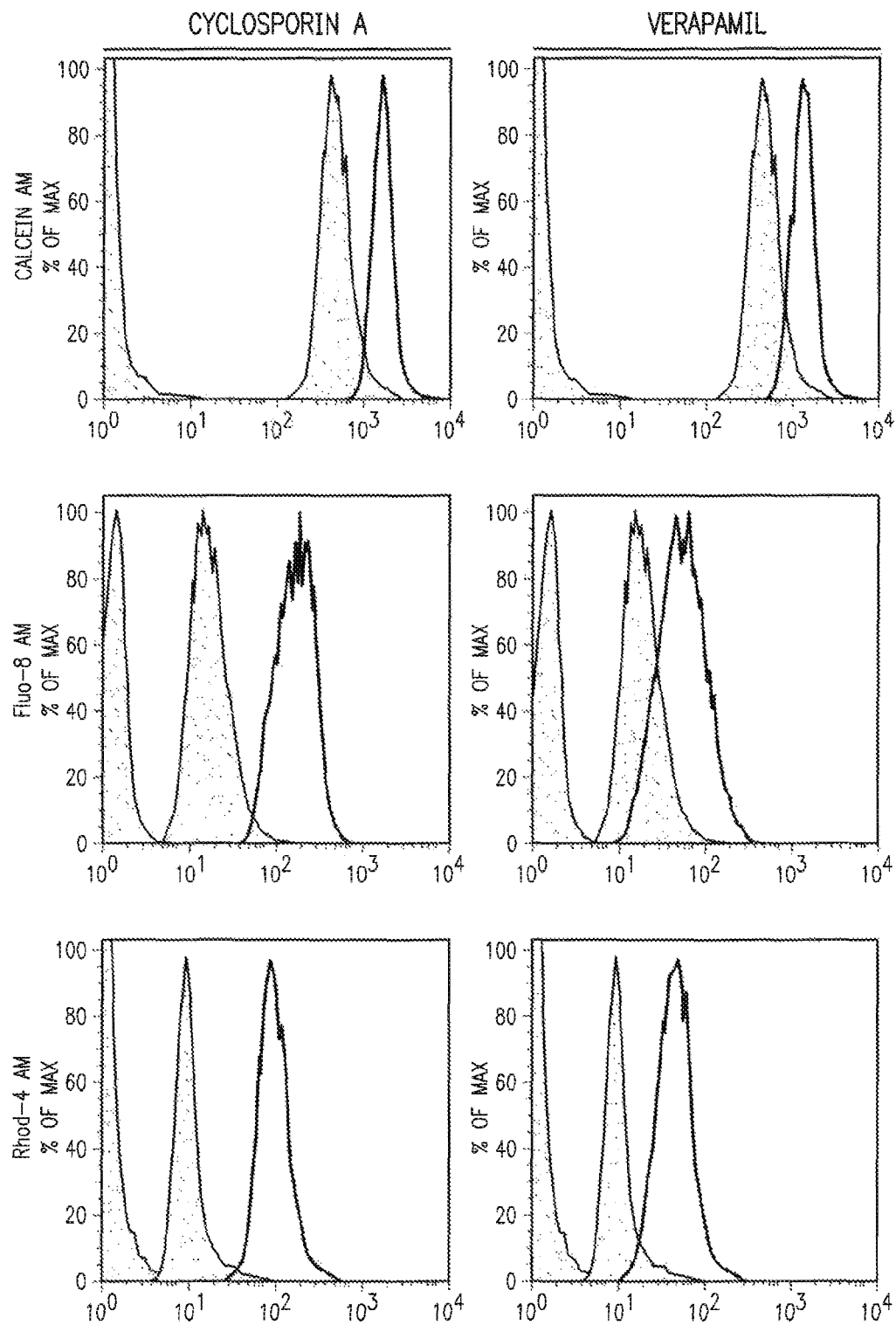
Figures 1, 2, 7A:
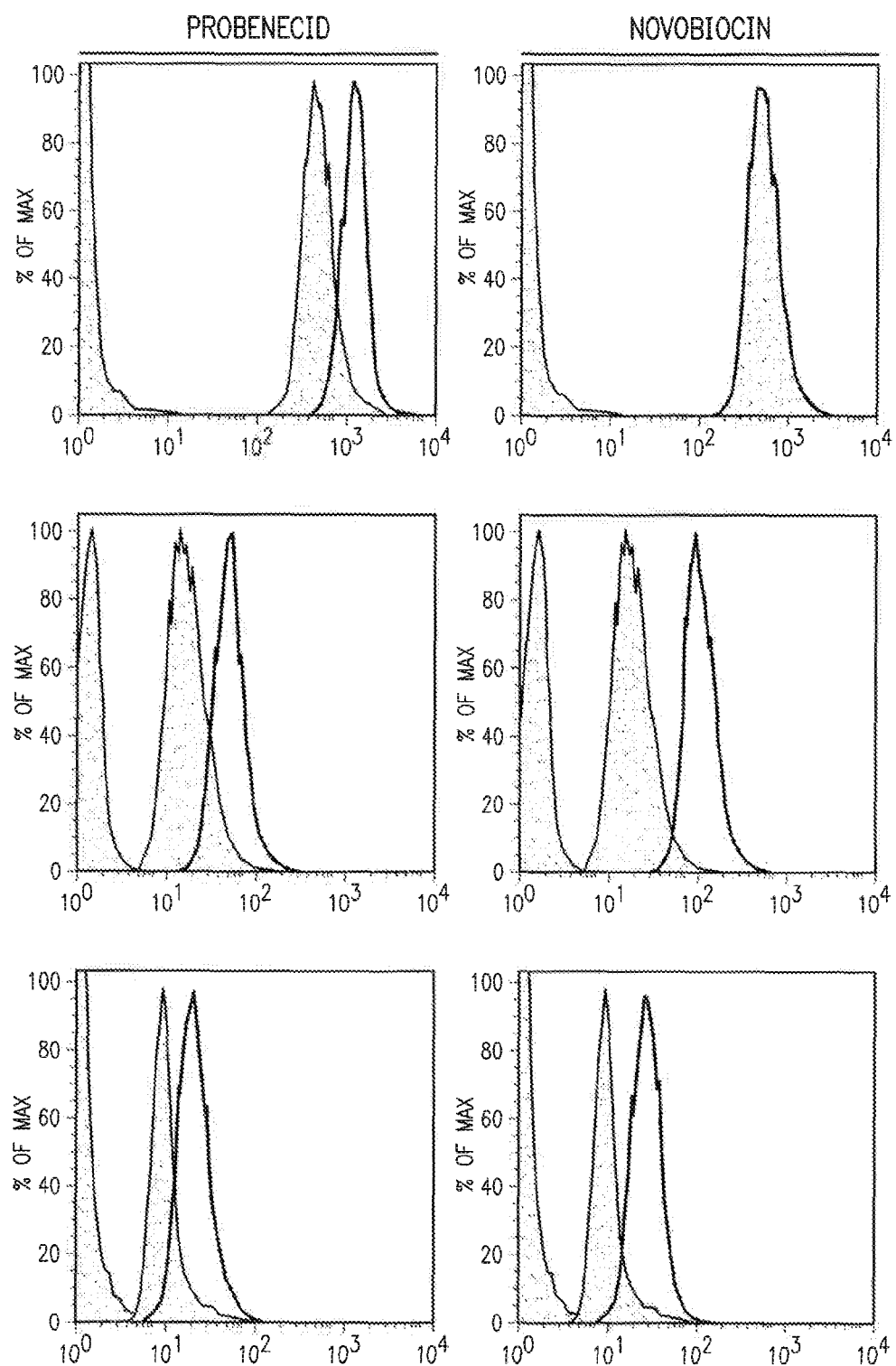
Figures 1, 2, 7B:
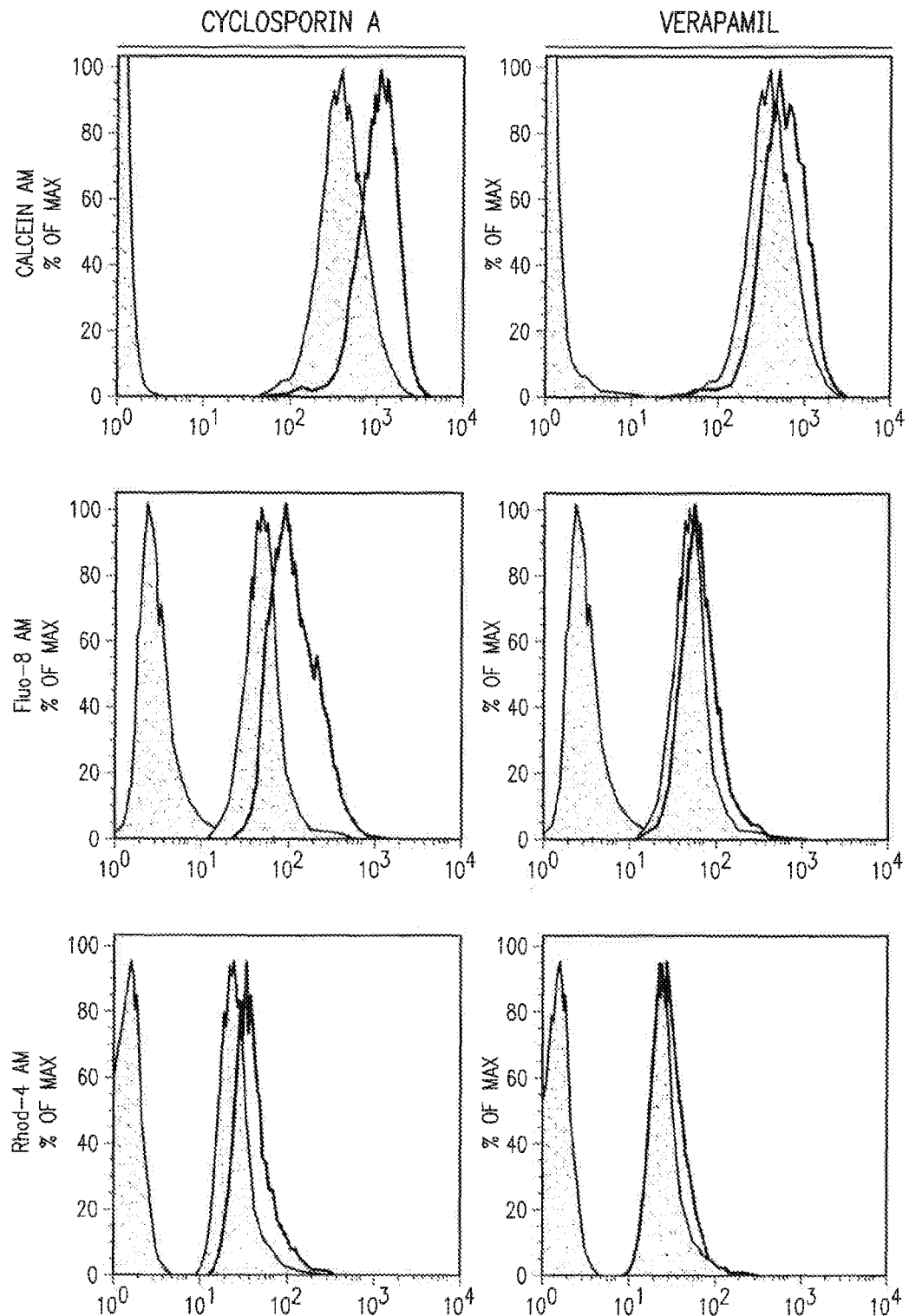
Figures 1, 2, 7B:
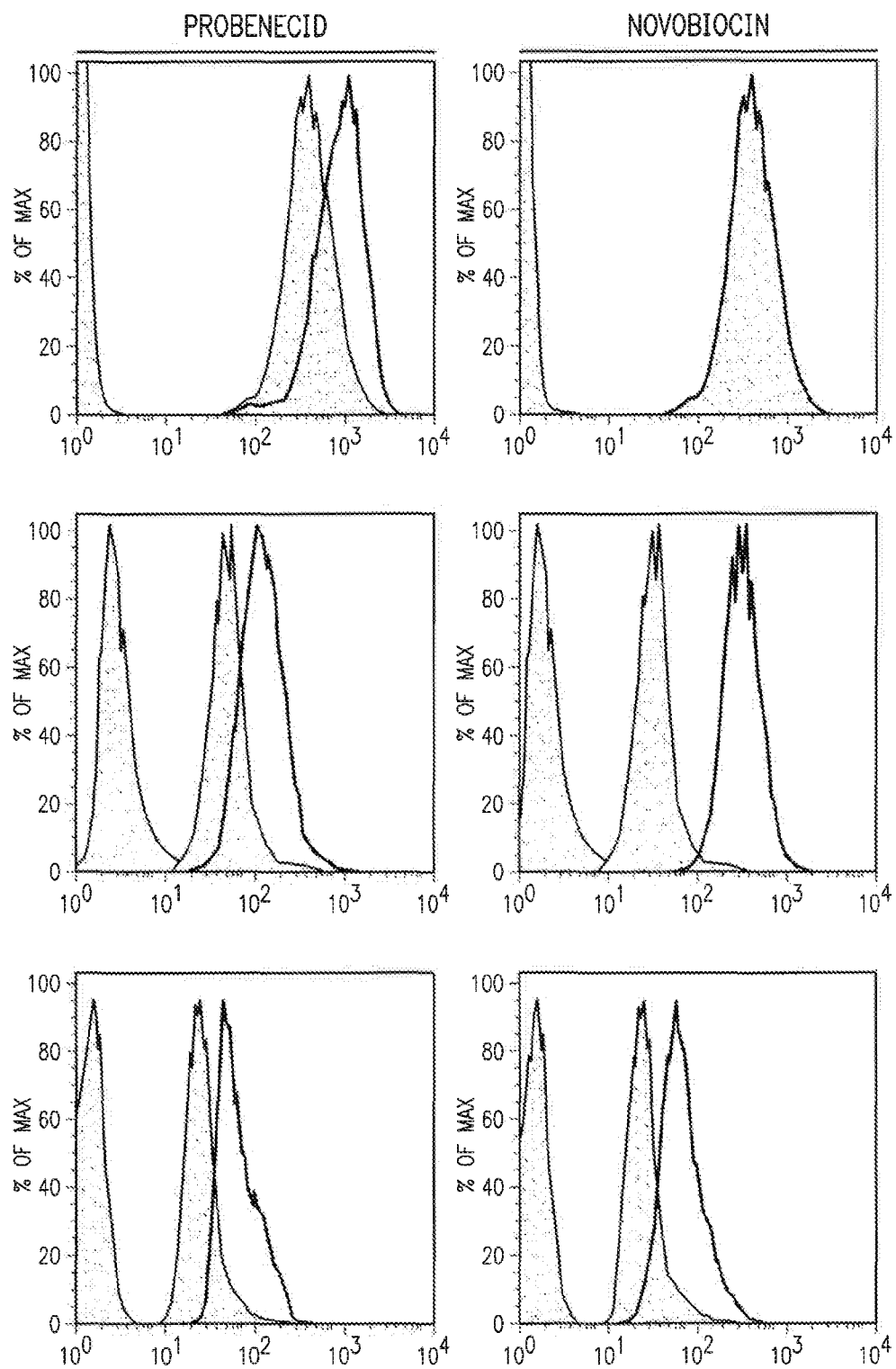
Figures 1, 7C:
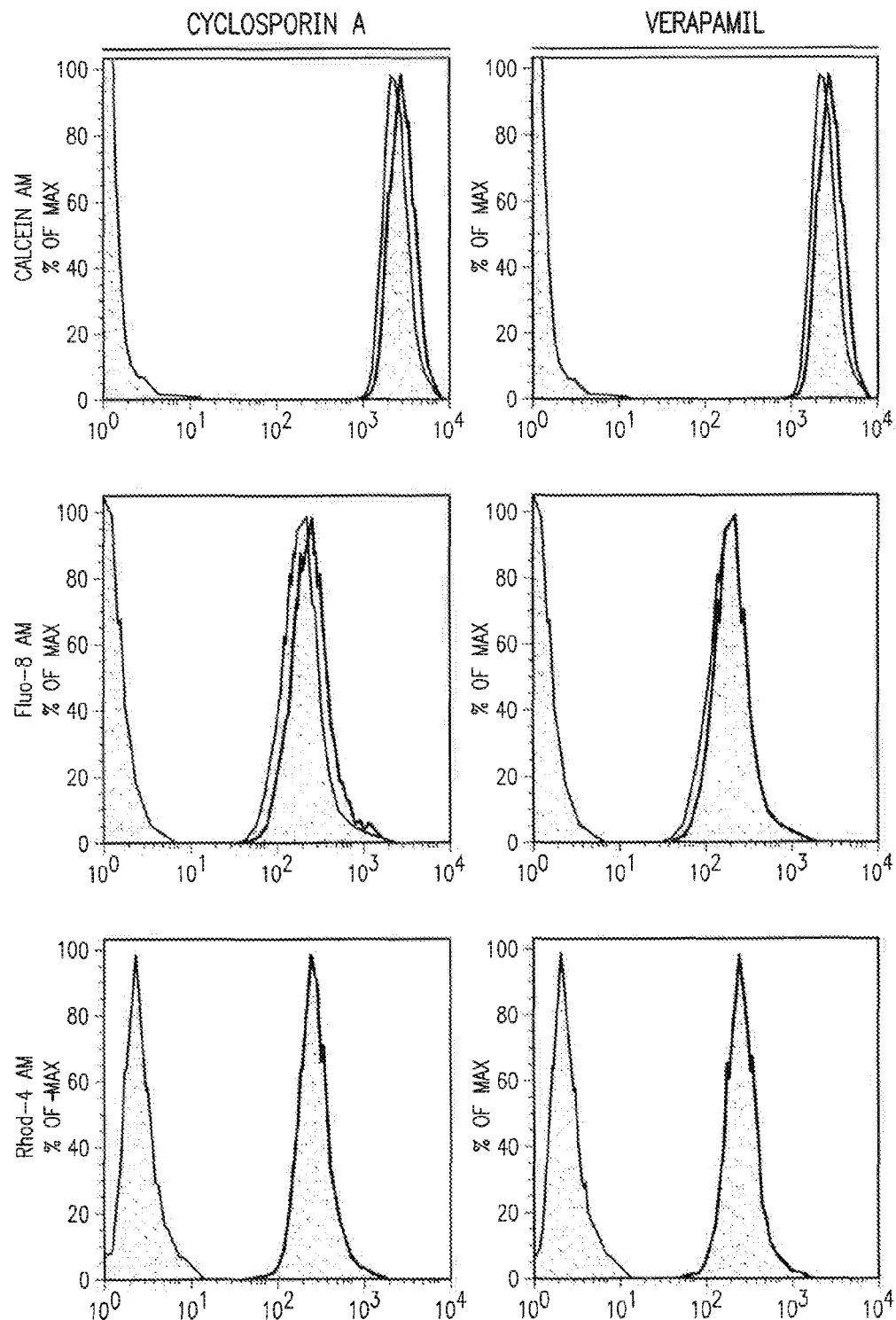
Figures 2, 7C:
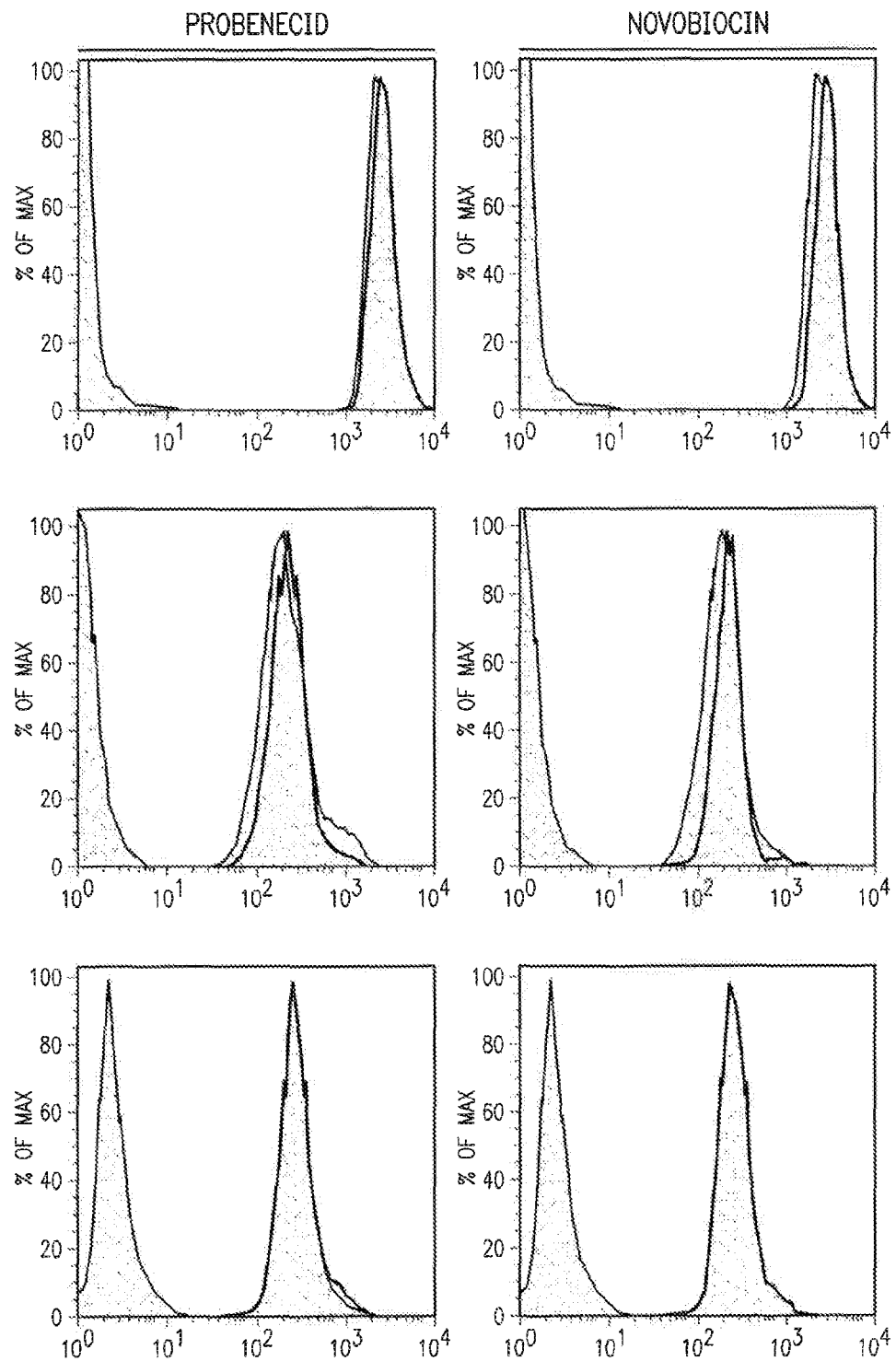

In Table 5 and FIG. 6, the results of representative experiments in model cell lines with Fluo-8™ AM probe are given.

TABLE 5

Optimization of the dye efflux protocol for the flow cytometry MDR assay using Fluo-8 ™ AM probe.
Kolmogorov-Smirnov statistical D-values are presented.

| Cell Line | Protocol | Cyclosporin A | Verapamil | Probenecid | Novobiocin | +4° C. |
|---|---|---|---|---|---|---|
| CHO K1 | No Wash | 0.8 | 0.21 | 0.19 | 0.7 | 0.78 |
|  | Wash | 0.62 | 0.34 | 0.23 | 0.79 | 0.76 |
| A549 | No Wash | 0.83 | 0.12 | 0.33 | 0.57 | 0.77 |
|  | Wash | 0.71 | 0.11 | 0.18 | 0.46 | 0.75 |
| HeLa | NoWash | 0.12 | 0.076 | 0.13 | 0.13 | 0.15 |
|  | Wash | 0.14 | 0.14 | 0.14 | 0.16 | 0.14 |

Qualitatively and quantitatively, variations of both protocols produce similar results. Additional washing step does not change the results of the assay significantly. For the efflux assay, the washing step increases the difference between control and inhibitor treated sample (probably because there is no dye excess and no passive transport through the membrane during ice incubation.

Example 5

Confirmation of Substrate Specificity of Fluo-8™ AM and Rhodamine-4™ AM Probes in Mammalian Cells Using Flow Cytometry Dye Uptake Protocol CHO K1, A 549 and HeLa cell lines were cultured as described in Example 1. Stock solutions of the probes and inhibitors were prepared as described in Examples 2 and 3. Additionally, stocks of the following dyes (that have been proven to be specific for particular ABC transporter detection) were made: 20 µg/ml of 3,3'-diethyloxacarbocyanine iodide [DiOC$_2$(3), 1000×], 10 mM of pheophorbide A (2000×) and 5 mM of chloromethylfluorescein diacetate (CMFDA, 1000×).

Cells were grown on tissue culture dishes and on the day of assay were treated according to a dye uptake protocol and analyzed by flow cytometry as described in Example 3. Calcein AM, DiOC$_2$(3), CMFDA and pheophorbide A were used as a control MDR probes with known substrate specificity. The specificity of the probes and D-values obtained as results of the test are listed in Table 5.

TABLE 5

Comparison of MDR activity detection in model cell lines using MDR probes and inhibitors of different specificity. Average D-values for three representative experiments are provided.

| Cell Line | MDR Probe | Probe Specificity | Verapamil | Probenecid | Fumitremorgin C |
|---|---|---|---|---|---|
| CHO K1 | Calcein AM | Pgp, MRP | 0.74 | 0.77 | 0.17 |
|  | Fluo-8 AM |  | 0.84 | 0.69 | 0.48 |
|  | Rhodamine-4 AM |  | 0.80 | 0.58 | 0.32 |
|  | DiOC$_2$(3) | Pgp | 0.96 | 0.01 | 0 |
|  | Pheophorbide A | BCRP | 0.02 | 0.03 | 0.25 |
|  | CMFDA | MRP | 0.19 | 0.7 | 0.09 |
| A549 | Calcein AM | Pgp, MRP | 0.17 | 0.36 | 0.04 |
|  | Fluo-8 AM |  | 0.07 | 0.26 | 0.23 |
|  | Rhodamine-4 AM |  | 0.14 | 0.21 | 0.29 |
|  | DiOC$_2$(3) | Pgp | 0.07 | 0 | 0.03 |
|  | Pheophorbide A | BCRP | 0.16 | 0.16 | 0.35 |
|  | CMFDA | MRP | 0.04 | 0.29 | 0.21 |

TABLE 5-continued

Comparison of MDR activity detection in model cell lines using MDR probes and inhibitors of different specificity. Average D-values for three representative experiments are provided.

| Cell Line | MDR Probe | Probe Specificity | Verapamil | Probenecid | Fumitremorgin C |
|---|---|---|---|---|---|
| HeLa | Calcein AM | Pgp, MRP | 0.17 | 0.06 | 0.03 |
| | Fluo-8 AM | | 0.10 | 0 | 0.15 |
| | Rhodamine-4 AM | | 0 | 0 | 0.10 |
| | DiOC$_2$(3) | Pgp | 0 | 0.06 | 0.07 |
| | Pheophorbide A | BCRP | 0 | 0 | 0 |
| | CMFDA | MRP | 0 | 0.03 | 0.12 |

Comparison of the data from TABLE 5 confirms that both Fluo-8™ AM and Rhodamine-4™ AM can specifically detect particular MDR activity when used with a corresponding modulator of ABC transporter activity. In CHO K1 cell line, Pgp expression was detected by all specific dyes and by Fluo-8™ and Rhodamine-4™; MRP expression was detected by all specific dyes and by Fluo-8™ and Rhodamine-4™; BCRP expression was detected by PheA, which is specific for this ABC transporter, and by Fluo-8™ and Rhodamine-4™. In A549 cell line, Pgp expression was not detected by any specific dye and not by Fluo-8™ and Rhodamine-4™; MRP expression was detected by all specific dyes and by Fluo-8™ and Rhodamine-4™; BCRP expression was detected by PheA, which is specific for this ABC transporter, and by FluoForte™ and Rhodamine-4™. In HeLa cell line, no drug resistance was detected with any dye/inhibitor combination. The data confirmed specificity of FluoForte™ and Rhodamine-4™ for all three major types of ABC transporter proteins.

Example 5A

Profiling of ABC Transporters in Mammalian Cells Using Fluo-8™ AM or Rhodamine-4™ AM Probes in Conjunction with Various Specific MDR Probes Using Flow Cytometry Dye Uptake Protocol CHO K1, cell line was cultured as described in Example 1. Stock solutions of the probes and inhibitors were prepared as described in Examples 2 and 3. Additionally, stocks of the following dyes (that have been proven to be specific for particular ABC transporter detection) were made: 20 μg/ml of 3,3'-diethyloxacarbocyanine iodide [DiOC$_2$(3), 1000×], 10 mM of pheophorbide A (2000×) and 5 mM of chloromethylfluorescein diacetate (CMFDA, 1000×).

Cells were grown in tissue culture dishes and on the day of assay were treated according to a dye uptake protocol and analyzed by flow cytometry as described in Example 3. Fluo-8™ AM, Rhodamine-4™ AM, DiOC$_2$(3) (MDR1-specific probe), CMFDA (MRP-specific probe) or pheophorbide A (BCRP-specific probe) were added to the cells alone or in combination (general+specific or general+two specific probes) allowing spectral resolution. The concentrations of the probes were as follows: Fluo-8™ AM—5 μM, Rhodamine-4™ AM—2 μM, DiOC$_2$(3)—20 ng/ml, CMFDA—1 μM, Pheophorbide A—5 μM.

Following 30 min incubation at 37° C., cells were analyzing by flow cytometry. Samples were collected as is (uncompensated) and double or triple stained samples were collected second time after compensation correction.

Pheophorbide A, which is specific for BCRP, was used in combination with either green (Fluo-8™ AM) or orange (Rhodamine-4™ AM) MDR general probe. In BCRP-expressing CHO K1 cells, fluorescence decreased in both channels (FL1 and FL3 or FL2 and FL3) if cyclosporin A (general MDR inhibitor) or fumitremorgin C (specific BCRP inhibitor) were not present (Table 6A below). Quantitative characteristics of the changes in fluorescence (expressed as D-values or as MAFs), corresponded to values obtained with single probes. It is important to note that in case of dual probe treatment with Rhodamine-4™ AM, compensation corrections are required to eliminate overlap of the dye spectra. In the cells that are BCRP-negative but positive for other types of ABC transporters, red fluorescence is high, while green or orange fluorescence is dim.

TABLE 6A

Examples of multiplex (dual) probe treatment for MDR activity profiling in CHO K1 cell line.
(D-values are provided as characteristics of MDR).

| Probes | Detection Channel | D-values Post Inhibitor Treatment (compared to uninhibited cells) | | | |
|---|---|---|---|---|---|
| | | CsA | Verapamil | MK-571 | FTC |
| Fluo-8 ™ AM | FL1 | 0.94 | 0.9 | 0.98 | 0.56 |
| Pheophorbide A | FL3 | 0.25 | 0.14 | 0.15 | 0.33 |
| Rhod-4 ™ AM | FL2 | 0.89 | 0.94 | 0.96 | 0.51 |
| Pheophorbide A | FL3 | 0.25 | 0.11 | 0.14 | 0.34 |
| Rhod-4 ™ AM | FL2 | 0.84 | 0.82 | 0.96 | 0.44 |
| DiOC$_2$(3) | FL1 | 0.94 | 0.96 | 0.13 | 0.16 |
| Rhod-4 ™ AM | FL2 | 0.9 | 0.94 | 0.85 | 0.53 |
| CMFDA | FL1 | 0.49 | 0.1 | 0.91 | 0.06 |

If DiOC$_2$(3) is used in combination with Rhodamine-4™ AM, in Pgp expressing cells, both dyes are pumped out in the absence of the inhibitors and cells exhibit less fluorescence in both the FL1 and FL2 channels. In MRP or BCRP expressing cells, only Rhodamine 4™ AM is pumped out in the absence of the inhibitors, and cells show lower fluorescence in the FL2 but not FL1 channel. According to these considerations, when both dyes were used in CHO K1 cell line, orange fluorescence was bright in all cases when cells were treated with the inhibitors, but green fluorescence was bright only in the presence of verapamil (Table 6A).

Chloromethylfluorescein diacetate (CMFDA) could also be used with Rhodamine-4™ AM in a two dye combination. In MRP expressing cells, both dyes would be pumped out in the absence of the inhibitors and cells would demonstrate a decreased fluorescence in both the FL1 and FL2 channels. In Pgp or BCRP expressing cells, only the Rhodamine 4™ AM would be pumped out and fluorescence will go down in the FL2 but not FL1 channel. Accordingly, in CHO K1 cells, orange fluorescence sustained bright when specific inhibitors were used, but green fluorescence was bright only when MRP inhibitor (MK-571) was applied.

For the triplex probe profiling, Rhodamine-4™ AM was employed as a general specificity probe, and DiOC$_2$(3), CMFDA and pheophorbide A was employed as specific probes (Table 6B).

TABLE 6B

Examples of multiplex (triple) probe treatment for MDR activity profiling in CHO K1 cell line.
(D-values are provided as characteristics of MDR).

| Probes | Detection Channel | D-values Post Inhibitor Treatment (compared to uninhibited cells | | | |
|---|---|---|---|---|---|
| | | CsA | Verapamil | MK-571 | FTC |
| $DiOC_2(3)$ | FL1 | 0.98 | 0.98 | 0.13 | 0.11 |
| Rhod-4 ™ AM | FL2 | 0.81 | 0.91 | 0.97 | 0.54 |
| Pheophorbide A | FL3 | 0.4 | 0.17 | 0.13 | 0.41 |
| CMFDA | FL1 | 0.47 | 0.10 | 0.89 | 0.14 |

TABLE 6B-continued

Examples of multiplex (triple) probe treatment for MDR activity profiling in CHO K1 cell line.
(D-values are provided as characteristics of MDR).

| Probes | Detection Channel | D-values Post Inhibitor Treatment (compared to uninhibited cells | | | |
|---|---|---|---|---|---|
| | | CsA | Verapamil | MK-571 | FTC |
| Rhod-4 ™ AM | FL2 | 0.93 | 0.97 | 0.95 | 0.64 |
| Pheophorbide A | FL3 | 0.20 | 0.18 | 0.09 | 0.27 |

When $DiOC_2(3)$ and pheophorbide A were used in CHO K1 cell line in conjunction with Rhodamine-4™ AM, FL2 (orange) fluorescence stays bright after treatment with all inhibitors used for the experiment. FL1 (green) fluorescence decreased unless cyclosporin A (general MDR inhibitor) or verapamil (MDR1 inhibitor) were present. FL3 (dark red) fluorescence was bright only when cyclosporin A (general MDR inhibitor) or fumitremorgin C (BCRP inhibitor) were present.

Similarly, with the combination of Rhodamine-4™ AM, CMFDA and pheophorbide A, FL2 (orange) fluorescence stays bright after treatment with all inhibitors used for the experiment. FL1 (green) fluorescence decreased unless cyclosporin A (general MDR inhibitor) or MK-571 (MRP inhibitor) were present. FL3 (dark red) fluorescence was bright only when cyclosporin A (general MDR inhibitor) or fumitremorgin C (BCRP inhibitor) were present.

Some additional examples of multiplexed (two or more probes) MDR probes combinations and expected results of the assay are presented in the following Table 6C.

TABLE 6C

Expected results of multiplex probing for MDR activity detection

| Set | Fluorogenic Probe | Specificity | Decreased Fluorescence in the Absence of the Inhibitors, If cells have active | | |
|---|---|---|---|---|---|
| | | | MDR | MRP | BCRP |
| A | Fluo-8 ™ AM<br>Pheophorbide A | general<br>BCRP | FL1 | FL1 | FL1 + FL3 |
| B | Fluo-8 ™ AM<br>Fura-2 AM<br>BODIPY-Prazozin | general<br>Pgp<br>BCRP | FL1 + UV | FL1 | FL1 + FL3 |
| C | Fluo-8 ™ AM<br>Hoechst 33342 | general<br>BCRP | FL1 | FL1 | FL1 + UV |
| D | Fluo-8 ™ AM<br>TMRM | general<br>MRP | FL1 | FL1 + FL3 | FL1 |
| E | Fluo-8 ™ AM<br>monobromobimane<br>Pheophorbide A | general<br>MRP<br>BCRP | FL1 | FL1 + UV | FL1 + FL3 |
| F | Fluo-8 AM<br>BODIPY-Taxol | general<br>Pgp | FL1 + FL3 | FL1 | FL1 |
| G | Rhodamine-4 ™ AM<br>CMFDA | general<br>MRP | FL2 | FL1 + FL2 | FL2 |
| H | Rhodamine-4 ™ AM<br>$DiOC_2(3)$ | general<br>Pgp | FL1 + FL2 | FL2 | FL2 |
| I | Rhodamine-4 ™ AM<br>$DiOC_2(3)$<br>Pheophorbide A | general<br>Pgp<br>BCRP | FL1 + FL2 | FL2 | FL2 + FL3 |
| J | CMFDA<br>Rhodamine-4 ™ AM<br>Pheophorbide A | MRP<br>general<br>BCRP | FL2 | FL1 + FL2 | FL2 + FL3 |

Example 6

Detection of ABC Transporter Activity in Cancer Cells by Flow Cytometry Using Fluo-8™ AM and Rhod-4™ AM Probes and a Dye Uptake Protocol CHO K1, A 549 and HeLa cell lines were cultured as described in Example 1. Stock solutions of the probes and inhibitors were prepared as described in Examples 2 and 3. Cells were grown on tissue culture dishes and on the day of assay were treated according to a dye uptake protocol and analyzed by flow cytometry as described in Example 3. Calcein AM was used as a control MDR probe.

In FIG. 7, the results of MDR activity assays using Fluo-8™ AM, Rhod-4™ AM and Calcein AM in model cell lines are presented (representative experiment). Fluorescence profiles for cells treated with inhibitors are shown in bold, and fluorescence profiles for the cells that were untreated are shown as, filled histograms. As shown in FIG. 7, all three dyes detect similar P-gp and MRP levels in CHO K1 cells (Panel A), and detect only MRP but not P-gp in A549 cells (panel B). In contrast to Calcein AM, which is not able to detect BCRP activity, Fluo-8™ AM and Rhod-4™ AM detect significant BCRP activity in both CHO K1 and A549 cell lines. Results obtained with Fluo-8™ and Rhod-4™ dyes correspond to MTT chemoresistance data (FIGS. 3A-D) and to the published data [Ling et al., Cancer Treat Rep 67:869-874 (1983); Scharenberg et al., Blood 99:507-512 (2002); Gupta et al., Biochem Biophys Res Comm 153:598-605 (1988)]. All three probes do not detect any MDR activity in HeLa cells, which are considered to be MDR-negative cells (FIG. 7C).

TABLE 7

Detection of MDR activity by flow cytometry method (dye uptake) in model cell lines. Activity of ABC transporters is expressed as D-values.

| Cell Line | Probe | Cyclosporine A | Verapamil | Probenecid | Novobiocin |
|---|---|---|---|---|---|
| CHO K1 | Calcein AM | 0.96 | 0.93 | 0.70 | 0.06 |
|  | Fluo-8 ™ AM | 0.96 | 0.83 | 0.89 | 0.78 |
|  | Rhod-4 ™ AM | 0.96 | 0.89 | 0.74 | 0.80 |
| A549 | Calcein AM | 0.47 | 0.15 | 0.27 | 0.03 |
|  | Fluo-8 ™ AM | 0.51 | 0.09 | 0.49 | 0.44 |
|  | Rhod-4 ™ AM | 0.42 | 0.12 | 0.28 | 0.40 |
| HeLa | Calcein AM | 0.14 | 0.13 | 0.09 | 0.09 |
|  | Fluo-8 ™ AM | 0.14 | 0.04 | 0.15 | 0.09 |
|  | Rhod-4 ™ AM | 0.05 | 0.04 | 0.03 | 0.06 |

Example 7

Detection of ABC Transporter Activity in Cancer Cells by Flow Cytometry Using a Dye Efflux Protocol CHO K1, A 549 and HeLa cell lines were cultured as described in Example 1. Stock solutions of the probes and inhibitors were prepared as described in Examples 2 and 3. Cells were grown on tissue culture dishes and on the day of assay were treated according to a dye efflux protocol and analyzed by flow cytometry as described in Example 4. Calcein AM was used as a control MDR probe.

TABLE 8

Detection of MDR activity by flow cytometry method (dye efflux) in cultured cell lines (representative experiment). Activity of ABC transporters is expressed as D-values.

| Cell Type | MDR Probe | Cyclosporin A | Verapamil | Probenecid | Novobiocin | 4° C. |
|---|---|---|---|---|---|---|
| CHO K1 | Calcein AM | 0.31 | 0.26 | 0.47 | 0.13 | 0.65 |
|  | Fluo-8 ™ AM | 0.55 | 0.28 | 0.30 | 0.70 | 0.72 |
|  | Rhod-4 ™ AM | 0.52 | 0.33 | 0.21 | 0.64 | 0.45 |
| A549 | Calcein AM | 0.35 | 0.03 | 0.40 | 0.15 | 0.50 |
|  | Fluo-8 ™ AM | 0.5 | 0.02 | 0.33 | 0.57 | 0.80 |
|  | Rhod-4 ™ AM | 0.27 | 0.1 | 0.32 | 0.58 | 0.65 |
| HeLa | Calcein AM | 0.08 | 0.1 | 0.62 | 0.04 | 0.07 |
|  | Fluo-8 ™ AM | 0.13 | 0.15 | 0.16 | 0.15 | 0.83 |
|  | Rhod-4 ™ AM | 0 | 0 | 0 | 0 | 0.39 |

Data from the representative experiments included in Tables 7 and 8 demonstrated that the values obtained with Fluo-8™ AM and Rhod-4™ AM are equal to or higher than Calcein AM-based values indicating higher sensitivity of these probes Example 8

Fluo-8™ AM and Rhod-4™ AM Probes are More Sensitive for MDR Activity Detection than Commonly Used Probes of General Specificity, Such as Mitoxantrone and Doxorubicin CHO K1, A 549 and HeLa cell lines were cultured as described in Example 1. Stock solutions of the probes and inhibitors were prepared as described in Examples 2 and 3. Additionally, stock solutions of mitoxantrone (10 mM, 1000×) and doxorubicin (5 mM, 1000×) in DMSO were prepared, aliquoted and stored frozen at −20° C. in the dark. Sensitivity and specificity of Fluo-8™ AM, Rhod-4™ AM, mitoxantrone and doxorubicin were analyzed and compared using three model cell lines. Cells were grown in tissue culture dishes and on the day of assay were treated according to a dye uptake protocol and analyzed by flow cytometry, as described in Example 3. The results of the assay are presented in the FIG. 8 (representative experiment) and Table 9 (average D-values from three independent experiments are presented). All four probes are capable of the detection of all three major types of ABC transporters, however the Fluo-8 and Rhod-4 dyes generate higher intensity fluorescence, indicating they are capable of providing more sensitive detection of MDR.

TABLE 9

Sensitivity of MDR probes of general specificity in the drug uptake assay

| Cell Line | Probe | Cyclosporin A | Verapamil | MK-571 | Novobiocin | FTC |
|---|---|---|---|---|---|---|
| CHO K1 | Fluo-8 ™ AM | 0.89 | 0.74 | 0.95 | 0.68 | 0.28 |
|  | Rhod-4 ™ AM | 0.95 | 0.75 | 0.96 | 0.64 | 0.32 |
|  | Mitoxantrone | 0.34 | 0.42 | 0.18 | 0.22 | 0.21 |
|  | Doxorubicin | 0.42 | 0.27 | 0.35 | 0.32 | 0.22 |
| A549 | Fluo-8 ™ AM | 0.43 | 0.06 | 0.61 | 0.37 | 0.31 |
|  | Rhod-4 ™ AM | 0.35 | 0.09 | 0.48 | 0.41 | 0.38 |
|  | Mitoxantrone | 0.27 | 0.12 | 0.37 | 0.28 | 0.28 |
|  | Doxorubicin | 0.14 | 0.06 | 0.24 | 0.28 | 0.18 |

Example 9

Testing MDR Activity of Diverse Human Carcinoma Cell Lines Using Fluo-8™ AM and Rhod-4™ AM Probes Both human ileocecal colorectal carcinoma cell line HCT-8 (reported to over-express P-gp and, to a lesser extent, MRP [Hunter et al., Br J Cancer. 64:437-444 (1991); Collington et al., Biochem Pharmacol 44:417-424 (1992)] and hepatocellular carcinoma Hep G2 (reported to over-express MRP [Roelofsen et al., Gastroenterology 112:511-521 (1997), Cantz et al., Am J Physiol Gastrointest Liver Physiol. 278: G522-G531 (2000)] were obtained from ATCC. HCT-8 cells were routinely cultured in RPMI-1640 Medium with 2 mM L-glutamine, 10 mM HEPES, 1 mM sodium pyruvate, 4.5 g/L glucose, 1.5 g/L sodium bicarbonate (ATCC), supplemented with 10% horse serum (ATCC) and 100 U/ml penicillin, 100 ug/ml streptomycin (Sigma-Aldrich, St. Louis, Mo.). Hep G2 cells were routinely cultured in Eagle's Minimum Essential Medium with low glucose (ATCC), supplemented with 10% heat inactivated fetal bovine serum (ATCC) and 100 U/ml penicillin, 100 ug/ml streptomycin (Sigma-Aldrich, St. Louis, Mo.). Cell cultures were maintained in a humidified incubator at 37° C., with 5% $CO_2$ atmosphere. Stock solutions of the probes and inhibitors were prepared, as described in Examples 2 and 3. Cells were grown in tissue culture dishes and on the day of assay were treated according to a dye uptake protocol and analyzed by flow cytometry, as described in Example 3.

According to the data presented in FIG. 9, both Fluo-8™ AM and Rhod-4™ AM probes detect increased P-gp and MRP activity in HCT-8 cells (panel A) and increased MRP activity in Hep G2 cells (panel B). Comparison of D-values confirmed activity of P-gp in HCT-8 cells and of MRP in both cell lines tested.

TABLE 10

Results of detection of MDR activity of HCT-8 and Hep G2 cancer cell lines. D-values presented.

|  |  | Cyclosporin A | Verapamil | MK-571 | Novobiocin |
|---|---|---|---|---|---|
| HCT-8 | Fluo-8 ™ AM | 0.68 | 0.71 | 0.34 | 0.22 |
|  | Rhod-4 ™ AM | 0.72 | 0.51 | 0.27 | 0.061 |
|  | Calcein ™ AM | 0.31 | 0.71 | 0.16 | 0.44 |
| Hep G2 | Fluo-8 ™ AM | 0.28 | 0 | 0.34 | 0.13 |
|  | Rhod-4 ™ AM | 0.26 | 0 | 0.34 | 0 |
|  | Calcein ™ AM | 0.29 | 0.13 | 0.29 | 0.02 |

Example 10

Compatibility of Fluo-8™ AM and Rhod-4™ AM Probes with Propidium Iodide (PI), the Most Common Dead Cell Indicator Stain CHO K1 cell line was cultured as described in Example 1. Stock solutions of the probes and inhibitors were prepared as described in Examples 2 and 3. PI stock was made in water (100 µg/mL, 100×). Cells were grown on tissue culture dishes and on the day of assay were treated according to a dye uptake protocol. After 30 min incubation with probe and with/without inhibitors, PI was added to each sample to the final concentration 1 µg/mL and samples were analyzed by flow cytometry as described in Example 3. Single stained samples (PI only, Fluo-8™ AM only and Rhod-4™ only) were made to validate data obtained with two dyes. Data were collected uncompensated, also compensation corrections were performed using unstained cells, PI only stained dead cells and Fluo-8™ AM or Rhod-4™ stained cells (in the presence of cyclosporine A or MK-571 that provide a bright fluorescent signal).

affect determination of the number of dead cells in the sample. In certain cases (when the combination of Rhod-4™ AM and PI is used, and inhibitor treatment leads to a significant orange fluorescence increase), compensation corrections are needed in order to avoid overestimating dead cell staining.

Example 11

Multiplexed MDR Detection Using by Flow Cytometry in U-2 OS Cells Expressing Green Fluorescent Proteins U-2 OS human bone osteosarcoma cells were obtained from ATTC, and U-2 OS cells expressing green fluorescent mitochondria were obtained from Marinpharm GmbH, Germany and routinely cultured in McCoy's 5a Modified Medium (ATCC), supplemented with 10% fetal bovine serum heat inactivated (ATCC) and 100 µm! penicillin, 100 ug/ml streptomycin (Sigma-Aldrich). Cell cultures were maintained in an incubator at 37° C., with 5% $CO_2$ atmosphere. All dye and inhibitor stocks were prepared as described in Example 1.

Cells were grown on tissue culture dishes and on the day of assay they were trypsinized and washed twice with warm (37° C.) PBS. Post-wash, the cells were re-suspended in warm indicator-free medium at a density of $1\times10^6$/ml. For each detection set, sixteen tubes (5 samples in triplicates plus non-stained control for background fluorescence) in numbered tubes, each containing $5\times10^5$/cells (0.5 ml) were prepared. Warm medium (0.25 mL) containing different inhibitors (4 samples, one general inhibitor and three specific inhibitors) of vehicle only (1 sample) was added to each designated tube, and cells were mixed thoroughly with gentle pipeting. Non-stained control cells did not receive any inhibitor. After incubation for 5 min at 37° C., 0.25 ml of warm medium with Fluo-8 AM or Rhod-4™ AM probes (5 µM or 2 µM final concentration, for parental cells) or Rhod-4™ dye (2 µM final concentration, for green mitochondria expressing cells) were added to each tube excluding non-stained control that receives plain medium and cells were incubated for 30 min at 37° C. and analyzed immediately by flow cytometry using FACS Calibur benchtop cytometer (B D Dickinson, CA). To exclude dead cells, propidium iodide (PI) solution was added to the cells during the last 5 min of incubation (final concentration is 1 µg/mL). Fluo-8™ dye fluorescence

TABLE 11

Compatibility of Fluo-8 ™ AM and Rhod-4 ™ AM with propidium iodide. D-values for MDR activity and percentage of PI-positive cells are presented.

|  | Fluo-8 ™, | Uncompensated data | | | | | Compensated Data | |
|---|---|---|---|---|---|---|---|---|
|  |  | F8 + PI | | | R4 + PI | | R4 + PI | |
| Inhibitors | D | D-values | % $PI_{pos}$ | Rhod4 ™ | D-values | % $PI_{pos}$ | D-values | % $PI_{pos}$ |
| Cyclosporin A | 0.91 | 0.96 | 1.44 | 0.98 | 0.98 | 4.2 | 0.97 | 0.59 |
| Verapamil | 0.92 | 0.94 | 0.83 | 0.94 | 0.96 | 2.75 | 0.95 | 0.88 |
| MK-571 | 0.89 | 0.92 | 0.97 | .94 | 0.95 | 6.72 | 0.94 | 1.46 |
| Novobiocin | 0.54 | 0.61 | 0.83 | .64 | 0.7 | 1.61 | 0.66 | 0.81 |

Data presented in Table 11, clearly demonstrate that use of PI does not affect MDR detection when AM esters of Fluo-8™ and Rhod-4™ are used as probes. In turn, green or orange fluorescence resulting from the MDR detection does not was measured in the FL1 channel, Rhod-4™ dye fluorescence—in the FL2 channel, and PI fluorescence in the FL3 channel. Single stained samples of parental U-2 OS cells were prepared with each used dye for compensation correction.

TABLE 12

Comparison of the MDR activity data (expressed as MAF values) obtained using Fluo-8 ™ AM and Rhod-4 ™ AM as probes in U-2 OS cells

| | U-2 OS Dyes | | | | | | |
|---|---|---|---|---|---|---|---|
| | F8 | F8 + PI | | R4 | R4 + PI | | R4 + PI Compens |
| Inhibitors | MAF | MAF | % $PI_{pos}$ | MAF | MAF | % $PI_{pos}$ | MAF | % $PI_{pos}$ |
| CsA | 68.8 | 42.6 | 4.58 | 44.1 | 35.8 | 4.8 | 47.4 | 2.04 |
| FTC | 5.0 | −6.3 | 2.94 | 9.9 | −9.3 | 3.19 | 12.6 | 2.01 |
| MK | 65.4 | 52.9 | 4.19 | 62.8 | 49.7 | 4.28 | 54.5 | 1.8 |
| Novo | 17.9 | 12.3 | 3.29 | 18.7 | 10.7 | 2.69 | 15.1 | 1.31 |
| Pro | 57.5 | 23.1 | 4.21 | 41.2 | 24.0 | 3.46 | 42.4 | 1.05 |
| Ver | 63.4 | 33.0 | 3.62 | 42.5 | 35.8 | 3.65 | 54.1 | 1.51 |

TABLE 12B

Comparison of the MDR activity data (expressed as MAF values) obtained using Fluo-8 ™ AM and Rhod-4 ™ AM as probes in U-2 OS cells expressing GFP

| | U-2 OS GFP | | | | |
|---|---|---|---|---|---|
| Dyes | R4 | R4 + PI | | R4 + PI compens | |
| Inhibitors | MAF | MAF | % $PI_{pos}$ | MAF | % $PI_{pos}$ |
| CsA | 37.7 | 42.0 | 2.2 | 47.9 | 2.96 |
| FTC | 15.0 | 25.7 | 3.18 | 6.2 | 3.7 |
| MK | 49.6 | 51.9 | 3.08 | 43.3 | 3.92 |
| Novo | 17.9 | 27.9 | 2.09 | 2.8 | 2.66 |
| Pro | 34.0 | 47.7 | 2.09 | 38.5 | 2.92 |
| Ver | 30.4 | 41.3 | 2.77 | 38.0 | 3.31 |

Experiment conducted with GFP-expressing U-2 OS cells stained with Rhod-4™ probe and PI demonstrated feasibility of MDR activity detection in such systems. Compensation corrections are needed, however, for correct estimation of PI positive cells. PI fluorescence (red) does not interfere significantly with green and orange signal. Green signal does not affect red fluorescence, either. Orange fluorescence affects PI measurements significantly, however (particularly, when the inhibition of MDR is seen and orange signal increased significantly). These samples stained with Rhod-4™ and PI need compensation correction. Recommendations are to have single stained samples for each dye and unstained cells. Nevertheless, results obtained for the MDR activity do not depend on compensation correction in all cases.

Example 12

Detection of ABC Transporters' Activity in Cancer Cells Using Fluorescence Microplate Reader CHO K1, A 549 and HeLa cell lines were cultured as described in Example 1. Stock solutions of the probes and inhibitors were prepared as described in Examples 2 and 3. Two protocols (using cells in suspension and using adherent cells) were used. A. For the first protocol (suspension cells), cells in suspension (0.54×10⁵ cells/100 μL) were added to the wells of 96-well black walled microplates where 50 μL of reference or experimental MDR modulators/inhibitors were distributed (PBS was used as a control), mixed and incubated at 37° C. for 15 min. Fifty μL of 20 μM Fluo-8™ AM, 8 μM Rhod-4™ AM or 2 μM Calcein AM (used as a control MDR probe) were added to each well, mixed and incubated at 37° C. for 15 min. After the incubation, plates were centrifuged (5 min, 200×g), the supernatant was removed, the cells were resuspended in 200 μL of cold tissue culture medium and retained fluorescence was measured. Optionally, cells were washed with cold PBS after staining.

B. For the adherent cells, cells were seeded in black walled 96-well microplates (2–5×10⁴ cells/well) and 24 h later were treated with the inhibitors (or vehicle) and stained with the probes (5 μM of Fluo-8™ AM, 2 μM of Rhod-4™ AM or 0.5 μM of Calcein AM final concentration) for 30 min at 37° C. Then the fluorescence was measured immediately or after excess dye(s) was removed by washing with HBSS (inhibitors should be added to the washing buffer to avoid artifacts).

The probe(s) retention was measured using an OPTIMA FluoStar multiplate fluorimeter (BMG Labtech Inc., NC; equipped with 490 and 550 nm excitation filter and 520 and 570 nm emission filters) or Synergy™ Mx multi-mode microplate reader (BioTek Instruments Inc., VT; using 490 and 530 nm excitation and 520 and 555 nm emission settings). The results of the assay were expressed as a ratio of the fluorescence of the inhibitor-treated cells to the fluorescence of the untreated control cells.

Figure 10A:
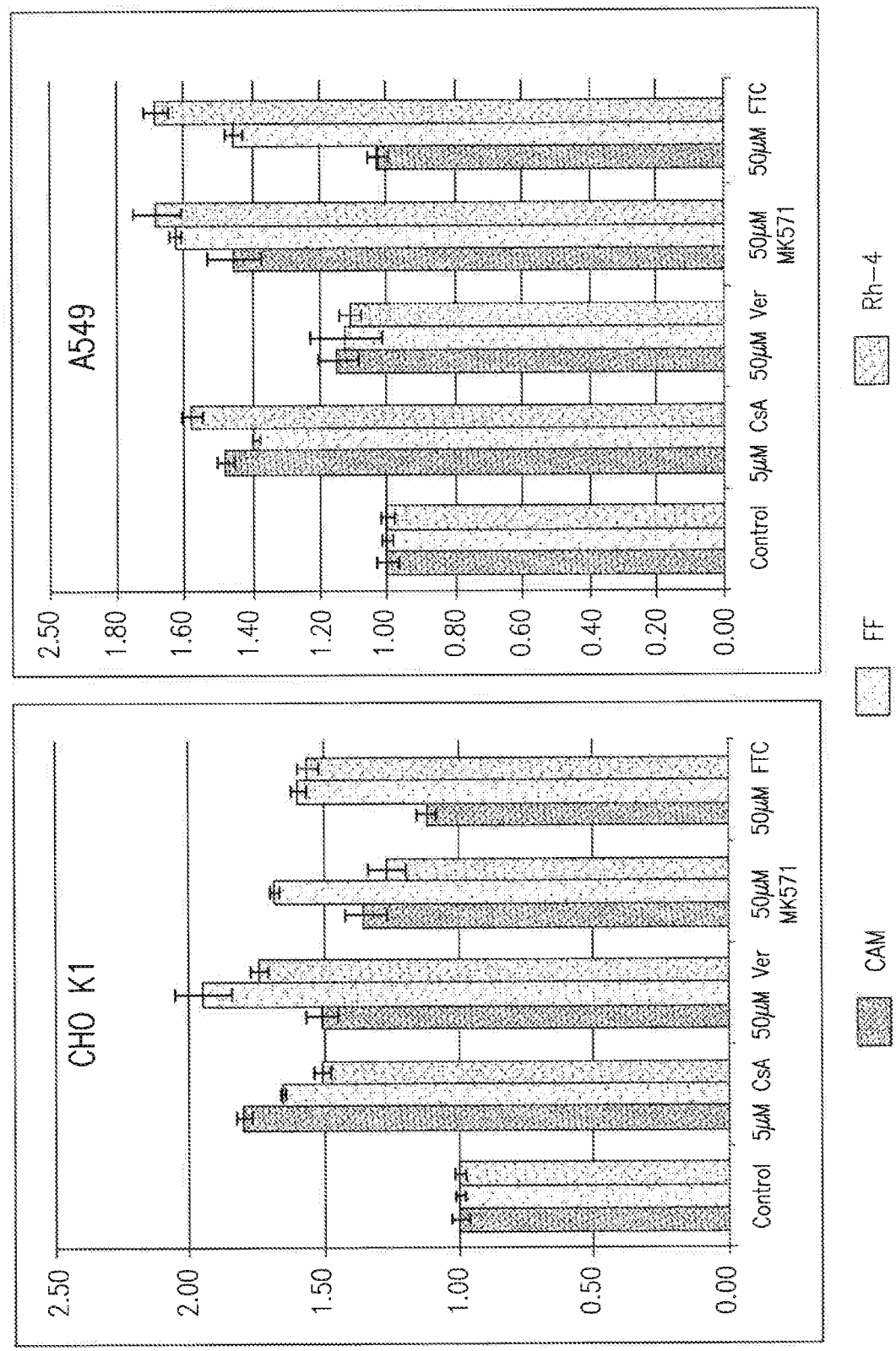
FIG. 10 are bar graphs showing results of MDR tests with four different inhibitors in which Fluo-8™ and Rhod-4™ were compared against Calcein AM.
Figure 10B:
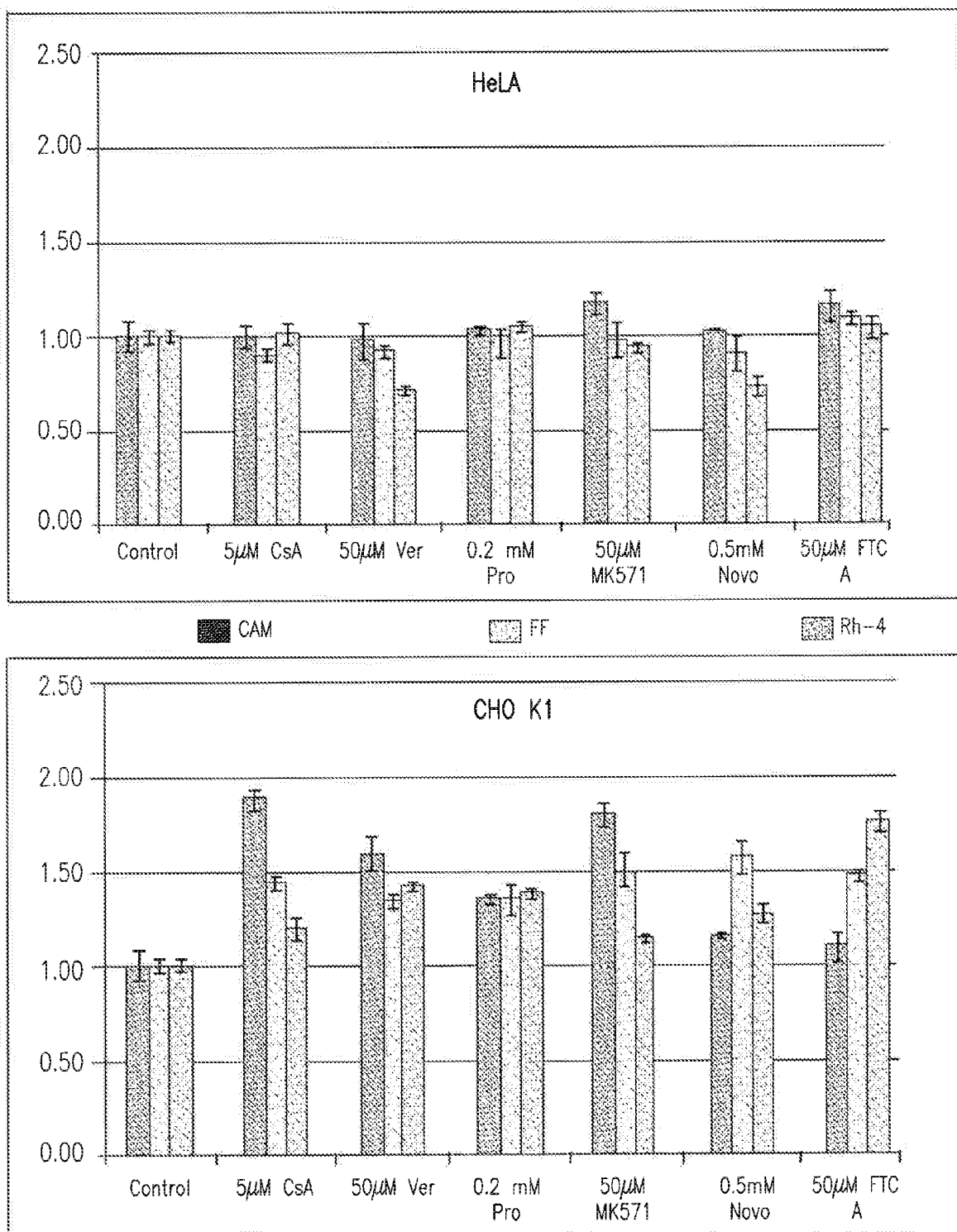

Results of measurements of MDR activity using a fluorescence microplate reader are presented in FIGS. 10A and 10B and are similar to the results obtained by flow cytometry methods. There are minor qualitative differences compared to the flow cytometry data. There may be a few reasons accounting for these differences: the method of quantification is different, and the assay has not been optimized.

Figure 10C:
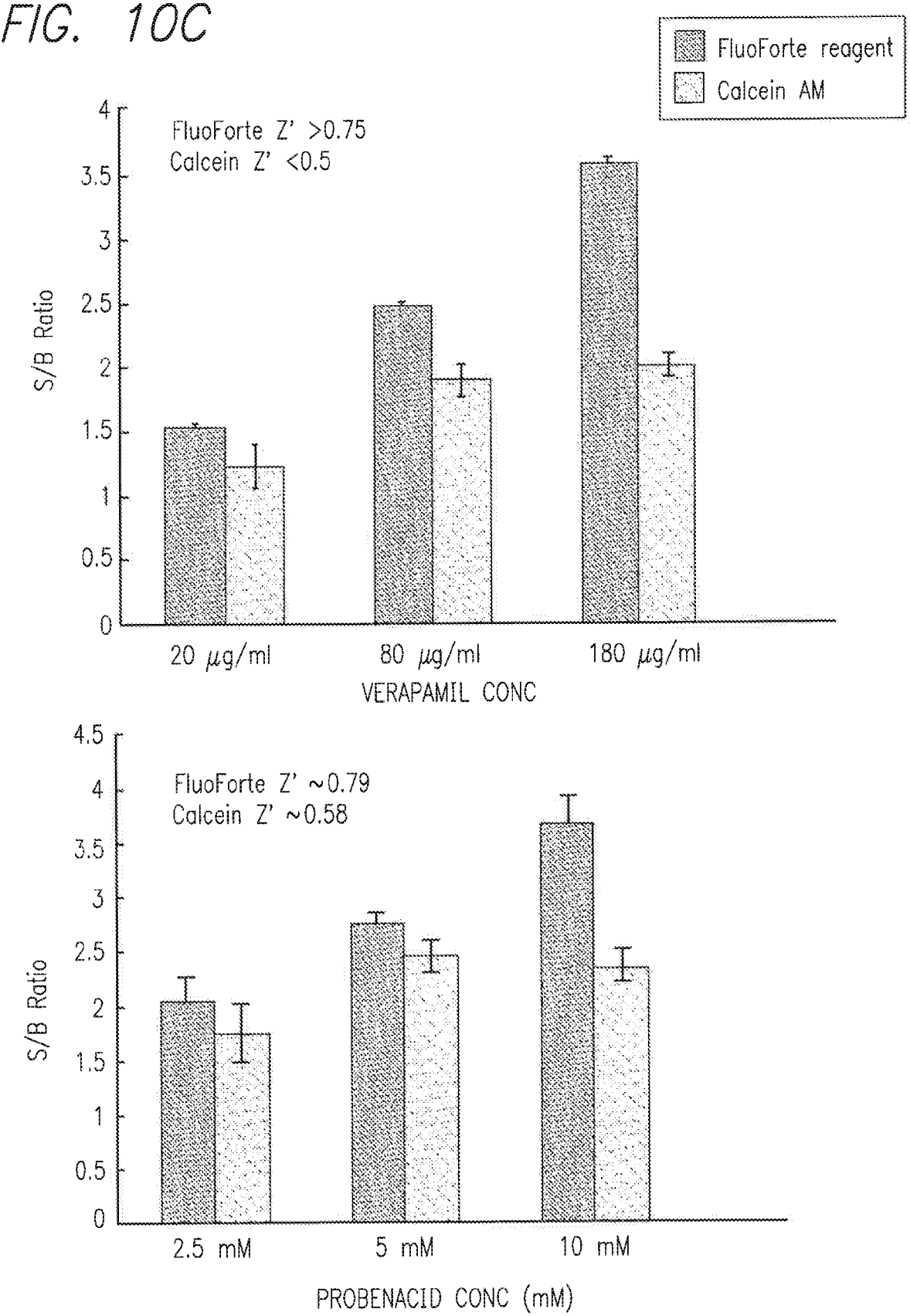

In addition, using of Fluo-8™ AM and Rhod-4™ AM to detect MDR activity in microplate format also results in a brighter and a more reproducible signal than when Calcein AM is used (FIG. 10C).

Example 13

Determination of Efflux-Mediated Multidrug Resistance in *E. coli* (or *Bacillus subtilis*) Using Both Flow Cytometry and Microplate Fluorimetry Method Flow Cytometry Flow cytometry experiments were performed using a FACS Calibur benchtop cytometer (BD Biosciences) equipped with a blue (488 nm) laser, and the signals were registered in FITC (530/30 filter), PE (585/42 filter) and PerCP (670 LP filter) channels. Fluo-8™ dye fluorescence was measured in the FL1 channel, and Rhod-4™ dye fluorescence—in the FL2 channel.

(i) Accumulation Assay

*E. coli* strains were cultured in 10 ml of LB medium at 37° C. and a shaker speed of 220 rpm until an $OD_{600}$ of 0.6 was achieved. Aliquots of 1.0 ml were centrifuged at 16,000×g for 3 minutes, the supernatant discarded and the pellet washed twice with PBS. The $OD_{600}$ of the bacterial suspension was adjusted to 0.3 using PBS without glucose. MDR probe was added at a final concentration of 0.5 μM (Fluo-1™ AM) or 2 μM (Rhod-4™ AM), and chlorpromazine (CPZ) was added to a final concentration of 20 μg/ml. Following incubation at 25° C. for 60 minutes, aliquots of 0.5 ml were taken for fluorescence measurements in the FACSCalibur™ flow cytometer. Data were collected for at least 10,000 events per sample.

Since the doses of the probes are not toxic, the net fluorescence of the bacteria is the result of the balance between the probe entry by passive diffusion (influx) and extrusion activity of efflux pump systems. Therefore, the strain that overexpresses efflux systems accumulates the least amount of the dye(s). On the contrary, accumulation of the dyes inside the bacterial cells is increased in the presence of compounds such as phenothiazines (e.g. CPZ), that have been shown to inhibit efflux activity of Gram-negative bacteria [Pages et al. Trends Mol. Med. 11(8):382-389 (2005)]. Thus, these compounds are usually employed for the demonstration of over-expressed efflux pumps of bacteria [Pages et al. Trends Mol. Med. 11(8):382-389 (2005)].

(ii) Efflux Assay

After loading the bacteria with MDR probe (final concentration was 5 µM for Fluo-8™ AM or 2 µM for Rhod-4™ AM) in the presence of chlorpromazine (CPZ, 20 µg/ml), the bacterial suspension was centrifuged at 16,000×g for 3 minutes. The supernatant was removed and the pellet resuspended in dye-free PBS, adjusting the $OD_{600}$ to 0.3. Efflux was assessed in the presence and absence of glucose at 0.4% (v/v). Aliquots of 0.5 ml were taken after 2.5, 5, 15, 30 and 60 minutes after incubation at 37° C., for fluorescence measurement in the FACSCalibur™ flow cytometer. Analyses were performed with an acquisition of at least 10,000 events per sample.

The on-line visualization of efflux activity by the probe-loaded bacterial cells requires that accumulation of the probes has previously taken place. Therefore, before performing the efflux assays, bacteria are exposed to conditions that promote significant accumulation of the probes(s): a temperature of 25° C., absence of glucose and presence of CPZ (20 µg/ml) for 60 minutes [Viveiros et al., Curr Drug Targets 9(9):760-778 (2008)]. When maximum accumulation has taken place under these conditions, the bacteria are washed free of both probe and inhibitor, and resuspended in fresh buffer with and without glucose. Flow cytometry assay confirms the maximal efflux of the probe occurs within 15 min from the bacterial strain over-expressing efflux pumps. Importantly, restoration of optimum conditions of glucose, noted to prevent accumulation, is required for the extrusion of the dyes. This assay shows that E. coli cells need an energy source for efflux to take place.

Microplate Assay to Estimate Dye Uptake by Mycobacteria.

M. smegmatis was grown to early exponential phase ($OD_{600}$, 0.6 to 1.0). The cells were pelleted by centrifugation at room temperature, resuspended in uptake buffer (50 mM $KH_2PO_4$ [pH 7.0], 5 mM $MgSO_4$), diluted to an $OD_{600}$ of 0.5, and pre-energized with 25 mM glucose for 5 min. One hundred microliters of cells was added per well of black walled, clear-bottomed 96-well microplates (Greiner Bio-One). Probe was added to a final concentration of 5 µM (Fluo-8™ AM) or 2 µM (Rhod-4™ AM), and its accumulation was measured over 60 min at room temperature in top-reading mode using a Synergy Mx reader (BioTek) and standard FITC (Fluo-8™) or Rhodamine (Rhod-4™) filter settings. When required, reserpine was added after 8 min of incubation with probe at a final concentration of 0.1 mM.

It is expected that relative fluorescence that accumulated in the bacterial strains with high expression of the efflux pump will be significantly less compared to the fluorescence accumulated in the non-resistant strain. Addition of the inhibitor (reserpine) will reconstitute fluorescence accumulation in the resistant strain.

Example 14

Bi-Directional Transport Assay in Functionally Polarized Epithelial Cell Monolayer In the transwell transport assay, polarized pig kidney epithelial cell line LLC-PK1, and its subclones expressing human multidrug resistance proteins (MDR, MRP or BCRP), and the polarized canine kidney cell line MDCK-II, and its multi-drug resistant subclones (described elsewhere) are used. These cell lines are selected for use because they enable direct comparison of their functional behaviors without the confounding effects of multiple transporters expressed in cell lines such as Caco-2.

LLC-PK1 control and transfected cells were grown in complete media consisting of RPMI 1640 medium (ATCC) supplemented with 10% (v/v) fetal calf serum and 1% (v/v) antibiotic-antimycotic and grown at 37° C. in the presence of 5% CO2. Cells were grown in Medium 199 (Invitrogen, Carlsbad, Calif.) supplemented with L-glutamine, 10% (v/v) fetal bovine serum (ATCC), 100 µg of penicillin and streptomycin per ml (Sigma/Aldrich) and grown at 37° C. in the presence of 5% $CO_2$.

Wild-type Madin-Darby canine kidney cells type II (MDCKII/wt) and stable MDCKII transfectants overexpressing hMRP1 (MDCKIIMRP1 cells), hMRP2 (MDCKII-MRP2 cells), hPgp (MDCKII-PGP cells) and hBCRP or mBcrpl (MDCKII-BCRP cells) (all are available from SOLVO Biotechnologies). The MDCKII cell lines were cultured in Dulbecco's modified Eagle's medium (with high glucose and glutamine concentrations, ATCC) supplemented with 10% FBS (ATCC), 1% nonessential amino acids, 100 µg of penicillin and streptomycin per ml (all from Sigma/Aldrich). Cells were incubated at 37° C. in 5% $CO_2$ at 95% humidity and were harvested via trypsinization at 80 to 90% confluence (about 4 days of growth). Studies were performed between the cell passages 6 to 20 from the initial stock.

For the transport assay, wild type and transfected cells were seeded on microporous polycarbonate membrane filters (0.33 $cm^2$ growth area and 0.4-µm pore size Transwell; Costar, Corning, N.Y.) at a density of $1 \times 10^5$ cells/well in 0.2 ml of complete medium. Following seeding, medium was changed daily, and transport studies were performed 4 or 5 days after seeding. Fresh media were added to the cells 1 h before the initiation of the experiment, and transepithelial electrical resistance values were measured with a Millicell-ERS (electrical resistance system) (Millipore, Billerica, Mass.). Bidirectional transport studies were performed at 37° C. in air. Before each experiment, the confluent cell monolayers on Transwell inserts were washed and equilibrated for 30 min with transport media [Hanks' balanced salt solution containing 10 mM HEPES and 10 mM glucose, pH 7.4]. The experiment was initiated by adding a solution containing the 5 µM of Fluo-8™ AM or 2 µM of Rhod-4™ AM in transport media to either the apical (for A-to-B transport) or basolateral (for B-to-A transport) compartment. When applicable, inhibitors were present in the transport medium of the donor side from the pre-incubation period throughout the permeability study. At 30, 60, 120, and 240 min, the sample aliquots (50 µl) of receiving solutions were withdrawn from the basolateral side (for A-to-B transport) or from the apical side (for B-to-A transport) and replaced immediately with an equal amount of fresh transport medium except at the 240-min time point (the end of the incubation). The cell integrity was monitored before and after the transport study to check for leaks in the epithelium by transepithelial electric resistance [Yee, Pharmaceutical Res. 14:763-766 (1997)].

Fluorescence intensity of Fluo-8™ or Rhod-4™ was measured using an OPTIMA FluoStar multiplate fluorimeter (BMG Labtech Inc., NC; equipped with 490 and 550 nm excitation filter and 520 and 570 nm emission filters) or Synergy™ Mx multi-mode microplate reader (BioTek Instruments Inc., VT; using 490 and 530 nm excitation and 520 and 555 nm emission settings). Apparent permeability ($P_{app}$) was calculated in the apical-to-basolateral direction ($P_{app\ A\rightarrow B}$) and in the basolateral-to-apical direction ($P_{app\ B\rightarrow A}$) as described previously [Polli et al., J Pharmacol Exp Ther. 299:620-628 (2001)]. Briefly, $P_{app}=(1/(A \times C_0)) \times (dQ/dt)$, where A is the surface area of permeable support, $C_0$ is the initial concentration in the donor compartment, and dQ/dt is the rate of transfer of compound into the acceptor compartment. This ratio of $P_{appB \to A}/P_{appA \to B}$ was estimated to evaluate all three transporter-mediated directional effluxes. The amount of Fluo-8™ or Rhod-4™ exported was calculated using a calibration curve made with the free dyes. All the data are expressed as mean±S.D. of three individual incubations. Student's two-sided t test was used to evaluate differences between two sets of data. P values<0.05 were considered statistically significant.

In wild type MDCKII and LLC-PK1 cells, Fluo-8™ and Rhod-4™ dye(s) export to the apical and basolateral side should be similar. Dye export should be detected in the transfectants of the epithelial polarized cells, and the nature of this export is dependent on the membrane localization of the particular transporter. When the transporter is localized to the lateral plasma membrane (MRP1), then several-fold increased dye(s) export to the basolateral side is expected. When the transporter is localized to the apical plasma membrane (MRP2 and MDR1), then several-fold increased dye(s) export to the apical side is expected. The increased export of the dye should be blocked in the presence of the corresponding specific inhibitor.

Many obvious variations will no doubt be suggested to those of ordinary skill in the art in light of the above detailed description and examples of the present invention. All such variations are fully embraced by the scope and spirit of the invention as more particularly defined in the claims that now follow.

What is claimed is:

1. A process for determining drug resistance of cells of interest, said process comprising the steps of:
   (A) providing:
      (i) a clinical or biological sample comprising cells;
      (ii) at least one xanthene compound that is transportable across a cell membrane by membrane transporters multidrug resistance 1 (MDR1), multidrug resistance associated protein 1 (MRP) and breast cancer resistant protein (BCRP); and
      (iii) one or more membrane transporter inhibitors;
   (B) contacting cells from a first portion of said clinical or biological sample with said at least one xanthene compound;
   (C) contacting cells from a second portion of said clinical or biological sample (i) with said at least one xanthene compound and said one or more inhibitors;
   (D) measuring fluorescent signals generated in step (B) and step (C); and
   (E) comparing the fluorescent signals measured in step (D) to determine elevated activities of said MDR1, MRP and BCRP, or a combination thereof, thereby determining the drug resistance of said cells of interest,
wherein said at least one xanthene compound has the structure

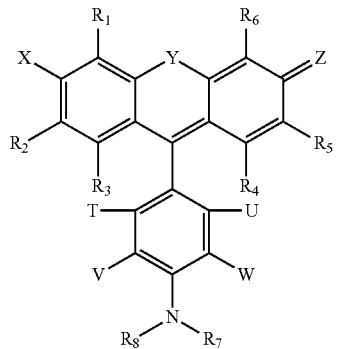

wherein
   $R^1$-$R^6$ are independently H, halogen, carboxy, alkoxy, aryloxy, thiol, alkylthiol, arylthiol, azido, nitro, nitroso, cyano, amino, hydroxy, phosphonyl, sulfonyl, carbonyl, boronic acid, aryl, or heteroaryl; or alkyl, or alkoxy, optionally substituted one or more times by halogen, amino, hydroxy, phosphonyl, sulfonyl, carbonyl, boronic acid, aryl or heteroaryl,
   heteroatom Y is independently selected from O, S, Se, $NR^9$ and $CR^{10}R^{11}$,
   X is independently selected from $OR^{12}$, $NR^{12}R^{13}$ and Z is independently selected from O and $NR^{16}R^{17}$, where each $R^9$, $R^{10}$, $R^{11}$, $R^{12}$, $R^{13}$, $R^{16}$ and $R^{17}$ is independently H, an alkyl having 1-12 carbons, carboxyalkyl, substituted or non-substituted amino alkyl or alkylsulfonate,
   T and U are independently hydrogen, alkyl having 1-12 carbons, alkoxy having 1-12 carbons, aryloxy, amino, halogen, cyano, carboxy, carboxyalkyl, acetoxymethylcarbonyl, carbonyl, sulfonyl, phosphonyl, boronic acid, aryl, and heteroaryl, and
   V and W are independently selected from $OR^{14}$, $SR^{15}$ or $NR^{12}R^{13}$, such that at least one of V or W, in combination with $NR^7R^8$, forms a metal chelator, where each $R^7$, $R^8$, and $R^{12}$-$R^{15}$ are independently H, an alkyl having 1-12 carbons, carboxyalkyl, alkoxy or aryloxy.

2. The process of claim 1, wherein said step (D) measures cellular uptake of said at least one xanthene compound.

3. The process of claim 1, wherein in said step (A), the one or more inhibitors are provided in an amount sufficient to substantially prevent transport of the at least one xanthene compound across a cell membrane by one or more of the membrane transporters MDR1, MRP and BCRP.

4. The process of claim 1, wherein said at least one xanthene compound has the structure

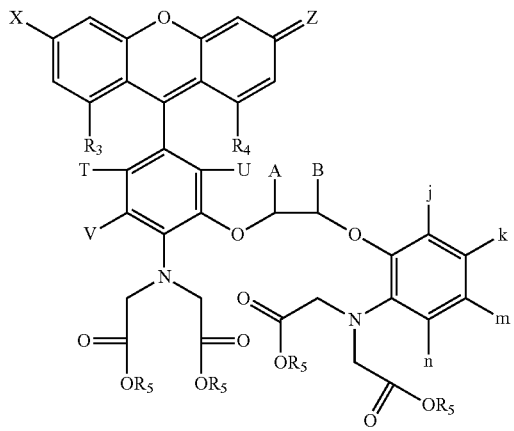

wherein
   A and B are independently hydrogen, alkyl, cycloalkyl, or aryl; or A and B taken in combination are cycloalkyl or aryl;
   j, k, m and n are independently hydrogen, halogen, carboxy, alkoxy, aryloxy, thiol, alkylthiol, arylthiol, azido, nitro, nitroso, cyano, amino, hydroxy, phosphonyl, sulfonyl, carbonyl, boronic acid, aryl, or heteroaryl; or alkyl, or alkoxy that is itself optionally substituted one or more times by halogen, amino, hydroxy, phosphonyl, sulfonyl, carbonyl, boronic acid, aryl or heteroaryl; and
   each $R^5$ is independently hydrogen, alkyl having 1-9 carbons, acetoxymethyl, or a biologically compatible salt.

5. The process of claim 4, wherein said xanthene compound has the structure

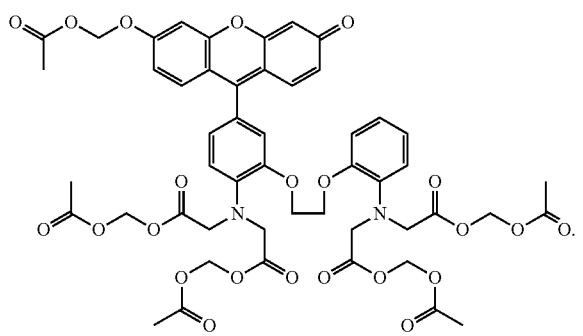 [SMILES: CC(=O)OCOC(=O)CN(CC(=O)OCOC(C)=O)c1ccccc1OCCOc1cc(-c2c3ccc(=O)cc-3oc3cc(OCOC(C)=O)ccc23)ccc1N(CC(=O)OCOC(C)=O)CC(=O)OCOC(C)=O]

6. The process of claim 1, wherein said one or more membrane transporter inhibitors comprise a general inhibitor.

7. The process of claim 6, wherein said general inhibitor is cyclosporin A, biricodar (VX-710), tariquidar (XR9576), a plant polyphenol, curcumin, tRA98006 or imatinib mesylate.

8. The process of claim 6, wherein the general inhibitor is cyclosporin A.

9. The process of claim 1, wherein in said step (A), there is further provided at least one viability dye.

10. The process of claim 9, wherein said at least one viability dye is propidium iodide, 7-amino-actinomycin D (7-AAD), DRAQ-7, Nuclear ID Red, Nuclear ID Green, SYTOX Green, SYTOX Orange, SYTOX Blue, YOYO, TOTO or TO-PRO, or a compound having the structure:

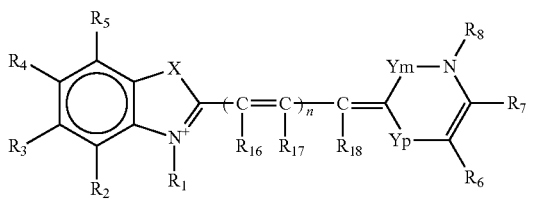

wherein
X comprises $CR^{11}R^{12}$, $NR^{11}$, O, S or Se where $R^{11}$ and $R^{12}$ independently comprise hydrogen, a halogen, an amino group, an alkyl group wherein said alkyl group is saturated or unsaturated, linear or branched, substituted or unsubstituted, an alkoxy group wherein said alkyl group is saturated or unsaturated, branched or linear, substituted or unsubstituted, or when taken together, $R^{11}$ and $R^{12}$ form a 5 or 6 membered ring;
n can be 0, 1, 2 or 3;
Y is $-CR^9=CR^{10}-$;
m and p can have values of 0 or 1 and m+p=1;
at least one of $R^1$, $R^2$, $R^3$, $R^4$, $R^5$, $R^{11}$ or $R^{12}$ comprises Q(1) or at least one of $R^6$, $R^7$, $R^8$, $R^9$ or $R^{10}$ comprises Q(2);
Q(1) comprises a sulfonate ($SO_3^-$), a sulfonate ester ($SO_2ER^{13}$), a sulfoxide ($SOR^{13}$), a sulfone ($SO_2CR^{13}R^{14}R^{15}$), a sulfonamide ($SO_2NR^{13}R^{14}$), a phosphate ($PO_4^=$), a phosphate monoester ($PSO^-ER^{13}$), a phosphate diester ($PO_2ER^{13}ER^{14}$), a alkyl phosphonate ($PO_3^=$) a alkyl phosphonate monoester ($PO_2^-ER^{13}$) a alkyl phosphonate diester ($POER^{13}ER^{14}$), a thiophosphate ($PSO_3^=$), a thiophosphate monoester ($PSO_2^-ER^{13}$) a thiophosphate diester ($PSOER^{13}ER^{14}$), a thiophosphonate ($PSO_2^=$), a thiophosphonate monoester ($PSO^-ER^{13}$) a thiophosphonate diester ($PSER^{13}ER^{14}$), a phosphonamide ($PONR^{13}R^{14}NR^{19}R^{20}$), its thioanalogue ($PSNR^{13}R^{14}NR^{19}R^{20}$), a phosphoramide ($PONR^{13}R^{14}NR^{15}NR^{19}R^{20}$), its thioanalogue ($PSNR^{13}R^{14}NR^{15}NR^{19}R^{20}$), a phosphoramidite ($PO_2R^{19}NR^{13}R^{14}$) or its thioanalogue ($POSR^{19}NR^{13}R^{14}$) wherein any of E can independently comprise O or S and the structures are as described previously;

Q is attached directly, or indirectly through a linker arm comprising carbon, sulfur, oxygen, nitrogen, and any combinations thereof and wherein said linker arm may be saturated or unsaturated, linear or branched, substituted or unsubstituted and any combinations thereof and wherein when Q is a sulfonamide, it does not comprise a terminal reactive group or a linker joining the dye to a target molecule;

Q(2) comprises an alkyl, aminoalkyl, substituted aminoalkyl, a benzyl, a substituted benzyl, a sulfoxide ($SOR^{13}$), a sulfone ($SO_2CR^{13}R^{14}R^{15}$), a sulfonamide ($SO_2NR^{13}R^{14}$), a phosphate ($PO_4^=$), a phosphate monoester ($PO_3^-ER^{13}$), a phosphate diester ($PO_2ER^{13}ER^{14}$), a phosphonate ($PO_3^=$) a phosphonate monoester ($PO_2^-ER^{13}$) a phosphonate diester ($POER^{13}ER^{14}$), a thiophosphate ($PSO_3^=$), a thiophosphate monoester ($PSO_2^-ER^{13}$) a thiophosphate diester ($PSOER^{13}ER^{14}$), a thiophosphonate ($PSO_2^=$), a thiophosphonate monoester ($PSO^-ER^{13}$) a thiophosphonate diester ($PSER^{13}ER^{14}$), a phosphonamide ($PONR^{13}R^{14}NR^{19}R^{20}$), its thioanalogue ($PSNR^{13}R^{14}NR^{19}R^{20}$), a phosphoramide ($PONR^{13}R^{14}NR^{15}NR^{19}R^{20}$), its thioanalogue ($PSNR^{13}R^{14}NR^{15}NR^{19}R^{20}$), a phosphoramidite ($PO_2R^{19}NR^{13}R^{14}$) or its thioanalogue ($POSR^{19}NR^{13}R^{14}$) wherein any of E can independently comprise O or S and the structures are as described previously;

Q(2) is attached directly, or indirectly through a linker arm comprising carbon, sulfur, oxygen, nitrogen, and any combinations thereof and wherein said linker arm may be saturated or unsaturated, linear or branched, substituted or unsubstituted and any combinations thereof and wherein when Q' is a sulfonamide, it does not comprise a terminal reactive group or a linker joining the dye to a target molecule;

$R^{13}$, $R^{14}$, $R^{15}$, $R^{19}$ and $R^{20}$ can be hydrogen, a halogen, an amino group, an alkyl group wherein said alkyl group is saturated or unsaturated, linear or branched, substituted or unsubstituted, an alkoxy group wherein said alkoxy group is saturated or unsaturated, branched or linear, substituted or unsubstituted, or when taken together $R^{13}$ and $R^{14}$ form a five or six membered ring;

$R^{13}$ and $R^{14}$ may further comprise a heteroatom containing side chain wherein said side chain is joined to the R group by a linkage which comprises an ether linkage ($-OR^{25}$), a thioether linkage ($-SR^{25}$), or an amine linkage ($-NR^{25}R^{26}$ or $-N^+R^{25}R^{26}R^{27}$), and wherein $R^{25}$, $R^{26}$ and $R^{27}$ independently comprise hydrogen, Z, an alkyl group wherein said alkyl group is saturated or unsaturated, linear or branched, substituted or unsubstituted, an alkoxy group that is saturated or unsaturated, branched or linear, substituted or unsubstituted, or when taken together, $R^{25}$ and $R^{26}$, and $R^{26}$ and $R^{27}$ independently comprise a five or six membered ring, and wherein any of $R^{25}$, $R^{26}$ or $R^{27}$ may further comprise said heteroatom containing side chain;

$R^{16}$, $R^{17}$, $R^{18}$ and the remaining $R^1$, $R^2$, $R^3$, $R^4$, $R^5$, $R^6$, $R^7$, $R^8$, $R^9$, $R^{10}$, $R^{11}$ and $R^{12}$ can independently be hydrogen, Z, an alkyl group wherein said alkyl group is saturated or unsaturated, linear or branched, substituted or unsubstituted, an alkoxy group wherein said alkoxy group is saturated or unsaturated, branched or linear; substituted or unsubstituted, or when taken together, $R^2$ and $R^3$, $R^3$ and $R^4$, $R^4$ and $R^5$, $R^6$ and $R^7$, and $R^7$ and $R^8$ may form a 5 or 6 membered ring; or when taken together $R^1$ and $R^{16}$, $R^{11}$ and $R^{16}$, $R^{16}$ and $R^{17}$, $R^{17}$ and $R^{18}$, and $R^{18}$ and $R^9$ may form a 5 or 6 membered ring;

Z comprises a carboxyl group ($CO_2$—), a carbonate ester ($COER^{13}$), a sulfonate ($SO_3^-$), a sulfonate ester ($SO_2ER^{13}$), a sulfoxide ($SOR^{13}$), a sulfone ($SO_2CR^{13}R^{14}R^{15}$), a sulfonamide ($SO_2NR^{13}R^{14}$), a phosphate ($PO_4^=$), a phosphate monoester ($PO_3^-ER^{13}$), a phosphate diester ($PO_2ER^{13}ER^{14}$), a phosphonate ($PO_3^=$) a phosphonate monoester ($PO_2^-ER^{13}$) a phosphonate diester ($POER^{13}ER^{14}$), a thiophosphate ($PSO_3^=$), a thiophosphate monoester ($PSO_2^-ER^{13}$) a thiophosphate diester ($PSOER^{13}ER^{14}$), a thiophosphonate ($PSO_2^=$), a thiophosphonate monoester ($PSO^-ER^{13}$) a thiophosphonate diester ($PSER^{13}ER^{14}$), a phosphonamide ($PONR^{13}R^{14}NR^{19}R^{20}$), its thioanalogue ($PSNR^{13}R^{14}NR^{19}R^{20}$), a phosphoramide ($PONR^{13}R^{14}NR^{15}NR^{19}R^{20}$), its thioanalogue ($PSNR^{13}R^{14}NR^{15}NR^{19}R^{20}$), a phosphoramidite ($PO_2R^{19}NR^{13}R^{14}$) or its thioanalogue ($POSR^{19}NR^{13}R^{14}$) where E can Z is attached directly, or indirectly through a linker arm comprising carbon, sulfur, oxygen, nitrogen, and any combinations thereof and wherein said linker arm may be saturated or unsaturated, linear or branched, substituted or unsubstituted and any combinations thereof;

any of $R^1$, $R^2$, $R^3$, $R^4$, $R^5$, $R^6$, $R^7$, $R^8$, $R^9$ or $R^{10}$, $R^{11}$ or $R^{12}$ may further comprise a heteroatom containing side chain wherein said side chain is joined to the R group by a linkage which comprises an ether linkage (—$OR^{25}$), a thioether linkage (—$SR^{25}$), Or an amine linkage (—$NR^{25}R^{26}$ or —$N^+R^{25}R^{26}R^{27}$);

$R^{25}$, $R^{26}$ and $R^{27}$ independently comprise hydrogen, Z, an alkyl group wherein said alkyl group is saturated or unsaturated, linear or branched, substituted or unsubstituted, an alkoxy group that is saturated or unsaturated, branched or linear, substituted or unsubstituted, or when taken together, $R^{25}$ and $R^{26}$, and $R^{26}$ and $R^{27}$ independently comprise a five or six membered ring, and wherein any of $R^{25}$, $R^{26}$ or $R^{27}$ may further comprise said heteroatom containing side chain; and $R^8$ may comprise a substituted group capable of forming symmetric or asymmetric polymeric dye.

11. The process of claim 9, wherein the cells are contacted with said at least one viability dye before said contacting steps (B) and (C).

12. The process of claim 11, wherein said at least one non-xanthene dye is a nuclear identification stain, calcein AM, Pheophorbide A, Chloromethylfluorescein diacetate (CMFDA), Hoechst 33342, BODIPY-Prazozin, Fura-2 AM, monobromobimane, BODIPY-Taxol or 3,3'-diethyloxacarbocyanine iodide ($DIOC_2(3)$].

13. The process of claim 9, wherein said at least one viability dye is propidium iodide.

14. The process of claim 9, wherein the cells are contacted with said at least one viability dye during said contacting steps (B) and (C).

15. The process of claim 9, wherein the cells are contacted with said at least one viability dye after said contacting steps (B) and (C).

16. The process of claim 1, wherein in step (A), there is further provided at least one non-xanthene dye in step (B) and step (C).

17. The process of claim 1, wherein in said step (D), measuring is carried out by a means comprising a flow cytometer, a microplate reader, a microscope, a fluorimeter, a high-content screening platform, a high-content cell analysis system or a laser-scanning cytometer.

18. The process of claim 1, wherein in said step (A), there is provided a quenching reagent for minimizing extracellular fluorescent signal from said at least one xanthene compound.

19. The process of claim 18, wherein said quenching reagent comprises Evans Blue, o-tolidine, Trypan Blue, Trypan Red or Brilliant Black.

20. The process of claim 1, wherein in step (A), there is provided one or more surfactants for increasing cellular uptake of said at least one xanthene compound, and wherein said one or more surfactants are used in said contacting steps (B) and (C).

21. The process of claim 20, wherein said one or more surfactants comprise Pluronic 127, L61, L81, P85 or F108.

22. The process of claim 1, wherein said one or more membrane transporter inhibitors comprise a specific inhibitor.

23. The process of claim 22, wherein said specific inhibitor is valspodar (PSC833), verapamil, vanadate, PAK-104P, MK-571, FTC, Ko134, Elacridar (GF 120918), novobiocin, probenecid, BIB-E, disulfuram, indomethacin, furocemide, Penicillin G, sulfinpirazole, laniquidar (R101933), zosuquidar (LY335979), ontogeny (ONT-093), isothiocyanates, phytoestrogens, TAG-139, flavenoids, MS-209, NSAIDs, mitotane (NSC-38271), PK11195, cyclosporine D, anthranilamide, pipecolinate, quinoline, OC-144-093, diallyl sulfide, amooranin, agosterol A, siRNA, rifampicin, amiodarone, quinidine, quinine, nifedipine, dexniguldipin, LY455776, V-104, tricyclic izoxazoles, pluronic L61, or fumitremorgin C.

24. The process of claim 22, wherein said one or more membrane transporter inhibitors comprise more than one specific inhibitors.

25. The process of claim 22, wherein said specific inhibitor is verapamil, probenecid or novobiocin.

26. The process of claim 1, wherein said one or more membrane transporter inhibitors comprise both a general inhibitor and a specific inhibitor.

27. A process for determining drug resistance of cells of interest, said process comprising the steps of:
(A) providing:
(i) at least three portions of a clinical or biological sample comprising cells;
(ii) at least one xanthene compound that is transportable across a cell membrane by membrane transporters MDR1, MRP and BCRP; and
(iii) one or more membrane transporter inhibitors;
(B) contacting cells from a first portion of said clinical or biological sample with said at least one xanthene compound under conditions sufficient to inhibit efflux of said at least one xanthene compound from said cells;

(C) contacting cells from a second portion of said clinical or biological sample with said at least one xanthene compound under conditions sufficient to permit efflux of said at least one xanthene compound from said cells;

(D) contacting cells from a third portion of said clinical or biological sample with said at least one xanthene compound and said one or more inhibitors;

(E) measuring fluorescent signals generated in steps (B), (C) and (D); and (F) comparing the fluorescent signals measured in step (E) to determine elevated activities of said MDR1, MRP, BCRP, or a combination thereof, thereby determining the drug resistance of said cells of interest, wherein said at least one xanthene compound has the structure

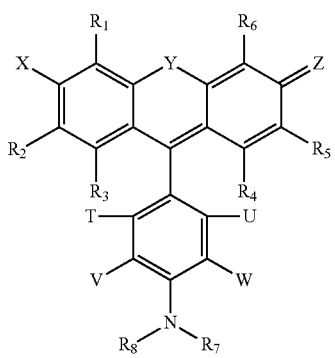

wherein
$R^1$-$R^6$ are independently H, halogen, carboxy, alkoxy, aryloxy, thiol, alkylthiol, arylthiol, azido, nitro, nitroso, cyano, amino, hydroxy, phosphonyl, sulfonyl, carbonyl, boronic acid, aryl, or heteroaryl; or alkyl, or alkoxy, optionally substituted one or more times by halogen, amino, hydroxy, phosphonyl, sulfonyl, carbonyl, boronic acid, aryl or heteroaryl, heteroatom Y is independently selected from O, S, Se, $NR^9$ and $CR.^{10}R^{11}$, X is independently selected from $OR^{12}$, $NR^{12}R^{13}$ and Z is independently selected from O and $NR^{16}R^{17}$, where each $R^9$, $R^{10}$, $R^{11}R^{12}$, $R^{13}$, $R^{16}$ and $R^{17}$ is independently H, an alkyl having 1-12 carbons, carboxyalkyl, substituted or non-substituted amino alkyl or alkylsulfonate, T and U are independently hydrogen, alkyl having 1-12 carbons, alkoxy having 1-12 carbons, aryloxy, amino, halogen, cyano, carboxy, carboxyalkyl, acetoxymethylcarbonyl, carbonyl, sulfonyl, phosphonyl, boronic acid, aryl, and heteroaryl, and V and W are independently selected from $OR^{14}$, $SR^{15}$ or $NR^{12}R^{13}$, such that at least one of V or W, in combination with $NR^7R^8$, forms a metal chelator, where each $R^7$, $R^8$, and $R^{12}$-$R^{15}$ are independently H, an alkyl having 1-12 carbons, carboxyalkyl, alkoxy or aryloxy.

28. The process of claim 27, wherein in said step (A), the one or more inhibitors are provided in an amount sufficient to substantially prevent transport of the at least one xanthene compound (II) across a cell membrane by one or more of the membrane transporters MDR1, MRP and BCRP.

29. The process of claim 27, wherein step (B), contacting is carried out under conditions wherein temperature is lowered to inhibit efflux.

30. The process of claim 29, wherein said lowered temperature is in a range from about 4° C. to about 10° C.

31. The process of claim 27, wherein in step (C), contacting is carried out under said conditions wherein temperature is raised to permit efflux.

32. The process of claim 31, wherein said raised temperature is from about 15° C. to about 37° C.

33. The process of claim 27, wherein said one or more membrane transporter inhibitors comprise a general inhibitor.

34. The process of claim 33, wherein said general inhibitor is cyclosporin A, biricodar (VX-710), tariquidar (XR9576), a plant polyphenol, curcumin, tRA98006 or imatinib mesylate.

35. The process of claim 27, wherein said at least one xanthene compound has the structure

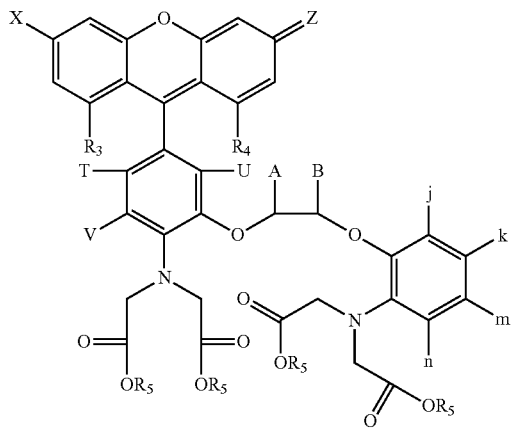

wherein
A and B are independently hydrogen, alkyl, cycloalkyl, or aryl; or A and B taken in combination are cycloalkyl or aryl;

j, k, m and n are independently hydrogen, halogen, carboxy, alkoxy, aryloxy, thiol, alkylthiol, arylthiol, azido, nitro, nitroso, cyano, amino, hydroxy, phosphonyl, sulfonyl, carbonyl, boronic acid, aryl, or heteroaryl; or alkyl, or alkoxy that is itself optionally substituted one or more times by halogen, amino, hydroxy, phosphonyl, sulfonyl, carbonyl, boronic acid, aryl or heteroaryl; and each $R^5$ is independently hydrogen, alkyl having 1-9 carbons, acetoxymethyl, or a biologically compatible salt.

36. The process of claim 35, wherein said at least one xanthene compound has the structure

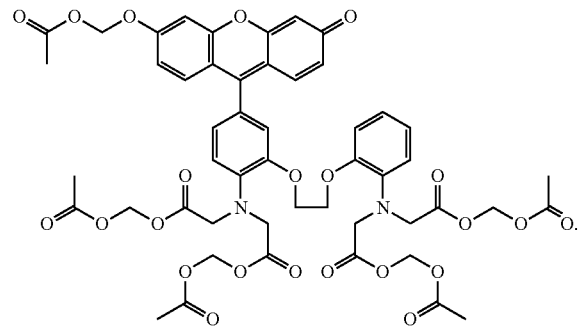 [SMILES: CC(=O)OCOC(=O)CN(CC(=O)OCOC(C)=O)c1ccccc1OCCOc1cc(-c2c3ccc(=O)cc-3oc3cc(OCOC(C)=O)ccc23)ccc1N(CC(=O)OCOC(C)=O)CC(=O)OCOC(C)=O]

37. The process of claim 27, wherein said step (A), there is further provided at least one viability dye.

38. The process of claim 37, wherein said at least one viability dye is propidium iodide, 7-amino-actinomycin D (7-AAD), DRAQ-7, Nuclear ID Red, Nuclear ID Green, SYTOX Green, SYTOX Orange, SYTOX Blue, YOYO, TOTO or TO-PRO, or a compound having the structure:

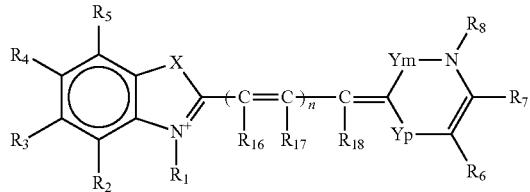

wherein
- X comprises $CR^{11}R^{12}$, $NR^{11}$, O, S or Se where $R^{11}$ and $R^{12}$ independently comprise hydrogen, a halogen, an amino group, an alkyl group wherein said alkyl group is saturated or unsaturated, linear or branched, substituted or unsubstituted, an alkoxy group wherein said alkyl group is saturated or unsaturated, branched or linear, substituted or unsubstituted, or when taken together, $R^{11}$ and $R^{12}$ form a 5 or 6 membered ring;
- n can be 0, 1, 2 or 3;
- Y is —$CR^9$=$CR^{10}$—
- m and p can have values of 0 or 1 and m+p=1;
- at least one of $R^1$, $R^2$, $R^3$, $R^4$, $R^5$, $R^{11}$ or $R^{12}$ comprises Q(1) or at least one of $R^6$, $R^7$, $R^8$, $R^9$ or $R^{10}$ comprises Q(2);
- Q(1) comprises a sulfonate ($SO_3^-$), a sulfonate ester ($SO_2ER^{13}$), a sulfoxide ($SOR^{13}$), a sulfone ($SO_2CR^{13}R^{14}R^{15}$), a sulfonamide ($SO_2NR^{13}R^{14}$), a phosphate ($PO_4^=$), a phosphate monoester ($PO_3^-ER^{13}$), a phosphate diester ($PO_2ER^{13}ER^{14}$), a alkyl phosphonate ($PO_3^=$) a alkyl phosphonate monoester ($PO_2^-ER^{13}$) a alkyl phosphonate diester ($POER^{13}ER^{14}$), a thiophosphate ($PSO_3^=$), a thiophosphate monoester ($PSO_2^-ER^{13}$) a thiophosphate diester ($PSOER^{13}ER^{14}$), a thiophosphonate ($PSO_2^=$), a thiophosphonate monoester ($PSO^-ER^{13}$) a thiophosphonate diester ($PSER^{13}ER^{14}$), a phosphonamide ($PONR^{13}R^{14}NR^{19}R^{20}$), its thioanalogue ($PSNR^{13}R^{14}NR^{19}R^{20}$), a phosphoramide ($PONR^{13}R^{14}NR^{15}NR^{19}R^{20}$), its thioanalogue ($PSNR^{13}R^{14}NR^{15}NR^{19}R^{20}$), a phosphoramidite ($PO_2R^{19}NR^{13}R^{14}$) or its thioanalogue ($POSR^{19}NR^{13}R^{14}$) wherein any of E can independently comprise O or S and the structures are as described previously;
- Q is attached directly, or indirectly through a linker arm comprising carbon, sulfur, oxygen, nitrogen, and any combinations thereof and wherein said linker arm may be saturated or unsaturated, linear or branched, substituted or unsubstituted and any combinations thereof and wherein when Q is a sulfonamide, it does not comprise a terminal reactive group or a linker joining the dye to a target molecule;
- Q(2) comprises an alkyl, aminoalkyl, substituted aminoalkyl, a benzyl, a substituted benzyl, a sulfoxide ($SOR^{13}$), a sulfone ($SO_2CR^{13}R^{14}R^{15}$), a sulfonamide ($SO_2NR^{13}R^{14}$), a phosphate ($PO_4^=$), a phosphate monoester ($PO_3^-ER^{13}$), a phosphate diester ($PO_2ER^{13}ER^{14}$), a phosphonate ($PO_3^=$) a phosphonate monoester ($PO_2^-ER^{13}$) a phosphonate diester ($POER^{13}ER^{14}$), a thiophosphate ($PSO_3^=$), a thiophosphate monoester ($PSO_2^-ER^{13}$) a thiophosphate diester ($PSOER^{13}ER^{14}$), a thiophosphonate ($PSO_2^=$), a thiophosphonate monoester ($PSO^-ER^{13}$) a thiophosphonate diester ($PSER^{13}ER^{14}$), a phosphonamide ($PONR^{13}R^{14}NR^{19}R^{20}$), its thioanalogue ($PSNR^{13}R^{14}NR^{19}R^{20}$), a phosphoramide ($PONR^{13}R^{14}NR^{15}NR^{19}R^{20}$), its thioanalogue ($PSNR^{13}R^{14}NR^{15}NR^{19}R^{20}$), a phosphoramidite ($PO_2R^{19}NR^{13}R^{14}$) or its thioanalogue ($POSR^{19}NR^{13}R^{14}$) wherein any of E can independently comprise O or S and the structures are as described previously;
- Q(2) is attached directly, or indirectly through a linker arm comprising carbon, sulfur, oxygen, nitrogen, and any combinations thereof and wherein said linker arm may be saturated or unsaturated, linear or branched, substituted or unsubstituted and any combinations thereof and wherein when Q' is a sulfonamide, it does not comprise a terminal reactive group or a linker joining the dye to a target molecule;
- $R^{13}$, $R^{14}$, $R^{15}$, $R^{19}$ and $R^{20}$ can be hydrogen, a halogen, an amino group, an alkyl group wherein said alkyl group is saturated or unsaturated, linear or branched, substituted or unsubstituted, an alkoxy group wherein said alkoxy group is saturated or unsaturated, branched or linear, substituted or unsubstituted, or when taken together $R^{13}$ and $R^{14}$ form a five or six membered ring;
- $R^{13}$ and $R^{14}$ may further comprise a heteroatom containing side chain wherein said side chain is joined to the R group by a linkage which comprises an ether linkage (—$OR^{25}$), a thioether linkage (—$SR^{25}$), or an amine linkage (—$NR^{25}R^{26}$ or —$N^+R^{25}R^{26}R^{27}$), and wherein $R^{25}$, $R^{26}$ and $R^{27}$ independently comprise hydrogen, Z, an alkyl group wherein said alkyl group is saturated or unsaturated, linear or branched, substituted or unsubstituted, an alkoxy group that is saturated or unsaturated, branched or linear, substituted or unsubstituted, or when taken together, $R^{25}$ and $R^{26}$, and $R^{26}$ and $R^{27}$ independently comprise a five or six membered ring, and wherein any of $R^{25}$, $R^{26}$ or $R^{27}$ may further comprise said heteroatom containing side chain;
- $R^{16}$, $R^{17}$, $R^{18}$ and the remaining $R^1$, $R^2$, $R^3$, $R^4$, $R^5$, $R^6$, $R^7$, $R^8$, $R^9$, $R^{10}$, $R^{11}$ and $R^{12}$ can independently be hydrogen, Z, an alkyl group wherein said alkyl group is saturated or unsaturated, linear or branched, substituted or unsubstituted, an alkoxy group wherein said alkoxy group is saturated or unsaturated, branched or linear; substituted or unsubstituted, or when taken together, $R^2$ and $R^3$, $R^3$ and $R^4$, $R^4$ and $R^5$, $R^6$ and $R^7$, and $R^7$ and $R^8$ may form a 5 or 6 membered ring; or when taken together $R^1$ and $R^{16}$, $R^{11}$ and $R^{16}$, $R^{16}$ and $R^{17}$, $R^{17}$ and $R^{18}$, and $R^{18}$ and $R^9$ may form a 5 or 6 membered ring;
- Z comprises a carboxyl group ($CO_2^-$), a carbonate ester ($COER^{13}$), a sulfonate ($SO_3^-$), a sulfonate ester ($SO_2ER^{13}$), a sulfoxide ($SOR^{13}$), a sulfone ($SO_2CR^{13}R^{14}R^{15}$), a sulfonamide ($SO_2NR^{13}R^{14}$), a phosphate ($PO_4^=$), a phosphate monoester ($PO_3^-ER^{13}$), a phosphate diester ($PO_2ER^{13}ER^{14}$), a phosphonate ($PO_3^=$) a phosphonate monoester ($PO_2^-ER^{13}$) a phosphonate diester ($POER^{13}ER^{14}$), a thiophosphate ($PSO_3^=$), a thiophosphate monoester ($PSO_2^-ER^{13}$) a thiophosphate diester ($PSOER^{13}ER^{14}$), a thiophosphonate ($PSO_2^=$), a thiophosphonate monoester (PSO⁻ER¹³) a thiophosphonate diester (PSER¹³ER¹⁴), a phosphonamide (PONR¹³R¹⁴NR¹⁹R²⁰), its thioanalogue (PSNR¹³R¹⁴NR¹⁹R²⁰), a phosphoramide (PONR¹³R¹⁴NR¹⁵NR¹⁹R²⁰), its thioanalogue (PSNR¹³R¹⁴NR¹⁵NR¹⁹R²⁰), a phosphoramidite (PO₂R¹⁹NR¹³R¹⁴) or its thioanalogue (POSR¹⁹NR¹³R¹⁴) where E can be independently O or S and the structures are as described previously;

Z is attached directly, or indirectly through a linker arm comprising carbon, sulfur, oxygen, nitrogen, and any combinations thereof and wherein said linker arm may be saturated or unsaturated, linear or branched, substituted or unsubstituted and any combinations thereof;

any of $R^1$, $R^2$, $R^3$, $R^4$, $R^5$, $R^6$, $R^7$, $R^8$, $R^9$ or $R^{10}$, $R^{11}$ or $R^{12}$ may further comprise a heteroatom containing side chain wherein said side chain is joined to the R group by a linkage which comprises an ether linkage (—$OR^{25}$), a thioether linkage (—$SR^{25}$), Or an amine linkage (—$NR^{25}R^{26}$ or —$NR^{25}R^{26}R^{27}$);

$R^{25}$, $R^{26}$ and $R^{27}$ independently comprise hydrogen, Z, an alkyl group wherein said alkyl group is saturated or unsaturated, linear or branched, substituted or unsubstituted, an alkoxy group that is saturated or unsaturated, branched or linear, substituted or unsubstituted, or when taken together, $R^{25}$ and $R^{26}$, and $R^{26}$ and $R^{27}$ independently comprise a five or six membered ring, and wherein any of $R^{25}$, $R^{26}$ or $R^{27}$ may further comprise said heteroatom containing side chain; and $R^8$ may comprise a substituted group capable of forming symmetric or asymmetric polymeric dye.

39. The process of claim 37, wherein the cells are contacted with said at least one viability dye before contacting steps (B), (C) and (D).

40. The process of claim 37, wherein the cells are contacted with said at least one viability dye during contacting steps (B), (C) and (D).

41. The process of claim 37, wherein the cells are contacted with said at least one viability dye after contacting steps (B), (C) and (D).

42. The process of claim 27, wherein in step (A), there is further provided at least one non-xanthene dye in step (B), step (C) and step (D).

43. The process of claim 42, wherein said at least one non-xanthene dye is a nuclear identification stain, calcein AM, Pheophorbide A, Chloromethylfluorescein diacetate (CMFDA), Hoechst 33342, BODIPY-Prazozin, Fura-2 AM, monobromobimane, BODIPY-Taxol or 3,3'-diethyloxacarbocyanine iodide (DIOC₂(3)].

44. The process of claim 27, wherein in step (E), measuring is carried out by a means comprising a flow cytometer, a microplate reader, a microscope, a fluorimeter, a high content screening platform, a high-content cell analysis system or a laser-scanning cytometer.

45. The process of claim 27, wherein said step (A), wherein in said step (A), there is provided a quenching reagent for minimizing extracellular fluorescent signal from said at least one xanthene compound.

46. The process of claim 45, wherein said quenching reagent comprises Evans Blue, o-tolidine, Trypan Blue, Trypan Red or Brilliant Black.

47. The process of claim 27, wherein in step (A), there is provided one or more surfactants for increasing cellular uptake of said at least one xanthene compound, and wherein said one or more surfactants are used in said contacting steps (B), (C) and (D).

48. The process of claim 47, wherein said one or more surfactants comprise Pluronic 127, L61, L81, P85 or F108.

49. The process of claim 27, wherein said one or more membrane transporter inhibitors comprise a specific inhibitor.

50. The process of claim 49, wherein said one or more membrane transporter inhibitors comprise more than one specific inhibitor.

51. The process of claim 49, wherein said specific inhibitor is valspodar (PSC833), verapamil, vanadate, PAK-104P, MK-571, FTC, Ko134, Elacridar (GF 120918), novobiocin, probenecid, BIB-E, disulfuram, indomethacin, furocemide, Penicillin G, sulfinpirazole, laniquidar (R101933), zosuquidar (LY335979), ontogeny (ONT-093), isothiocyanates, phytoestrogens, TAG-139, flavenoids, MS-209, NSAIDs, mitotane (NSC-38271), PK11195, cyclosporine D, anthranilamide, pipecolinate, quinoline, OC-144-093, diallyl sulfide, amooranin, agosterol A, siRNA, rifampicin, amiodarone, quinidine, quinine, nifedipine, dexniguldipin, LY455776, V-104, tricyclic izoxazoles, pluronic L61, or fumitremorgin C.

52. The process of claim 27, wherein said one or more membrane transporter inhibitors comprise both a general inhibitor and a specific inhibitor.

53. A process for determining the effect of a test compound on transport across a cell membrane by the membrane transporters MDR1, MRP and BCRP, said process comprising the steps of:
(A) providing:
(i) a clinical or biological sample comprising cells;
(ii) at least one xanthene compound that is transportable across a cell membrane by membrane transporters MDR1, MRP and BCRP; and
(iii) one or more test compounds;
(B) contacting cells from a first portion of said clinical or biological sample with said at least one xanthene compound;
(C) contacting cells from a second portion of said clinical or biological sample with said at least one xanthene compound and said one or more test compounds;
(D) measuring fluorescent signals generated in step (B) and step (C); and
(E) comparing the fluorescent signals measured in step (D) to determine elevated activities of said MDR1, MRP and BCRP, or a combination thereof, thereby determining the effect of said one or more test compounds on cell membrane transport by said membrane transporters, wherein said at least one xanthene compound has the structure

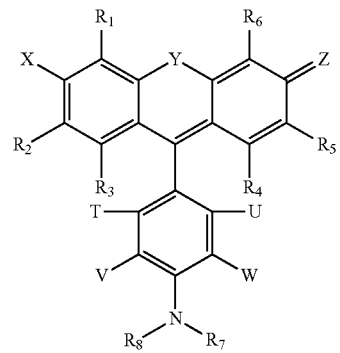

wherein
$R^1$-$R^6$ are independently H, halogen, carboxy, alkoxy, aryloxy, thiol, alkylthiol, arylthiol, azido, nitro, nitroso, cyano, amino, hydroxy, phosphonyl, sulfonyl, carbonyl, boronic acid, aryl, or heteroaryl; or alkyl, or alkoxy, optionally substituted one or more times by halogen, amino, hydroxy, phosphonyl, sulfonyl, carbonyl, boronic acid, aryl or heteroaryl, heteroatom Y is independently selected from O, S, Se, $NR^9$ and $CR.^{10}R^{11}$, X is independently selected from $OR^{12}$, $NR^{12}R^{13}$ and Z is independently selected from O and $NR^{16}R^{17}$, where each $R^9$, $R^{10}$, $R^{11}R^{12}$, $R^{13}$, $R^{16}$ and $R^{17}$ is independently H, an alkyl having 1-12 carbons, carboxyalkyl, substituted or non-substituted amino alkyl or alkylsulfonate, T and U are independently hydrogen, alkyl having 1-12 carbons, alkoxy having 1-12 carbons, aryloxy, amino, halogen, cyano, carboxy, carboxyalkyl, acetoxymethylcarbonyl, carbonyl, sulfonyl, phosphonyl, boronic acid, aryl, and heteroaryl, and V and W are independently selected from $OR^{14}$, $SR^{15}$ or $NR^{12}R^{13}$, such that at least one of V or W, in combination with $NR^7R^8$, forms a metal chelator, where each $R^7$, $R^8$, and $R^{12}$-$R^{15}$ are independently H, an alkyl having 1-12 carbons, carboxyalkyl, alkoxy or aryloxy.

54. A process for determining the effect of a test compound on transport across a cell membrane by the membrane transporters MDR1, MRP and/or BCRP, said process comprising the steps of:
(A) providing:
(i) at least three portions of a clinical or biological sample comprising cells;
(ii) at least one xanthene compound that is transportable across a cell membrane by membrane transporters MDR1, MRP and BCRP; and
(iii) one or more membrane transporter inhibitors;
(B) contacting cells from a first portion of said clinical or biological sample with said at least one xanthene compound under conditions sufficient to inhibit efflux of said at least one xanthene compound from said cells;
(C) contacting cells from a second portion of said clinical or biological sample with said at least one xanthene compound under conditions sufficient to permit efflux of said at least one xanthene compound from said cells;
(D) contacting cells from a third portion of said clinical or biological sample with said at least one xanthene compound (II) and said one or more inhibitors;
(E) measuring fluorescent signals generated in steps (B), (C) and D; and
(F) comparing the fluorescent signals measured in step (D) to determine elevated activities of said MDR1, MRP and BCRP, or a combination thereof, thereby determining the drug resistance of said cells of interest, wherein said at least one xanthene compound has the structure

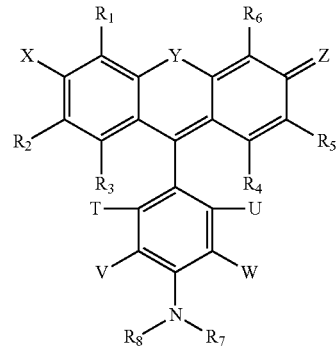

wherein
$R^1$-$R^6$ are independently H, halogen, carboxy, alkoxy, aryloxy, thiol, alkylthiol, arylthiol, azido, nitro, nitroso, cyano, amino, hydroxy, phosphonyl, sulfonyl, carbonyl, boronic acid, aryl, or heteroaryl; or alkyl, or alkoxy, optionally substituted one or more times by halogen, amino, hydroxy, phosphonyl, sulfonyl, carbonyl, boronic acid, aryl or heteroaryl, heteroatom Y is independently selected from O, S, Se, $NR^9$ and $CR.^{10}R^{11}$, X is independently selected from $OR^{12}$, $NR^{12}R^{13}$ and Z is independently selected from O and $NR^{16}R^{17}$, where each $R^9$, $R^{10}$, $R^{11}$, $R^{12}$, $R^{13}$, $R^{16}$ and $R^{17}$ is independently H, an alkyl having 1-12 carbons, carboxyalkyl, substituted or non-substituted amino alkyl or alkylsulfonate, T and U are independently hydrogen, alkyl having 1-12 carbons, alkoxy having 1-12 carbons, aryloxy, amino, halogen, cyano, carboxy, carboxyalkyl, acetoxymethylcarbonyl, carbonyl, sulfonyl, phosphonyl, boronic acid, aryl, and heteroaryl, and V and W are independently selected from $OR^{14}$, $SR^{15}$ or $NR^{12}R^{13}$, such that at least one of V or W, in combination with $NR^7R^8$, forms a metal chelator, where each $R^7$, $R^8$, and $R^{12}$-$R^{15}$ are independently H, an alkyl having 1-12 carbons, carboxyalkyl, alkoxy or aryloxy.

* * * * *